US006894177B2

(12) United States Patent
Lindström et al.

(10) Patent No.: US 6,894,177 B2
(45) Date of Patent: May 17, 2005

(54) INTERMEDIATE COMPOUNDS OF NON-NUCLEOSIDE REVERSE TRANSCRIPTASE INHIBITORS

(75) Inventors: Stefan Lindström, Uppsala (SE); Christer Sahlberg, Hagersten (SE); Hans Wallberg, Huddinge (SE); Genaidy Kalyanov, Bandhagen (SE); Lourdes Salvador Odén, Norrkoping (SE); Lotta Naeslund, Uppsala (SE)

(73) Assignee: Medivir AB, Huddinge (SE)

( * ) Notice: Subject to any disclaimer, the term of this patent is extended or adjusted under 35 U.S.C. 154(b) by 0 days.

(21) Appl. No.: 10/377,057

(22) Filed: Feb. 28, 2003

(65) Prior Publication Data

US 2003/0187266 A1 Oct. 2, 2003

Related U.S. Application Data

(62) Division of application No. 10/092,752, filed on Mar. 5, 2002, now Pat. No. 6,716,850.

(30) Foreign Application Priority Data

Mar. 5, 2001 (SE) .............................................. 0100733

(51) Int. Cl.$^7$ .......................................... C07D 311/02
(52) U.S. Cl. ........................... 549/385; 549/26; 549/43
(58) Field of Search ..................... 549/26, 43, 385; 546/79

(56) References Cited

U.S. PATENT DOCUMENTS 3,803,175 A    4/1974   Sparks et al.

FOREIGN PATENT DOCUMENTS

| DE | 2041563 A | 3/1971 |
|---|---|---|
| WO | Wo 93/03022 | 2/1993 |
| WO | WO 95/06034 | 3/1995 |
| WO | WO 99/36406 | 7/1999 |
| WO | WO 99/47501 | 9/1999 |
| WO | WO 00/39095 | 7/2000 |
| WO | WO 00/47561 | 8/2000 |
| WO | WO 00/56736 | 9/2000 |
| WO | WO 00/78315 A1 | 12/2000 |
| WO | WO 00/78721 A1 | 12/2000 |
| WO | WO 00/78755 A1 | 12/2000 |
| WO | WO 00/78756 A1 | 12/2000 |

OTHER PUBLICATIONS

Badger et al., CAOLD Abstract 52:17228c, 1959.*
Chatterjee et al., CAOLD Abstract 79:66064, 1973.*
Chatterjee et al., Mechanism, Stereoselectivity and Generality of a Novel Cyclopropane Formation, Tetrahedron Letters, No. 19, pp. 1683–1686,1973.*
Derrick L. J. Clive et al., "Synthesis of (±)–puraquinonic acid: an inducer of cell . . . ," J. Org. Chem. 2001, 66, pp. 954–961. XP–002216804.

M.G. Kulkarni et al., "Synthesis of novel 3–allylbenzofurans via . . . ," Synthesis. 1997, 12, pp. 1420–1424. XP–001106509.
Biswajit Saha et al., "Intramolecular asymmetric cyclopropanation . . . ," Synlett. 2001, 1(1), pp. 114–116. XP–001106507.
Chi–Ming Che et al., "Asymmetric inter– and intramolecular cyclopropanation . . . ," J. Am. Chem. Soc. 2001, 123, pp. 4119–4129. XP–002216805.
Masakatsu Masumoto et al., "o–Benzochinon–monoformyl-methide durch . . . ," Angew. Chem. 1982, 94 (5), pp. 376–377. XP002216806.
Andre Rosowsky et al., "2,4–Diaminothiene [2,3–d] pyrimidine analogue . . . ," J. Med. Chem. 1993, 36, pp. 3103–3112. XP–001106506.
Manik S. Sardessai et al., "The bromination of 2,5–dimethoyxbenzaldehyde . . . ," Organic Preparations and Procedures Int. 1991, 23 (4), pp. 419–424. XP–002216807.
Takao Sakamoto et al., "Condensed heteroaromatic ring systems . . . ," Tetrahedron, 1991, 47 (10), pp. 1877–1886. XP001106510.

(Continued)

*Primary Examiner*—Deepak Rao
(74) *Attorney, Agent, or Firm*—Birch, Stewart, Kolasch & Birch, LLP

(57) ABSTRACT

Compounds of the formula I:

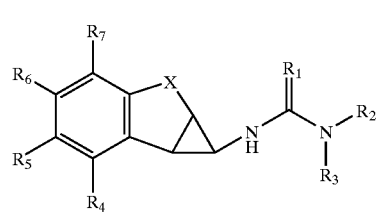

where;
$R_1$ is O, S;
$R_2$ is an optionally substituted nitrogen-containing heterocycle, wherein the nitrogen is located at the 2 position relative to the (thio)urea bond;
$R_3$ is H, $C_1$–$C_3$ alkyl,
$R_4$–$R_7$ are independently selected from H, $C_1$–$C_6$ alkyl, $C_2$–$C_6$ alkenyl, $C_2$–$C_6$ alkynyl, halo$C_1$–$C_6$ alkyl, $C_1$–$C_6$ alkanoyl, halo$C_1$–$C_6$ alkanoyl, $C_1$–$C_6$ alkoxy, halo$C_1$–$C_6$ alkoxy, $C_1$–$C_6$ alkyloxy-$C_1$–$C_6$ alkyl, halo$C_1$–$C_6$ alkyloxy-$C_1$–$C_6$ alkyl hydroxy-$C_1$–$C_6$ alkyl, amino-$C_1$–$C_6$ alkyl, carboxy-$C_1$–$C_6$ alkyl, cyano-$C_1$–$C_6$ alkyl, amino, carboxy, carbamoyl, cyano, halo, hydroxy, keto;
X is —(CH$_2$)$_n$—D—(CH$_2$)$_m$—;
D is —O—, —S—;
n and m are independently 0 or 1;
and prodrugs and pharmaceutically acceptable salts thereof, have utility as inhibitors of HIV-1 reverse transcriptase, particularly drug escape mutants.

14 Claims, No Drawings

OTHER PUBLICATIONS

Stephen F. Martin et al., "Iodocyclopropanes as Versatile Intermediates . . . ," Tetrahedron Letters, 1998, 39, pp. 1521–1524. XP002216808.

Tatsuya Uchida et al., "Co(II)–salen–catalyzed asymmetric intramolecular cyclopropanation . . . ," Tetrahedron Letters, 2001, 42, pp. 2521–2524. XP–002216809.

Yuki Takekawa et al., "Selective cleavage of the trisubstituted . . . ," Tetrahedron Letters, 1999, 40, pp. 6817–6820. XP–002216810.

Eric L. Dias et al., "Rhodium (I)–Catalyzed homologation of aromatic . . . ," J. Am. Chem. Soc. 2001, 123, pp. 2442–2443. XP002216811.

Robert S. Coleman et al., "A covergent approach to the . . . ," Organic Letter, 2001, 3 (8), pp. 1141–1144. XP002216812.

Leticia Perez–Serrano et al., "Synthesis of tricyclic aromatic compounds by the . . . ," J. Org. Chem. 2000, 65, pp. 3513–3519. XP–002216813.

Gregory H. Merriman et al.,"The Synthesis of N–(Pyridylamino) tetrahydroisoquinolines and . . . ," Synlett, 2000, 1, pp. 137–0139. XP001106583.

Arun K. Jain et al., "Some new constituents from . . . ," J. Indian Chem. Soc., Aug. 1991, pp. 452–454. XP–002216814.

Reckendorf, W. Meyer eta l.; "Synthesis of Methyl 4, 6–O–Benzylidene–2, 3 . . ." Angew. Chem. Internat. Edit. vol. 7 (1968) No. 2.

Reckendorf, W. Meyer et al.; "Synthesis von 2.3–[2–Amino–athyliden] . . ." Chem. Ber. 105, 686–695 (1972).

Hogberg, Marita et al.; "Urea–PETT Compounds as a New Class . . ." J. Med. Chem. 1999, 42, 4150–4160.

Cantrell, Amanda S. et al.; "Phenethylthiazolythiourea (PETT) Compounds . . ." J. Med. Chem. 199, 39, 4261–4274.

Bell, Frank W. et al.; "Phenethylthiazolethiourea (PETT) Compounds, a New Class of . . ." Reprinted from Journal of Medical Chemistry, 1995, 38, pp. 4929–4936.

Kirmase, Wolgang et al.; "Carbenes and the O–H Bond; . ." J. Org. Chem. 1988, 53, 763–767.

* cited by examiner

INTERMEDIATE COMPOUNDS OF NON-NUCLEOSIDE REVERSE TRANSCRIPTASE INHIBITORS

TECHNICAL FIELD

This invention relates to non-nucleoside reverse transcriptase inhibitors active against HIV-1 and having an improved resistance and pharmacokinetic profile. The invention further relates to novel intermediates in the synthesis of such compounds and the use of the compounds in antiviral methods and compositions.

BACKGROUND TO THE INVENTION

Non nucleoside reverse transcriptase inhibitors (NNRTI) bind to an allosteric site on reverse transcriptase and represent an important development in the arsenal of drugs against HIV, particularly HIV-1. International patent application WO 93/03022, discloses thiourea NNRTI which were later denoted "PETT" (phenyl ethyl thiazolyl thiourea) compounds in J Med Chem 39 6 1329–1335 (1995) and J Med Chem 39 21 4261–4274 (1996). International patent application nos. WO99/47501, WO/0039095, WO/0056736, WO00/78315 and WO00/78721 describe thiourea PETT derivatives which have allegedly been optimised against a composite RT binding pocket.

International patent application no WO95/06034 and J Med Chem 42 4150–4160 (1999) disclose urea isosteres of PETT NNRTIs. International patent application no WO99/36406 discloses urea NNRTI compounds with a freestanding cyclopropyl bridge, wherein the phenyl left hand wing bears an obligate 6-hydroxy function and international patent application no WO00/47561 discloses prodrugs of such compounds.

Although the urea and thiourea NNRTI disclosed in the above documents are active against reverse transcriptase, especially that of HIV-1, the nature of the HIV virus with its extreme lack of replicative fidelity and consequent tendency to rapid resistance development prompts a demand for further antiretroviral agents with enhanced antiviral performance against problematic drug escape mutants, notably at the RT 100, 103 and/or 181 positions.

Additionally, modern HIV therapy regimes, denoted HAART, Highly Active Anti Retroviral Therapy, administer antivirals as combinations of three or more antivirals of various classes, which combinations are administered for prolonged periods, if not for life. HAART requires the patient to follow a complicated dosing schedule with sometimes dozens of tablets per day taken at various times of the day in some cases before and in other cases after the ingestion of food. There is thus a need for antiretroviral preparations allowing greater flexibility in dosing to facilitate patient compliance.

BRIEF DESCRIPTION OF THE INVENTION

In accordance with a first aspect of the invention there are provided compounds of the formula I:

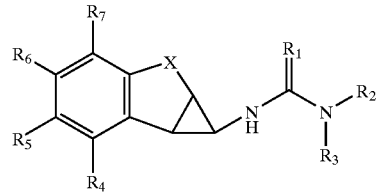

I where;

$R_1$ is O, S;

$R_2$ is an optionally substituted, nitrogen-containing heterocycle, wherein the nitrogen is located at the 2 position relative to the (thio)urea bond;

$R_3$ is H, $C_1$–$C_3$ alkyl, $R_4$–$R_7$ are independently selected from H, $C_1$–$C_6$ alkyl, $C_2$–$C_6$ alkenyl, $C_2$–$C_6$ alkynyl, halo$C_1$–$C_6$ alkyl, $C_1$–$C_6$ alkanoyl, halo$C_1$–$C_6$ alkanoyl, $C_1$–$C_6$ alkoxy, halo$C_1$–$C_6$ alkoxy, $C_1$–$C_6$ alkyloxy-$C_1$–$C_6$ alkyl, halo$C_1$–$C_6$ alkyloxy-$C_1$–$C_6$ alkyl hydroxy-$C_1$–$C_6$ alkyl, amino-$C_1$–$C_6$ alkyl, carboxy-$C_1$–$C_6$ alkyl, cyano-$C_1$–$C_6$ alkyl, amino, carboxy, carbamoyl, cyano, halo, hydroxy, keto and the like;

X is —$(CH_2)_n$—D—$(CH_2)_m$—

D is —$NR_8$—, —O—, —S—, —S(=O)— or —S(=O)$_2$—

$R_8$ is H, $C_1$–$C_3$ alkyl n and m are independently 0 or 1;

and pharmaceutically acceptable salts and prodrugs thereof.

The currently preferred value for $R_1$ is O, that is a urea derivative, although $R_1$ as S (ie a thiourea derivative) is also highly potent.

Representative values for $R_2$ include thiazolyl, pyridyl, pyrimidyl, pyrazinyl, pyridazinyl, pyrrolyl, imidazolyl, indolyl, triazolyl, tetrazolyl, piperidyl, piperazinyl and fused rings such as benzothiazolyl, benzopyridyl, benzodiazolyl, benzimidazolyl, quinolyl, purinyl and the like, any of which can be optionally substituted.

Preferred $R_2$ values include pyrid-2-yl and thiazol-2-yl.

The optional substituents to $R_2$ can include up to three substituents such as $C_1$–$C_6$ alkyl, $C_1$–$C_6$ alkoxy, $C_2$–$C_6$ alkenyl, $C_2$–$C_8$ alkynyl, $C_2$–$C_8$ alkenoxy, $C_1$–$C_6$ alkoxy $C_1$–$C_6$ alkyl, $C_1$–$C_6$ alkanoyl, halo$C_1$–$C_6$ alkyl, $C_1$–$C_4$ alkanoyloxy, $C_1$–$C_4$ alkylthio, amino (including $C_1$–$C_3$ alkyl-substituted amino), carboxy, carbamoyl, cyano, halo, hydroxy, aminomethyl, carboxymethyl, hydroxymethyl, nitro, aryl, (such as phenyl, pyrrol-1-yl, tetrazol-5-yl, triazol-4-yl, pyridyl, pyrimidyl, pyrazinyl, imidazolyl, indolyl, piperidyl, piperazinyl, and the like) substituted (as herein defined) aryl, or —$SO_2Q$ or —$C(=O)Q$, where Q is $C_1$–$C_6$ alkyl, halosubstituted $C_1$–$C_6$ alkyl, aryl (as herein defined), substituted (as herein defined) aryl or amino. Heteroatoms in $R_2$ can be derivatised, such as with $C_1$–$C_6$ alkyl, oxo and the like. The optional $R_2$ substituent may be ortho or meta to the bond to the (thio)urea function but is preferably para.

Preferred optional substituents to $R_2$ include ethynyl, phenoxy, pyrrid-1-yl, cyclopropyl, phenyl, halo-substituted phenyl (especially para and meta chloro and fluorophenyl), and dimethylamino. Particularly preferred $R_2$ substituents include halo (F, Br, Cl and I) and cyano. Preferred halo groups include Cl.

The currently preferred value for $R_3$ is H.

Preferably $R_4$ is hydrogen, halo or hydroxy, especially fluoro.

Preferably $R_5$ is halo, $C_{1-3}$ alkylcarbonyl, C1–3alkyloxy or H, especially fluoro and most preferably H.

Preferably $R_6$ is hydrogen, halo, $C_1$–$C_3$alkyloxy, C1–3alkylcarbonyl, cyano or ethynyl, especially methoxy or fluoro and most preferably H.

Preferably $R_7$ is hydrogen, halo, $C_{1-3}$alkyloxy, or $C_{1-3}$alkylcarbonyl, most preferably fluoro.

Preferably $R_5$ and $R_6$ are H and $R_4$ and $R_7$ are halo, most preferably both are fluoro.

Preferably D is —O—, n is 0, m is 1, $R_1$ is O, $R_2$ is substituted pyrid-2-yl and $R_3$ is H. An alternative preferred embodiment embraces compounds wherein D is —O—, n is 0, m is 1, $R_1$ is S, $R_2$ is substituted pyrid-2-yl and $R_3$ is H.

The compounds of formula I may be administered as a racemic mixture, but preferably the cyclopropyl moiety intermediate the (thio)urea function, X and the phenyl ring (denoted Y below) is at least 75% such as around 90% enantiomerically pure with respect to the conformation:

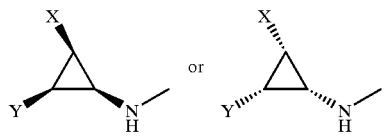

Prefered optical isomers of the compounds of formula I show a negative optical rotation value. Such isomers, for example when X is —O—CH$_2$—, tend to elute less rapidly from a chiral chromatagram, for example chiral AGP 150× 10 mm, 5 µm; Crom Tech LTD Colomn, flow rate 4 ml/min, mobile phase 89 vol % 10 mM HOAc/NH$_4$OAc in acetonitrile. On the basis of preliminary x-ray crystallography analysis a presently favoured absolute configuration appears to be:

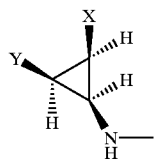

The currently preferred value for D is —O—. Convenient values for n and m include 1:0 and 1:1. Preferred values of n:m include 0:2 and especially 0:1, that is a chroman derivative. Particularly preferred compounds have stereochemistry corresponding to (1S,1aR,7bR)-1,1a,2,7b-tetrahydrocyclopropa[c]chromen-1-yl. For the sake of clarity, it is noted that the structure:

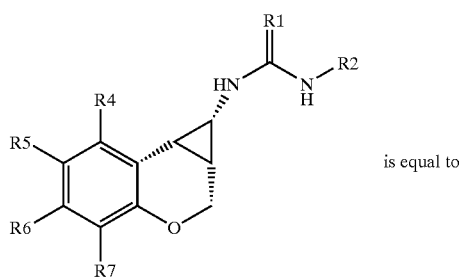

is equal to

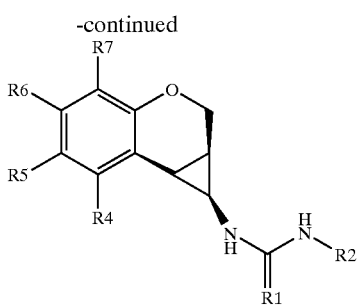

The expression $C_1$–$C_n$ alkyl, where n is 3, 6, 7 etc or lower alkyl includes such groups as methyl, ethyl, n-propyl, isopropyl, n-butyl, s-butyl, t-butyl, n-pentyl, n-hexyl, 3-methyl pentyl and the like. The term halo refers to chloro, bromo, fluoro and iodo, especially fluoro. $C_1$–$C_n$ alkoxy refers to groups such as methoxy, ethoxy, propoxy, t-butoxy and the like. $C_2$–$C_n$ alkenyl, refers to groups such as vinyl, 1-propen-2-yl, 1-buten-4-yl, 1-penten-5-yl, 1-buten-1-yl and the like. $C_1$–$C_n$ alkylthio includes methylthio, ethylthio, t-butylthio and the like. $C_1$–$C_n$ alkanoyloxy includes acetoxy, propionoxy, formyloxy, butyryloxy and the like. $C_2$–$C_n$ alkenoxy includes ethenyloxy, propenyloxy, iso-butoxyethenyl and the like. Halo$C_1$–$C_n$ alkyl (including complex substituents comprising this moiety such as halo$C_1$–$C_n$ alkyloxy) includes alkyls as defined herein substituted 1 to 3 times by a halogen including trifluormethyl, 2-dichloroethyl, 3,3-difluoropropyl and the like. The term amine includes goups such as NH$_2$, NHMe, N(Me)$_2$ which may optionally be substituted with halogen, $C_1$–$C_7$ acyloxy, $C_1$–$C_6$ alkyl, $C_1$–$C_6$ alkoxy, nitro, carboxy, carbamoyl, carbamoyloxy cyano, methylsulphonylamino and the like. Carboxy, carboxymethyl and carbamoyl include the corresponding pharmaceutically acceptable $C_1$–$C_6$ alkyl and aryl esters.

Prodrugs of the compounds of formula I are those compounds which following administration to a patient release a compound of the formula I in vivo. Typical prodrugs are pharmaceutically acceptable ethers and especially esters (including phosphate esters) when any of $R_4$–$R_7$ or the optional substituent to $R_2$ represent an hydroxy function, pharmaceutically acceptable amides or carbamates when any of the $R_2$ substituent or $R_4$–$R_7$ represent an amine function or pharmaceutically acceptable esters when the $R_2$ substituent or $R_4$–$R_7$ represent a carboxy function.

The compounds of formula I can form salts which form an additional aspect of the invention. Appropriate pharmaceutically acceptable salts of the compounds of formula I include salts of organic acids, especially carboxylic acids, including but not limited to acetate, trifluoroacetate, lactate, gluconate, citrate, tartrate, maleate, malate, pantothenate, isethionate, adipate, alginate, aspartate, benzoate, butyrate, digluconate, cyclopentanate, glucoheptanate, glycerophosphate, oxalate, heptanoate, hexanoate, fumarate, nicotinate, palmoate, pectinate, 3-phenylpropionate, picrate, pivalate, proprionate, tartrate, lactobionate, pivolate, camphorate, undecanoate and succinate, organic sulphonic acids such as methanesulphonate, ethanesulphonate, 2-hydroxyethane sulphonate, camphorsulphonate, 2-napthalenesulphonate, benzenesulphonate, p-chlorobenzenesulphonate and p-toluenesulphonate; and inorganic acids such as hydrochloride, hydrobromide, hydroiodide, sulphate, bisulphate, hemisulphate, thiocyanate, persulphate, phosphoric and sulphonic acids.

Hydroxy protecting group as used herein refers to a substituent which protects hydroxyl groups against undesirable reactions during synthetic procedures such as those O-protecting groups disclosed in Greene, "Protective Groups In Organic Synthesis," (John Wiley & Sons, New York (1981)). Hydroxy protecting groups comprise substituted methyl ethers, for example, methoxymethyl, benzyloxymethyl, 2-methoxyethoxymethyl, 2-(trimethylsilyl)ethoxymethyl, t-butyl and other lower alkyl ethers, such as isopropyl, ethyl and especially methyl, benzyl and triphenylmethyl; tetrahydropyranyl ethers; substituted ethyl ethers, for example, 2,2,2-trichloroethyl; silyl ethers, for example, trimethylsilyl, t-butyldimethylsilyl and t-butyldiphenylsilyl; and esters prepared by reacting the hydroxyl group with a carboxylic acid, for example, acetate, propionate, benzoate and the like.

The invention further provides pharmaceutical compositions comprising the compounds of the invention and pharmaceutically acceptable carriers or diluents therefor. Additional aspects of the invention provide methods for the inhibition of HIV comprising administering a compound of the formula I to a subject afflicted with or exposed to HIV-1.

The HIV-1 may comprise a drug escape mutant, such as HIV strain comprising the mutations at the 100, 103 and/or 181 mutations, especially K103N.

The invention also extends to the use of the compounds of formula I in therapy, such as in the preparation of a medicament for the treatment of HIV infections.

In treating conditions caused by HIV, the compounds of formula I are preferably administered in an amount to achieve a plasma level of around 100 to 5000 nM, such as 300 to 2000 nM. This corresponds to a dosage rate, depending on the bioavailability of the formulation, of the order 0.01 to 10 mg/kg/day, preferably 0.1 to 2 mg/kg/day. A typical dosage rate for a normal adult will be around 0.05 to 5 g per day, preferably 0.1 to 2 g such as 500–750 mg, in one to four dosage units per day. As with all pharmaceuticals, dosage rates will vary with the size and metabolic condition of the patient as well as the severity of the infection and may need to be adjusted for concomitant medications.

In keeping with the usual practice with HIV inhibitors it is advantageous to co-administer one to three additional antivirals to provide synergistic responses and to ensure complementary resistance patterns. Such additional antivirals may include AZT, ddI, ddC, D4T, 3TC, DAPD, alovudine, abacavir, adefovir, adefovir dipivoxil, bis-POC-PMPA, GW420 867X, foscarnet, hydroxyurea, Hoechst-Bayer HBY 097, efavirenz, trovirdine, capravirine, nevirapine, delaviridine, tipranavir, emtricitabine, PFA, H2G (omaciclovir), MIV-606 (valomaciclovir stearate), TMC-126, TMC-125, TMC-120, efavirenz, DMP-450, loviride, ritonavir, (including kaletra), lopinavir, saquinavir, lasinavir, indinavir, amprenavir, amprenavir phosphate, nelfinavir and the like, typically at molar ratios reflecting their respective activities and bioavailabilities. Generally such ratio will be of the order of 25:1 to 1:25, relative to the compound of formula I, but may be lower, for instance in the case of cytochrome antagonists such as ritonavir.

Compounds of the invention are typically prepared as follows:

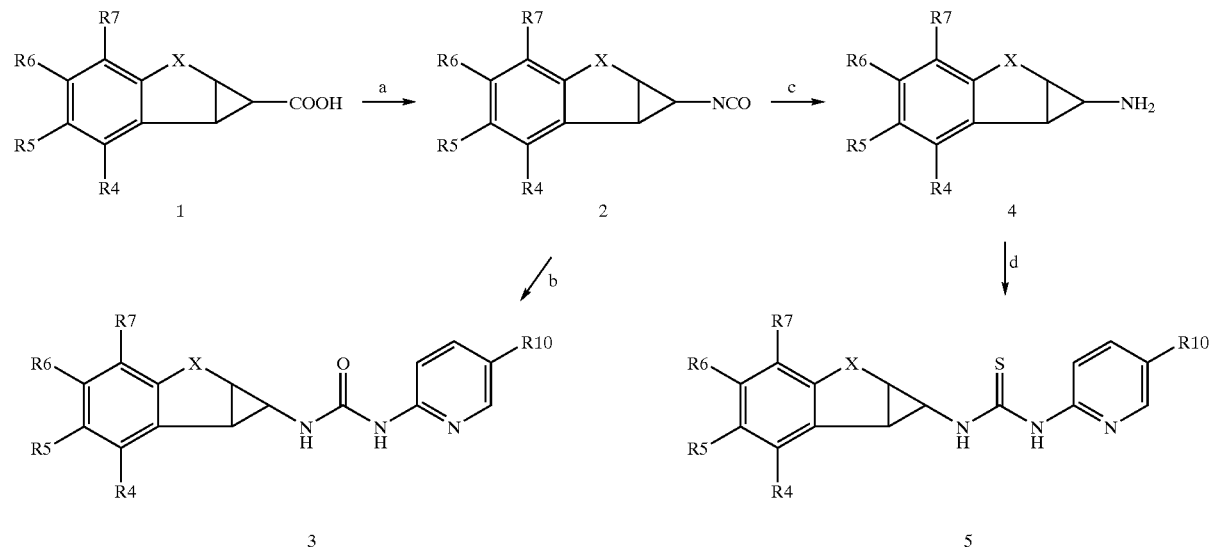

(a) DPPA, Et₃N, toluene; (b) substituted 2-aminopyridine; (c) aqueous HCl, dioxane; (d) substitued 2-pyridyl isothiocyanate.

Compounds of the general formula (I), wherein $R_1$ is O (urea) or S (thiourea), $R_2$ is, for instance, a 5-substituted pyrid-2-yl, and $R_3$ is H, are prepared by methods shown in Scheme 1. The cyclopropanecarboxylic acid 1-Scheme-1 is converted to the acyl azide and heated to 120° C. to induce Curtius rearrangement and provide the isocyanate 2-Scheme-1. The urea 3-Scheme-1 is obtained by coupling of the isocyanate with the relevantly substituted 2-aminopyridine. Hydrolysis of the isocyanate as in step (c) which results in the cyclopropylamine 4-Scheme-1, followed by reaction with a 2-pyridyl isothiocyanate provides the thiourea 5-Scheme-1. The isothiocyanate may be prepared from the optionally ring substituted 2-aminopyridine by known methods, such as treatment with thiophosgene or thiocarbonyidiimidazole. $R_3$ variants of formula I are prepared correspondingly using the appropriately amine-substituted amino-$R_2$, ie 2-(N-methylamino)pyridine for $R_3$ as methyl. Many 2-aminopyridines are commercially available and others are described in literature, for example those shown in Scheme 2. $R_1$=S compounds can alternatively be prepared from the isothiocyanate corresponding to 2-Scheme 2 or from amine 3-Scheme 2 and amino-R$_2$ in conjunction with an RC(=S)R' both as described in WO 9303022. Although Scheme 1 has been illustrated with a substituted pyridyl it is readily apparent that corresponding couplings can be used for other R$_2$ variants such as optionally substituted thiazolyl, pyrazinyl, benzothiazolyl, pyrimidinyl etc.

Scheme 2

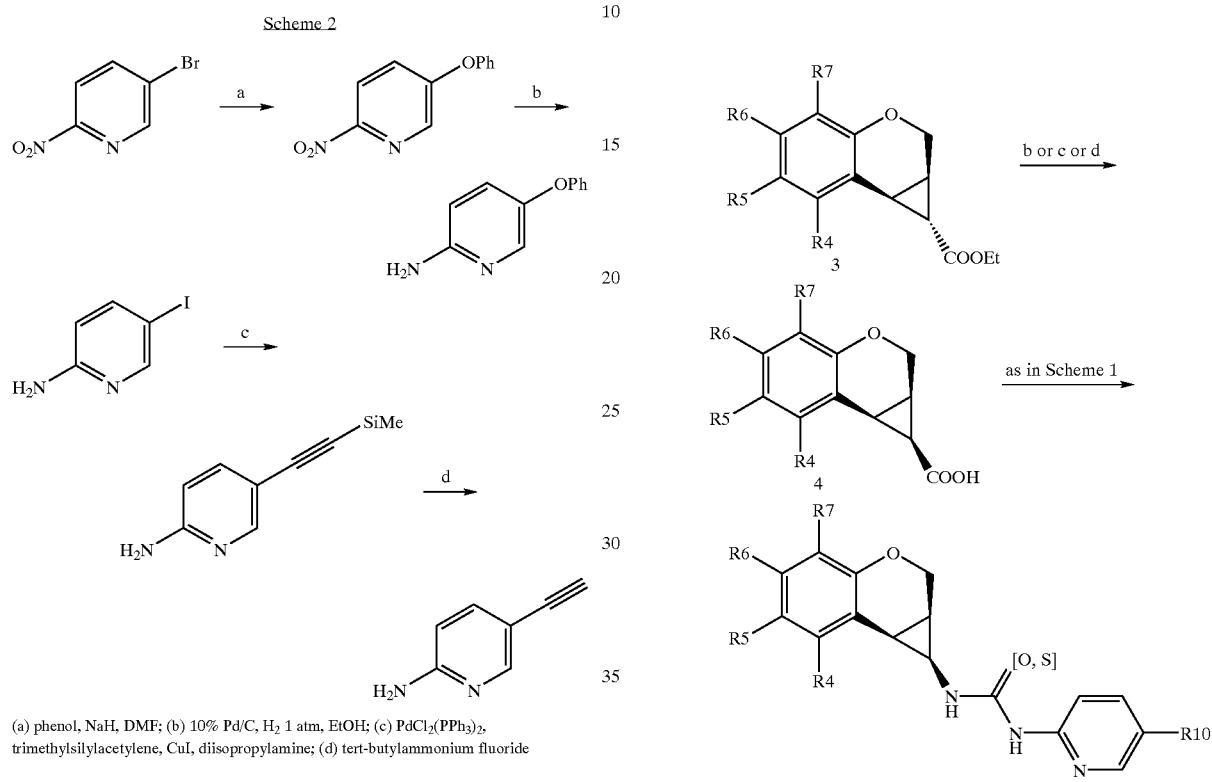

(a) phenol, NaH, DMF; (b) 10% Pd/C, H$_2$ 1 atm, EtOH; (c) PdCl$_2$(PPh$_3$)$_2$, trimethylsilylacetylene, CuI, diisopropylamine; (d) tert-butylammonium fluoride Replacement of the bromine in 5-bromo-2-nitropyridine by a phenoxy group, followed by reduction of the nitro group affords the 2-amino-5-phenoxypyridine. The Sonogashira coupling of 2-amino-5-iodopyridine with the terminal alkyne SiMe$_3$C≡CH in the presence of catalytic amounts of bis(triphenylphosphine)palladium dichloride and cuprous iodide as in step (c) provides the 2-amino-5-(2-trimethylsilylethynyl)pyridine. Removal of the silyl group by TBAF yields 2-amino-5-ethynylpyridine which can be coupled to the isocyanate as described in Scheme 1. Alternatively, treatment with TBAF may be performed on the urea 3-Scheme-1 or thiourea 5-Scheme-1 where R10 is —C≡CSiMe$_3$ to convert R10 to —C≡CH.

Scheme 3

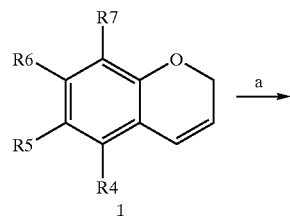

(a) ethyl diazoacetate, catalyst, CH$_2$Cl$_2$; (b) chromatography and then reflux with LiOH, H$_2$O, MeOH; (c) reflux with LiOH, H$_2$O, MeOH and then chromatography; (d) rt, NaOH, H$_2$O, MeOH and then reflux with LiOH, H$_2$O, MeOH Compounds of the general formula (I), wherein R1 is O (urea) or S (thiourea), R2 is, for example, a 5-substituted pyrid-2-yl, R3 is H, X is —D—CH$_2$, and wherein the cyclopropyl moiety has the relative configuration

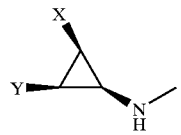

are prepared by methods shown in Scheme 3. Cyclopropanation of the double bond in the chromene 1-Scheme-3 with ethyl diazoacetate is catalyzed by cuprous or rhodium(II) salts such as CuI, (CuOTf)$_2$-benzene, and Rh$_2$(OAc)$_4$ in solvents such as dichloromethane, 1,2-dichloroethane, or chloroform. The reaction provides a diastereomeric mixture of the cyclopropanecarboxylic acid ethyl esters 2-Scheme-3, with the all cis relative configuration, and its trans isomer 3-Scheme-3. Separation by column chromatography of the cis and trans diastereomers may be accomplished at this stage, followed by hydrolysis of the isolated 2-Scheme-3, such as by refluxing in aqueous methanolic LiOH, to yield a racemic mixture of the all cis cyclopropanecarboxylic acid 4-Scheme-3, as described in step (b). Alternatively, the diastereomeric mixture of ethyl esters may be subjected to hydrolysis, and separation conducted on the mixture of cyclopropanecarboxylic acids to provide the isolated all cis isomer, as in step (c). Step (d) involves isolation of the cis ethyl ester 2-Scheme-3 which may also be done by selective hydrolysis of the trans 3-Scheme-3 at lower temperatures, such as treatment with aqueous methanolic NaOH at ambient temperature. The isolated cis ethyl ester may then be hydrolyzed in the usual manner to the cyclopropanecarboxylic acid 4-Scheme-3. The cyclopropanecarboxylic acid is subjected to the methods outlined in Scheme 1 to obtain the urea or thiourea 5-Scheme-3. The chromenes 1-Scheme-3 are prepared by methods shown in Schemes 4, 5, and 6.

Although this scheme 3 has been illustrated with a D=O variant it will be apparent that corresponding manipulations will be available to the D=S, S=O; S(=O)$_2$ and D=NR8 variants. When R8 is H, the nitrogen is typically protected with a conventional secondary amine protecting group, such as those described in Greene & Wuts Protective Groups in Organic Synthesis 2$^{nd}$ ed, Wiley N.Y. 1991).

such as K$_2$CO$_3$ in acetone or NaH in DMF, results in nucleophilic substitution of the halide to provide the ether 2-Scheme-4. Ring closure may be accomplished by heating the ether in N,N-dimethylaniline or polyethylene glycol to yield the chromene 3-Scheme-4.

Scheme 5

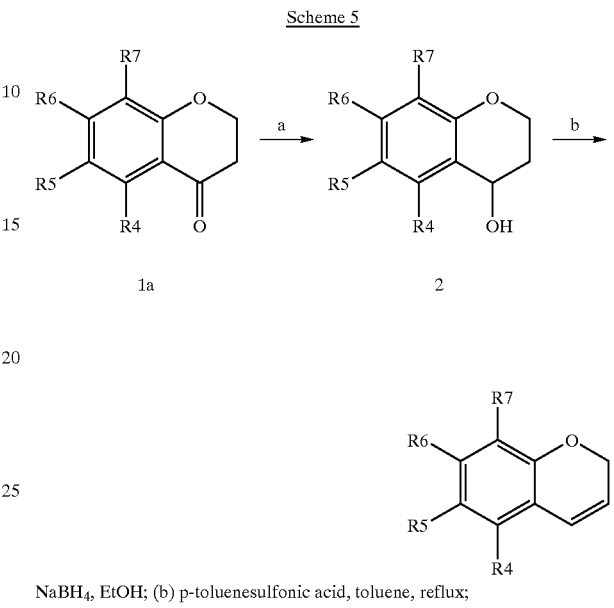

NaBH$_4$, EtOH; (b) p-toluenesulfonic acid, toluene, reflux;

Scheme 4

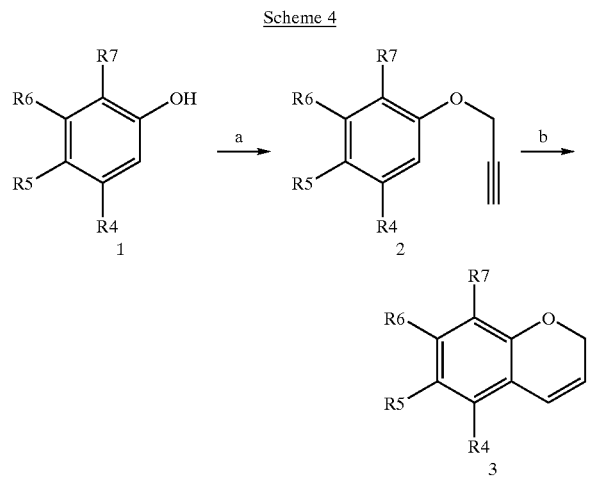

(a) 3-bromopropyne, K$_2$CO$_3$, acetone; (b) N, N-diethylaniline or PEG-200, 225° C.

Scheme 4 describes the preparation of chromenes, including many from commercially available disubstituted phenols, such as those wherein the substitution pattern in the benzene ring is as follows: R4 and R7 are halo; R4 and R6 are halo; R5 and R7 are halo; R4 is halo and R7 is C$_{1-3}$ alkylcarbonyl; and R4 is hydroxy while R5 is C$_{1-3}$ alkylcarbonyl. Reaction of the available disubstituted phenol 1-Scheme-4 with 3-bromopropyne in the presence of a base, Scheme 5 describes the preparation of chromenes, used as starting material in Scheme 3, from the appropriately substituted chromanones, which are readily accessed from commercially available chromanones, for example those wherein one of the positions in R4 to R7 is substituted with halo or C$_{1-3}$ alkoxy. Conversion of the carbonyl group in 4-chromanone 1a-Scheme-5 and to the corresponding alcohol by a suitable reducing agent such sodium borohydride in ethanol provides 2-Scheme-5. Refluxing the alcohol with small amounts of acid, such as p-TsOH in toluene, causes dehydration of 2-Scheme-5 to the desired chromene 1-Scheme-3. Corresponding manipulations will be available for other D variants. For example the corresponding 2H-1-benzothiopyran is readily prepared from commercially available (substituted) thiochroman-4-ones by reaction with a reductant such as a metal hydride for example lithium aluminium hydride in an organic solvent such as ether, followed by dehydration such as refluxing with an acid for example potassium acid sulphate or the like.

Scheme 6

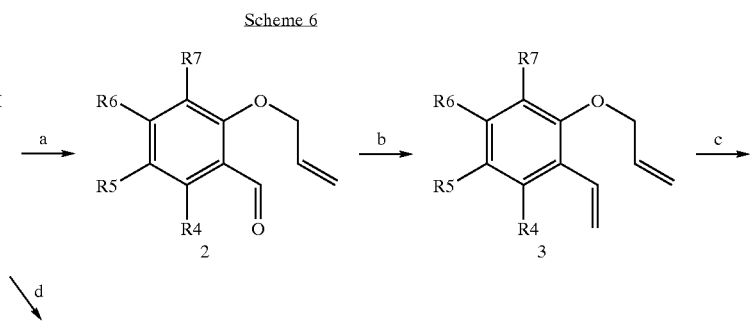

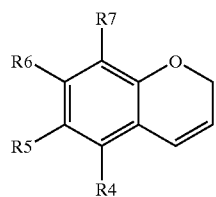

(a) allyl bromide, $K_2CO_3$, acetone; (b) $Ph_3PCH_3Br$, NaH, THF; (c) $Cl_2[Pcy_3]_2Ru=CHPh$, $CH_2Cl_2$ (d) $Ph_3P^+CH=CH_2\ Br^-$, DBU Chromenes, for use as starting material in Scheme 3, are prepared from substituted o-hydroxybenzaldehydes as shown by methods outlined in Scheme 6. Reaction of 1-Scheme-6 with allyl bromide in the presence of a base, such as $K_2CO_3$ in acetone, results in nucleophilic substitution of the halide to provide the ether 2-Scheme-6. Witting reaction transforms the aldehydic group into the olefin and provides 3-Scheme-6. The pair of terminal double bonds may undergo metathesis intramolecularly by treatment with a catalyst such as the ruthenium complex Grubb's catalyst in step (c) to produce the chromene. Alternatively 1-Scheme-6 can be cyclised directly as shown in step d) in the legend above.

Scheme 7

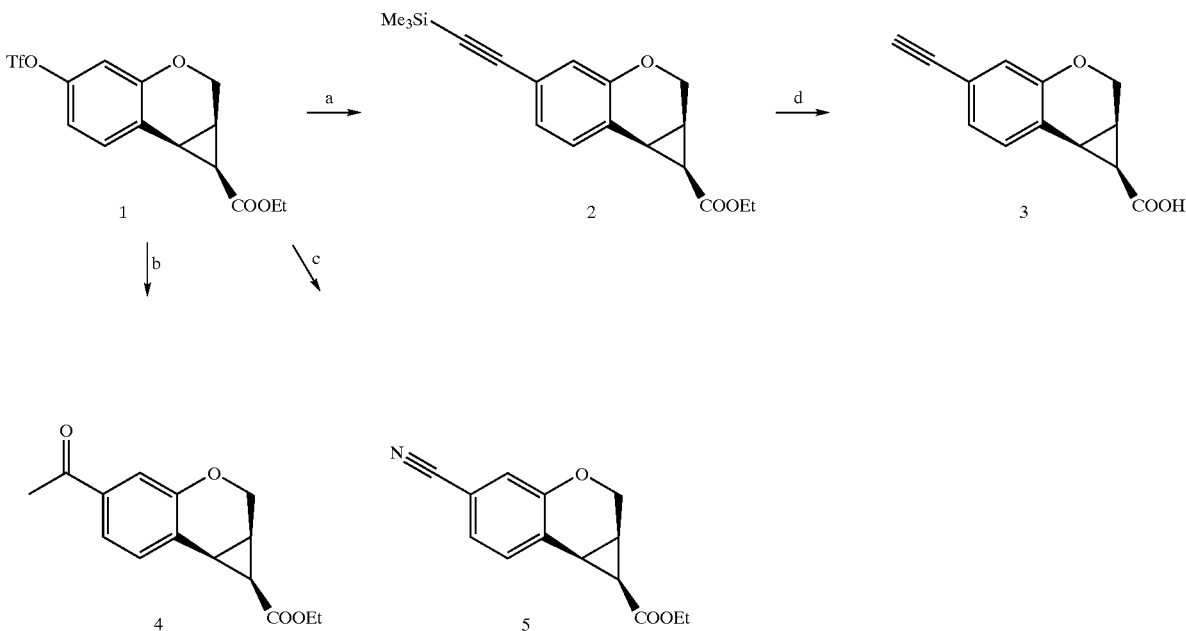

(a) Pd(0), DPPP, $Et_3N$, $(CH_3)_3SiC\equiv CH$; (b) Pd(0), butyl vinyl ether, DMF; (c) Pd (0), $Zn(CN)_2$, DMF; (d) NaOH, $H_2O$, MeOH Pd(0) catalyzed coupling of the triflate 1-Scheme-7 leads to the replacement of the trifluoromethanesulfonyloxy group and the introduction of other substiutents at R6. Thus, Scheme 7 provides the preparation of synthesis intermediates for use in scheme 3 to give the urea or thiourea 5-Scheme-3 wherein R6 is cyano, ethynyl, or $C_{1-3}$ alkylcarbonyl.

Scheme 8

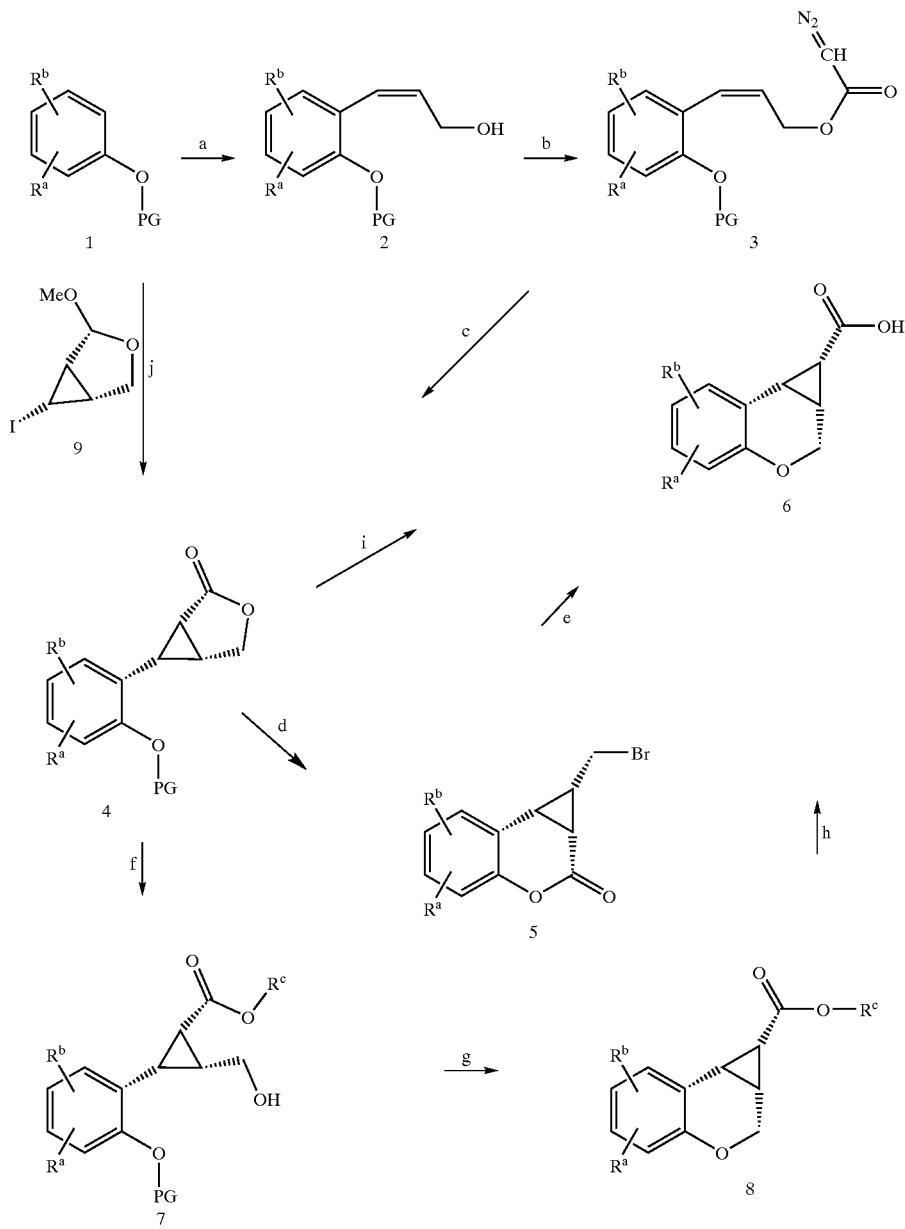

(a) BuLi/ZnCl$_2$, THF; Pd(OAc)$_2$, BrCH═CHCOOEt; DIBAL
(b) TsNHN═CHCOCl; PhNMe$_2$, NEt$_3$, CH$_2$Cl$_2$
(c) Rh$_2$(5-R-MEPY)$_4$, abs degassed dichloromethane
(d) 30% HBr, AcOH
(e) NaOH, H$_2$O
(f) NaOH; CO$_2$; I-PrI/DMSO
(g) IPrOH, HCl; DEAD, PPh$_3$, THF
(h) NaOH, MeOH:H$_2$O
(i) 1. BBr$_3$, CH$_2$Cl$_2$ 2. CH$_3$CN 3. NaOH, water
(j) 1. BuLi/ZnCl$_2$, THF; Pd(OAc) 2. cpd 9-Scheme-8 3. Jones reagent
  (chromic acid, sulfuric acid in acetone)

Convenient routes to compounds wherein X is —CH$_2$—O— are depicted in Scheme 8, where $R^a$ and $R^b$ are optional substituents $R_4$–$R_7$, which are suitably protected with conventional protecting groups as necessary and $R^c$ is a lower alkyl ester. Optionally substituted phenol 1-Scheme-8 which is hydroxy-protected with a protecting group such as methyl, MOM and the like is reacted with a base such as BuLi or the like in a solvent such as THF or the like and transformed to zinc salt by adding zinc chloride or the like. A catalyst such as Pd(OAc)$_2$ or the like is added along with an activated acrylate such as lower alkyl-cis-3-haloacrylate, for example BrCH═CHCOOEt or the like. The reaction mixture is cooled and a reducing agent such as DIBAL or the like is added portionwise and quenched to yield 2-Scheme-8. A hydrazone such as the p-toluenesulfonylhydrazone of glyoxylic acid chloride or the like and a base such as N,N-dimethylaniline or the like is added in a solvent such as $CH_2Cl_2$ or the like followed by the addition of another base such as $Et_3N$ or the like to yield 3-Scheme-8. The reaction product is dissolved in a solvent such as dichloromethane or the like which is preferably degassed. A chiral Doyle's catalyst such as $Rh_2(5-R-MEPy)_4$ (U.S. Pat. No. 5,175,311, available from Aldrich or Johnson Matthey), or the like is added to yield 4-Scheme-8 in a high enantiomeric excess such as greater than 80, preferably greater than 90% ee. Preferably, this compound is first reacted with $BBr_3$ in dichloromethane followed by the addition of acetonitrile the reaction mixture and finally sodiumhydroxide is added to give 6-Scheme-8. Alternatively, this product (4-Scheme-8) is ring-opened with an electrophile preferably HBr or the like under in conjunction with an acid such as AcOH or the like. Under acid conditions a spontaneous ring closure takes place to form chromenone 5-Scheme-8. When subjected to basic conditions such as NaOH or the like, the chromenone rearranges to form the chromencyclopropylcarboxylic acid 6-Scheme-8. Alternatively, 4-Scheme-8, for instance when the phenolic protecting group is MOM, can be subjected to basic conditions such as NaOH, carbon dioxide and a lower alkyl halide such as iPrI in a solvent such as DMSO to open the lactone and yield the alkyl ester 7-Scheme-8. Displacement of the hydroxy protecting group and ring closure with the free hydroxymethyl moiety occurs in acidic conditions such as iPrOH/HCl or the like followed by DEAD; $PPH_3$ in an organic solvent such as THF or the like.

Alternatively, in a convergent approach, compound 1-Scheme-8 is reacted with BuLi and transformed to a zinc salt. This salt reacted with the cyclopropyliodide, 9-Scheme-8, in a palladium-catalyzed reaction to give after reaction with Jone's reagent compound 4-Scheme-8. This carboxylic acid is in turn converted to the isocyanate as shown in Scheme 1 and subsequently to the heteroarylurea or heteroarylthiourea of the Formula I.

A further aspect of the invention provides novel intermediates useful in the above described syntheses of the compound of formula I. A preferred group of intermediates include compounds of the formula II:

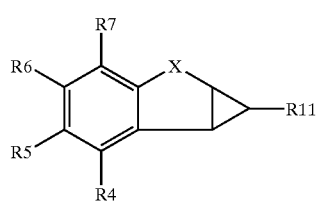

II where X and $R_4$–$R_7$ are as defined above and $R_{11}$ is —C(O)O$R_{12}$, where $R_{12}$ is H or a carboxy protecting group such as a lower alkyl ester; —NCO, —NCS or an amine such as $NH_2$. A favoured subset of the compounds of formula II have the formula II:

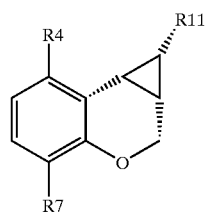

III where $R_4$ and $R_7$ are independently halo, most preferably fluoro, and $R_{11}$ is —COOH, a lower alkyl ester thereof, isocyanate, isothiocyanate or amino.

A further group of preferred intermediates includes compounds of the formula IV

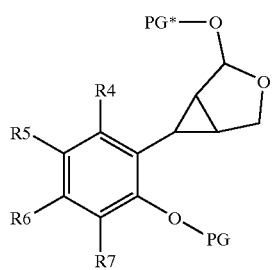

IV where $R_4$ to $R_7$ are as defined above, PG is an hydroxy protecting group and PG* is an hydroxy protecting group or together with the adjacent O defines a keto function.

A preferred subset of compounds of formula IV are those of formula V:

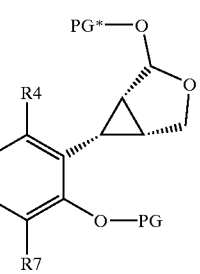

V where $R_4$ and $R_7$ are independently halo, most preferably fluoro, PG is lower alkyl, such as isopropyl, ethyl and most preferably methyl and PG* is lower alkyl such as isopropyl, ethyl and most preferably methyl or together with the adjacent O defines a keto group A still further group of preferred intermediates includes compounds of the formula VI:

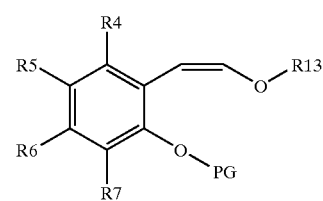

VI where $R_4$–$R_7$ are as defined above, PG is an hydroxy protecting group and $R_{13}$ is H, an ester thereof or an hydroxy protecting group. A preferred subset within formula VI has the formula VII:

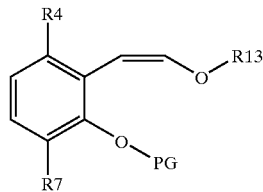

VII where $R_4$ and $R_7$ are independently halo, preferably fluoro, PG is lower alkyl, such as isopropyl, ethyl and most preferably methyl and $R_{12}$ is H or —C(=O)CH=N=N.

Favoured compounds of formula I include
cis-1-(5-Cyano-pyridin-2-yl)-3-(1,1a,2,7b-tetrahydro-cyclopropa[c]chromene-1-yl)-urea,
cis-1-(5-Cyano-pyridin-2-yl)-3-(1,1a,3,7b-tetrahydro-2-oxa-cyclopropa[a]naphthalen-1-yl)-urea,
cis-1-(5-Cyano-pyridin-2-yl)-3-(7-hydroxy-6-propionyl-1,1a,2,7b-tetrahydro-cyclopropa[c]chromen-1-yl)-urea,
cis-1-(6-Acetyl-7-hydroxy-1,1a,2,7b-tetrahydro-cyclopropa[c]chromen-1-yl)-3-(5-cyano-pyridin-2-yl)-urea,
cis-1-(5-Cyanopyridin-2-yl)-3-(7-fluoro-4-propionyl-1,1a,2,7b-tetrahydro-cyclopropa[c]chromen-1-yl)-urea,
cis-1-(5-Cyano-pyridin-2-yl)-3-(7-fluoro-4-methoxy-1,1a,2,7b-tetrahydro-cyclopropa[c]chromen-1-yl)-urea,
cis-1-(5-Cyano-pyridin-2-yl)-3-(7-fluoro-4-chloro-1,1a,2,7b-tetrahydro-cyclopropa[c]chromen-1-yl)-urea,
cis-1-(5-Chloro-pyridin-2-yl)-3-(4-chloro-7-fluoro-1,1a,2,7b-tetrahydro-cyclopropa[c]chromene-1-yl)-urea,
cis-1-(5-Bromo-pyridin-2-yl)-3-(4-chloro-7-fluoro-1,1a,2,7b-tetrahydro-cyclopropa[c]chromene-1-yl)-urea,
cis-1-(5-Cyano-pyridin-2-yl)-3-(5-cyano-1,1a,2,7b-tetrahydro-cyclopropa[c]chromen-1-yl)-urea,
cis-1-(5-Cyano-pyridin-2-yl)-3-(5-ethynyl-1,1a,2,7b-tetrahydro-cyclopropa[c]chromen-1-yl)-urea,
cis-1-(5-Acetyl-1,1a,2,7b-tetrahydro-cyclopropa[c]chromen-1-yl)-3-(5-cyano-pyridin-2-yl)-urea,
cis-1-(5-Methoxy-1,1a,2,7b-tetrahydro-cyclopropa[c]chromen-1-yl)-3-(5-cyano-pyridin-2-yl)-urea,
cis-1-(5-Cyano-pyridin-2-yl)-3-(N-acetyl-1,1a,3,7b-tetrahydro-2-oxa-cyclopropa[a]quinoline-1-yl))-urea,
cis-1-(5-Cyano-3-methyl-pyridin-2-yl)-3-(4,7-difluoro-1,1a,2,7b-tetrahydro-cyclopropa[c]chromen-1-yl)-urea,
cis-1-(4,7-Difluoro-1,1a,2,7b-tetrahydro-cyclopropa[c]chromen-1-yl)-3-(5-ethynyl-pyridin-2-yl)-urea,
cis-1-(5-Bromo-pyridin-2-yl)-3-(4,7-difluoro-1,1a,2,7b-tetrahydro-cyclopropa[c]chromen-1-yl)-urea,
cis-1-(4,7-Difluoro-1,1a,2,7b-tetrahydro-cyclopropa[c]chromen-1-yl)-3-(5-phenoxy-pyridin-2-yl)-urea,
cis-1-(5-Cyano-pyridin-2-yl)-3-(4,7-difluoro-1,1a,2,7b-tetrahydro-cyclopropa[c]chromen-1-yl)-thiourea,
1-(6-Chloro-5-cyano-pyridin-2-yl)-3-(5,7-difluoro-1,1a,2,7b-tetrahydro-cyclopropa[c]chromen-1-yl)urea,
1-(5-Cyano-pyridin-2-yl)-3-(5,7-difluoro-1,1a,2,7b-tetrahydro-cyclopropa[c]chromen-1-yl)urea,
cis-1-(4-Bromo-7-fluoro-1,1a,2,7b-tetrahydro-cyclopropa[c]chromen-1-yl)-3-(5-cyano-pyridin-2-yl)-urea,
cis-1-(4-Bromo-7-fluoro-1,1a,2,7b-tetrahydro-cyclopropa[c]chromen-1-yl)-3-(6-chloro-5-cyano-pyridin-2-yl)-urea,
cis-1-(4-Bromo-6-fluoro-1,1a,2,7b-tetrahydro-cyclopropa[c]chromen-1-yl)-3-(5-cyano-pyridin-2-yl)-urea,
cis-1-(4-Bromo-6-fluoro-1,1a,2,7b-tetrahydro-cyclopropa[c]chromen-1-yl)-3-(6-cloro-5-cyano-pyridin-2-yl)-urea,
cis-1-(5-Cyanopyridin-2-yl)-3-(6-fluoro-1,1a,2,7b-tetrahydro-cyclopropa[c]chromen-1-yl)urea,
cis N-[1a,6b-dihydro-1H-benzo[b]cyclopropa[d]thien-1-yl]-N'-(5-cyano-2-pyridinyl)-urea,
N-[(1S,1aR,7bR) or (1R,1aS,7bS)-1.1a,2,7b-tetrahydrocyclopropa[c]-[1]benzothiopyran-1-yl]-N'-(5-cyano-2-pyridinyl)urea,
cis-N-(5-bromo-2-pyridinyl)-N'-(7-chloro-4-fluoro-1,1a,2,7b-tetrahydrocyclopropa[c]chromen-1-yl)urea,
cis-N-(7-chloro-4-fluoro-1,1a,2,7b-tetrahydrocyclopropa[c]chromen-1-yl)-N'-(5-chloro-2-pyridinyl)urea,
cis-N-(7-chloro-4-fluoro-1,1a,2,7b-tetrahydrocyclopropa[c]chromen-1-yl)-N'-(5-cyano-2-pyridinyl)urea,
cis-N-(5-phenoxy-2-pyridinyl)-N'-(4,7-dichloro-1,1a,2,7b-tetrahydrocyclopropa[c]chromen-1-yl)urea,
cis-N-(5-bromo-2-pyridinyl)-N'-(4,7-dichloro-1,1a,2,7b-tetrahydrocyclopropa[c]chromen-1-yl)urea,
cis-N-(5-chloro-2-pyridinyl)-N'-(4,7-dichloro-1,1a,2,7b-tetrahydrocyclopropa[c]chromen-1-yl)urea,
cis-N-(5-cyano-2-pyridinyl)-N'-(4,7-dichloro-1,1a,2,7b-tetrahydrocyclopropa[c]chromen-1-yl)urea,
N-[(1S,1aR,7bR)-4,7-difluoro-1,1a,2,7b-tetrahydrocyclopropa[c]chromen-1-yl]-N'-(5-fluoro-2-pyridinyl)urea,
N-[(1S,1aR,7bR)-4,7-difluoro-1,1a,2,7b-tetrahydrocyclopropa[c]chromen-1-yl]-N'-(5-iodo-2-pyridinyl)urea,
N-[(1S,1aR,7bR)-4,7-difluoro-1,1a,2,7b-tetrahydrocyclopropa[c]chromen-1-yl]-N'-(3-isoxazolyl)urea,
N-[(1S,1aR,7bR)-4,7-difluoro-1,1a,2,7b-tetrahydrocyclopropa[c]chromen-1-yl]-N'-[4-(4-chlorophenyl)-1,3-thiazol-2-yl]urea,
N-[(1S,1aR,7bR)-4,7-difluoro-1,1a,2,7b-tetrahydrocyclopropa[c]chromen-1-yl]-N'-(6-fluoro-1,3-benzothiazol-2-yl)urea,
N-[(1S,1aR,7bR)-4,7-difluoro-1,1a,2,7b-tetrahydrocyclopropa[c]chromen-1-yl]-N'-(4-pyrimidinyl)urea
N-[(1S,1aR,7bR)-4,7-difluoro-1,1a,2,7b-tetrahydrocyclopropa[c]chromen-1-yl]-N'-(2-pyrazinyl)urea,
N-[(1S,1aR,7bR)-4,7-difluoro-1,1a,2,7b-tetrahydrocyclopropa[c]chromen-1-yl]-N'-(5-cyclopropyl-1H-pyrazol-3-yl)urea
and pharmaceutically acceptable salts thereof, especially enantiomerically enriched, for example greater than 80% by weight, preferably >90%, such as >97% ee or pure preparations comprising the (−) enantiomer.

Particularly preferred compound thus include
(−)-cis-1-(5-Cyano-pyridin-2-yl)-3-(4,7-difluoro-1,1a,2,7b-tetrahydro-cyclopropa[c]chromen-1-yl)-urea,
(−)cis-1-(5-Chloro-pyridin-2-yl)-3-(4,7-difluoro-1,1a,2,7b-tetrahydro-cyclopropa[c]chromen-1-yl)-urea; or
(−)-cis-1-(5-Cyano-pyridin-2-yl)-3-(4,7-difluoro-1,1a,2,7b-tetrahydro-cyclopropa[c]chromen-1-yl)-thiourea;
(−)-cis-1-(5-Fluoropyridin-2-yl)-3-(4,7-difluoro-1,1a,2,7b-tetrahydro-cyclopropa[c]chromen-1-yl)-urea,
(−)-cis-1-(5-Fluoropyridin-2-yl)-3-(4,7-difluoro-1,1a,2,7b-tetrahydro-cyclopropa[c]chromen-1-yl)-thiourea;
and pharmaceutically acceptable salts thereof.

While it is possible for the active agent to be administered alone, it is preferable to present it as part of a pharmaceutical formulation. Such a formulation will comprise the above defined active agent together with one or more acceptable carriers or excipients and optionally other therapeutic ingredients. The carrier(s) must be acceptable in the sense of being compatible with the other ingredients of the formulation and not deleterious to the recipient.

The formulations include those suitable for rectal, nasal, topical (including buccal and sublingual), vaginal or parenteral (including subcutaneous, intramuscular, intravenous and intradermal) administration, but preferably the formulation is an orally administered formulation. The formulations may conveniently be presented in unit dosage form, e.g. tablets and sustained release capsules, and may be prepared by any methods well known in the art of pharmacy.

Such methods include the step of bringing into association the above defined active agent with the carrier. In general, the formulations are prepared by uniformly and intimately bringing into association the active agent with liquid carriers or finely divided solid carriers or both, and then if necessary shaping the product. The invention extends to methods for preparing a pharmaceutical composition comprising bringing a compound of Formula I or its pharmaceutically acceptable salt in conjunction or association with a pharmaceutically acceptable carrier or vehicle. If the manufacture of pharmaceutical formulations involves intimate mixing of pharmaceutical excipients and the active ingredient in salt form, then it is often preferred to use excipients which are non-basic in nature, i.e. either acidic or neutral. Formulations for oral administration in the present invention may be presented as discrete units such as capsules, cachets or tablets each containing a predetermined amount of the active agent; as a powder or granules; as a solution or a suspension of the active agent in an aqueous liquid or a non-aqueous liquid; or as an oil-in-water liquid emulsion or a water in oil liquid emulsion and as a bolus etc.

With regard to compositions for oral administration (e.g. tablets and capsules), the term suitable carrier includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, stearic acid, glycerol stearate, silicone fluid, talc waxes, oils and colloidal silica. Flavouring agents such as peppermint, oil of wintergreen, cherry flavouring or the like can also be used. It may be desirable to add a colouring agent to make the dosage form readily identifiable. Tablets may also be coated by methods well known in the art. A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may be optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

DETAILED DESCRIPTION

Various aspects of the invention will now be illustrated by way of example only with reference to the following non-limiting examples.

EXAMPLE 1

(±)cis-1-(5-Cyano-pyridin-2-yl)-3-(1,1a,2,7b-tetrahydro-cyclopropa[c]chromene-1-yl)-urea a) ±cis-1,1a,2,7b-Tetrahydro-cyclopropa[c]chromene-1-carboxylic acid ethyl ester

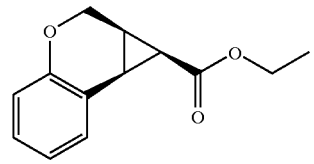

To a mixture of 2H-chromene (4.89 g, 37 mmol) and $(CuOTf)_2$-benzene (186 mg, 0.37 mmol) in 1,2-dichloroethane (80 mL) at 20° C., was added dropwise (3 h) a solution of ethyl diazoacetate (8.44 g, 74 mmol) in 1,2-dichloroethane (20 mL). After 15 min at 20° C., the reaction mixture was washed with $H_2O$ (100 mL). The $H_2O$ phase was washed with $CH_2Cl_2$ (50 mL) and the solvent of the combined organic phases was removed under reduced pressure. The crude product was column chromatographed (silica gel, 20→50% EtOAc in hexane), to give 1.96 g (24%) of ±cis-1,1a,2,7b-tetrahydro-cyclopropa[c]chromene-1-carboxylic acid ethyl ester and 3.87 g (48%) of ±-trans-1,1a,2,7b-tetrahydro-cyclopropa[c]chromene-1-carboxylic acid ethyl ester as a byproduct.

$^1$H-NMR (CDCl$_3$): 7.26 (d, 1H), 7.10 (dd, 1H), 6.90 (dd, 1H), 6.78 (d, 1H), 4.49 (dd, 1H), 4.20 (dd, 1H), 3.97 (q, 2H), 2.44 (dd, 1H), 2.14 (dd, 1H), 2.07–1.95 (m, 1H), 1.02 (t, 3H).

b) (±)-cis-1,1a,2,7b-Tetrahydro-cyclopropa[c]chromene-1-carboxylic acid

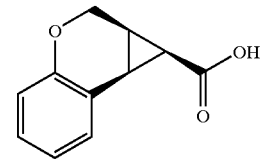

A mixture of (±)-cis-1,1a,2,7b-tetrahydro-cyclopropa[c]chromene-1-carboxylic acid ethyl ester (1.96 g, 9.0 mmol), LiOH (539 mg, 22.5 mmol), $H_2O$ (10 mL) and MeOH (20 mL) was heated to reflux for 2 h. The reaction mixture was concentrated to about 10 mL, 4N HCl was added dropwise giving a white precipitate. The reaction mixture was extracted with $CH_2Cl_2$ (3×15 mL) and the solvent of the combined organic phases was removed under reduced pressure. The crude product was crystallized from EtOAc/hexane, to give 435 mg (25%) of (±)-cis-1,1a,2,7b-tetrahydro-cyclopropa[c]chromene-1-carboxylic acid as a white solid.

$^1$H-NMR (CDCl$_3$): 9.80 (br s, 1H), 7.22 (d, 1H), 7.10 (dd, 1H), 6.89 (dd, 1H), 6.77 (d, 1H), 4.45 (dd, 1H), 4.22 (dd, 1H), 2.45 (dd, 1H), 2.14–1.98 (m, 2H).

c) (±)-cis-1-(5-Cyano-pyridin-2-yl)-3-(1,1a,2,7b-tetrahydro-cyclopropa[c]chromene-1-yl)-urea

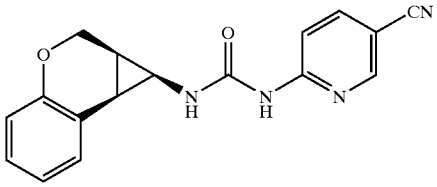

To a solution of (±)-cis-1,1a,2,7b-tetrahydro-cyclopropa[c]chromene-1-carboxylic acid (285 mg, 1.5 mmol) and triethylamine (209 μL, 1.5 mmol) in toluene (1.5 mL) at 20° C., was added diphenylphosphoryl azide (413 mg, 1.5 mmol). After 30 min at 20° C., the reaction mixture was heated to 120° C. for 15 min, where after a solution of 2-amino-5-cyano-pyridine (197 mg, 1.65 mmol) in DMF (1 mL) was added. After 3 h at 120° C., the reaction mixture was allowed to assume room temperature. The reaction mixture was concentrated under reduced pressure, benzene (20 mL) was added and the reaction mixture was washed with 1N HCl (30 mL), $H_2O$ (30 mL) and brine (30 mL). The solvent of the organic phases was removed under reduced pressure. The crude product was crystallized from EtOH/$CH_2Cl_2$, to give 133 mg (29%) of (±)-cis-1-(5-cyano-pyridin-2-yl)-3-(1,1a,2,7b-tetrahydro-cyclopropa[c]chromene-1-yl)-urea.

$^1$H-NMR (DMSO-$d_6$): 9.78 (s, 1H), 8.31 (d, 1H), 7.99 (dd, 1H), 7.83 (d, 1H), 7.43 (d, 1H), 7.27 (d, 1H), 7.09 (dd, 1H), 6.89 (dd, 1H), 6.80 (d, 1H), 4.25 (dd, 1H), 4.14 (dd, 1H), 3.43 (m, 1H), 2.35 (dd, 1H), 1.92 (m, 1H).

EXAMPLE 2

(±)-cis-1-(5-Cyano-pyridin-2-yl)-3-(1,1a,3,7b-tetrahydro-2-oxa-cyclopropa[a]naphthalen-1-yl)-urea a) (±)-cis-1,1a,3,7b-Tetrahydro-2-oxa-cyclopropa[a]naphthalene-1-carboxylic acid ethyl ester

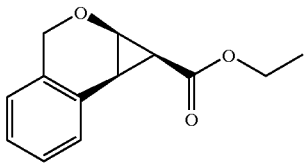

(±)-cis-1,1a,3,7b-Tetrahydro-2-oxa-cyclopropa[a]naphthalene-1-carboxylic acid ethyl ester was synthesized analogously to Example 1a from 1H-isochromene (3.57 g, 27 mmol), to give 910 mg (15%) of (±)-cis-1,1a,3,7b-tetrahydro-2-oxa-cyclopropa[a]naphthalene-1-carboxylic acid ethyl ester.

$^1$H-NMR (CDCl$_3$): 7.34 (d, 1H), 7.25 (dd, 1H), 7.18 (dd, 1H), 7.03 (d, 1H), 4.81 (d, 1H), 4.51 (d, 1H), 4.28 (dd, 1H), 3.95 (q, 2H), 2.43 (dd, 1H), 2.05 (dd, 1H), 1.04 (t, 3H).

b) (±)-cis-1,1a,3,7b-Tetrahydro-2-oxa-cyclopropa[a]naphthalene-1-carboxylic acid

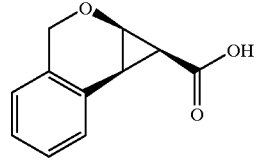

(±)-cis-1,1a,3,7b-Tetrahydro-2-oxa-cyclopropa[a]naphthalene-1-carboxylic acid was synthesized analogously to Example 1b from (±)-cis-1,1a,3,7b-tetrahydro-2-oxa-cyclopropa[a]naphthalene-1-carboxylic acid ethyl ester (436 mg, 2 mmol), to give 86 mg (22%) of (±)-cis-1,1a,3,7b-tetrahydro-2-oxa-cyclopropa[a]-naphthalene-1-carboxylic acid as a white solid. The crude product was column chromatographed (silica gel, 1→5% MeOH in $CH_2Cl_2$).

$^1$H-NMR (CDCl$_3$): 8.50 (br s, 1H), 7.39 (d, 1H), 7.30 (dd, 1H), 7.21 (dd, 1H), 7.07 (d, 1H), 4.87 (d, 1H), 4.57 (d, 1H), 4.38 (dd, 1H), 2.59 (dd, 1H), 2.15 (dd, 1H).

c) (±)-cis-1-(5-Cyano-pyridin-2-yl)-3-(1,1a,3,7b-tetrahydro-2-oxa-cyclopropa[a]naphthalen-1-yl)-urea

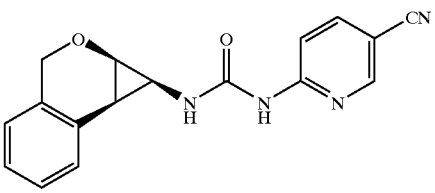

(±)-cis-1-(5-Cyano-pyridin-2-yl)-3-(1,1a,3,7b-tetrahydro-2-oxa-cyclopropa[a]naphthalen-1-yl)-urea was synthesized analogously to example 1c from (±)-cis-1,1a,3,7b-tetrahydro-2-oxa-cyclopropa[a]naphthalene-1-carboxylic acid (86 mg, 0.45 mmol). The crude product was column chromatographed (silica gel, 1→5% MeOH in $CH_2Cl_2$), to give 21 mg (15%) of (±)-cis-1-(5-cyano-pyridin-2-yl)-3-(1,1a,3,7b-tetrahydro-2-oxa-cyclopropa[a]naphthalen-1-yl)-urea.

$^1$H-NMR (DMSO-$d_6$): 9.62 (s, 1H), 8.29 (d, 1H), 7.98 (dd, 1H), 7.52–7.44 (m, 2H), 7.27–7.05 (m, 4H), 4.69 (d, 1H), 4.45 (d, 1H), 4.05 (dd, 1H), 3.25–3.10 (m, 1H), 2.22 (dd, 1H).

EXAMPLE 3

(±)-cis-1-(5-Cyano-pyridin-2-yl)-3-(7-hydroxy-6-propionyl-1,1a,2,7b-tetrahydro-cyclopropa[c]chromen-1-yl)-urea a) 1-(2-Hydroxy-4-prop-2-ynyloxy-phenyl)-propan-1-one

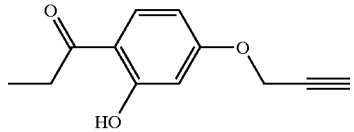

A mixture of 2',4'-dihydroxy-propiophenone (24.9 g, 0.15 mol), 3-bromo-propyne (24.2 g, 0.20 mol) and $K_2CO_3$ (20.7 g, 0.15 mol) in acetone (500 mL) was refluxed for 12 h. The reaction mixture was allowed assume room temperature and the precipitate was removed by filtration. The filtrate was concentrated under reduced pressure. The crude product was purified by column chromatography (silica gel, 0→2% MeOH in $H_2O$), to give 26.2 g (85%) of 1-(2-hydroxy-4-prop-2-ynyloxy-phenyl)-propan-1-one.

<sup>1</sup>H-NMR (CDCl₃): 12.80 (s, 1H), 7.69 (d, 1H), 6.52 (m, 2H), 4.72 (d, 2H), 2.96 (q, 2H), 2.56 (t, 1H), 1.23 (t, 3H).

3b) 1-(5-Hydroxy-2H-chromen-6-yl)-propan-1-one

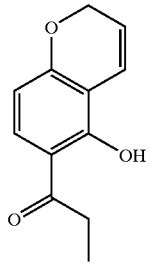

A mixture of 1-(2-hydroxy-4-prop-2-ynyloxy-phenyl)-propan-1-one (19.8 g, 97 mmol) and N,N-diethylaniline (100 mL) was heated to reflux for 3 h. The reaction mixture was concentrated under reduced pressure. The crude product was purified by column chromatography (silica gel, 5→10% EtOAc in Hexane) and thereafter recrystallized from EtOAc/Hexane, to give 8.91 g (45%) of 1-(5-hydroxy-2H-chromen-6-yl)-propan-1-one.

¹H-NMR (CDCl₃): 13.00 (s, 1H), 7.49 (d, 1H), 6.75 (dt, 1H), 6.27 (d, 1H), 5.67 (dt, 1H), 4.86 (dd, 2H), 2.90 (q, 2H), 1.19 (t, 3H).

3c) 7-Hydroxy-6-propionyl-1,1a,2,7b-tetrahydro-cyclopropa[c]chromene-1-carboxylic acid ethyl ester

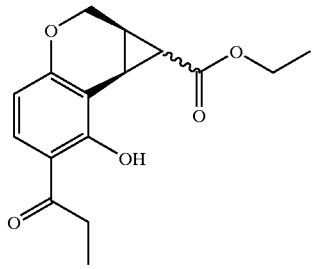

To a mixture of 1-(5-hydroxy-2H-chromen-6-yl)-propan-1-one (511 mg, 2.5 mmol) and (Rh(II)Ac₂)₂ (11 mg, 0.025 mmol) in 1,2-dichloroethane (8 mL) at 20° C., was added dropwise (3 h) a solution of ethyl diazoacetate (571 mg, 5 mmol) in 1,2-dichloroethane (2 mL). After 15 min at 20° C., the reaction mixture was washed with H₂O (10 mL). The H₂O phase was washed with CH₂Cl₂ (10 mL) and the solvent of the combined organic phases was removed under reduced pressure. The crude product was purified by column chromatography (silica gel, 1→5% MeOH in CH₂Cl₂), to give 300 mg (41%) of 7-hydroxy-6-propionyl-1,1a,2,7b-tetrahydro-cyclopropa[c]chromene-1-carboxylic acid ethyl ester (a 33/64 mixture of cis and trans isomers).

¹H-NMR (CDCl₃): 13.13–13.07 (m, 1H), 7.57–7.49 (m, 1H), 6.41–6.38 (m, 1H), 4.65–3.92 (m, 4H), 3.01–1.95 (m, 5H), 1.29–1.08 (m, 6H).

3d) (±)-cis-7-Hydroxy-6-propionyl-1,1a,2,7b-tetrahydro-cyclopropa[c]chromene-1-carboxylic acid

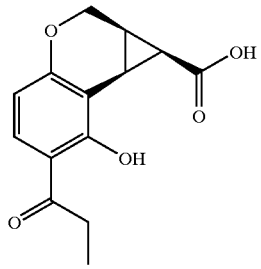

±cis-7-Hydroxy-6-propionyl-1,1a,2,7b-tetrahydro-cyclopropa[c]chromene-1-carboxylic acid was synthesized analogously to Example 2b from 7-hydroxy-6-propionyl-1,1a,2,7b-tetrahydro-cyclopropa[c]chromene-1-carboxylic acid ethyl ester (299 mg, 1.03 mmol, a 33/64 mixture of cis and trans isomers), to give 39.3 mg (15%) of (±)-cis-7-hydroxy-6-propionyl-1,1a,2,7b-tetrahydro-cyclopropa[c]chromene-1-carboxylic acid as a white solid and (±)-trans-7-hydroxy-6-propionyl-1,1a,2,7b-tetrahydro-cyclopropa[c]chromene-1-carboxylic acid as a byproduct. The crude product was purified by column chromatography (silica gel, 1→5% MeOH in CH₂Cl₂).

¹H-NMR (DMSO-d₆): 7.67 (d, 1H), 6.35 (d, 1H), 4.57 (dd, 1H), 4.36 (dd, 1H), 2.98 (q, 2H), 2.55–2.46 (m, 1H), 2.18–2.00 (m, 2H), 1.10 (t, 3H).

3e) (±)-cis-1-(5-Cyano-pyridin-2-yl)-3-(7-hydroxy-6-propionyl-1,1a,2,7b-tetrahydro-cyclopropa[c]chromen-1-yl)-urea

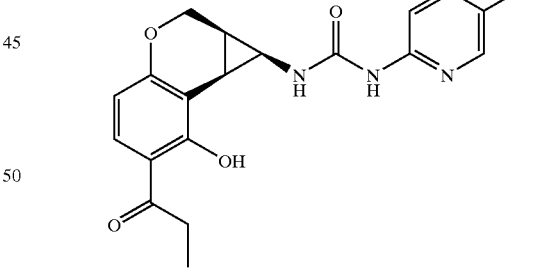

(±)-cis-1-(5-Cyano-pyridin-2-yl )-3-(7-hydroxy-6-propionyl-1,1a,2,7b-tetrahydro-cyclopropa[c]chromen-1-yl)-urea was synthesized analogously to Example 1c from ±cis-7-hydroxy-6-propionyl-1,1a,2,7b-tetrahydro-cyclopropa[c]chromene-1-carboxylic acid (39.3 mg, 0.15 mmol). The crude product was purified by HPLC (C₁₈, 5→95% acetonitrile in H₂O), to give 2.9 mg (5.1%) of (±)-cis-1-(5-cyano-pyridin-2-yl)-3-(7-hydroxy-6-propionyl-1,1a,2,7b-tetrahydro-cyclopropa[c]chromen-1-yl)-urea.

¹H-NMR (DMSO-d₆): 13.15 (s, 1H), 9.71 (s, 1H), 8.30 (d, 1H), 8.01 (dd, 1H), 7.73 (d, 1H), 7.57 (d, 1H), 7.50 (d, 1H), 6.43 (d, 1H), 4.42 (dd, 1H), 4.13 (dd, 1H), 3.45–3.32 (m, 1H), 3.01 (q, 2H), 2.49–2.42 (m, 1H), 1.97–1.86 (m, 1H), 1.12 (t, 3H).

EXAMPLE 4

±cis-1-(6-Acetyl-7-hydroxy-1,1a,2,7b-tetrahydro-cyclopropa[c]chromen-1-yl)-3-(5-cyano-pyridin-2-yl)-urea 4a) 1-(2-Hydroxy-4-prop-2-ynyloxy-phenyl)-ethanone

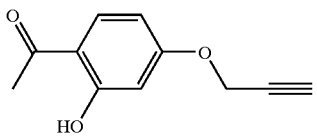

1-(2-Hydroxy-4-prop-2-ynyloxy-phenyl)-ethanone was synthesized analogously to Example 3a from 1-(2,4-dihydroxy-phenyl)-ethanone (20 g, 131 mmol), to give 22 g (88%) of 1-(2-hydroxy-4-prop-2-ynyloxy-phenyl)-ethanone.

¹H-NMR (CDCl₃): 12.70 (s, 1H), 7.66 (d, 1H), 6.52 (m, 2H), 4.72 (d, 2H), 2.58–2.55 (m, 4H).

4b) 1-(5-Hydroxy-2H-chromen-6-yl)-ethanone

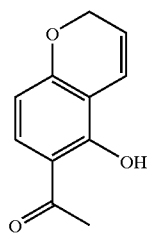

1-(5-Hydroxy-2H-chromen-6-yl)-ethanone was synthesized analogously to Example 3b from 1-(2-hydroxy-4-prop-2-ynyloxy-phenyl)-ethanone (17 g, 89 mmol), to give 6.0 g (35%) of 1-(5-hydroxy-2H-chromen-6-yl)-ethanone.

¹H-NMR (CDCl₃): 12.92 (s, 1H), 7.51 (d, 1H), 6.79 (dt, 1H), 6.32 (d, 1H), 5.71 (dt, 1H), 4.89 (dd, 2H), 2.55 (s, 3H).

4c) 6-Acetyl-7-hydroxy-1,1a,2,7b-tetrahydro-cyclopropa[c]chromene-1-carboxylic acid ethyl ester

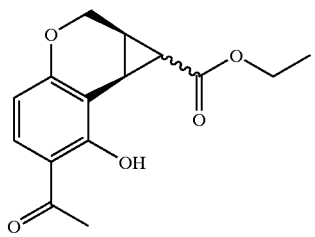

6-Acetyl-7-hydroxy-1,1a,2,7b-tetrahydro-cyclopropa[c]chromene-1-carboxylic acid ethyl ester (a 40/60 mixture of cis and trans isomers) was synthesized analogously to Example 3c from 1-(5-hydroxy-2H-chromen-6-yl)-ethanone.

¹H-NMR (CDCl₃): 13.05–12.97 (m, 1H), 7.54–7.47 (m, 1H), 6.43–6.33 (m, 1H), 4.63–3.94 (m, 4H), 3.02–1.96 (m, 6H), 1.31–1.08 (m, 3H).

4d) 6-Acetyl-7-hydroxy-1,1a,2,7b-tetrahydro-cyclopropa[c]chromene-1-carboxylic acid

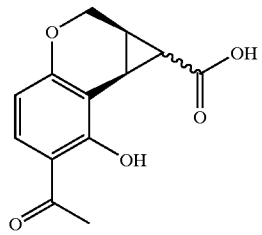

6-Acetyl-7-hydroxy-1,1a,2,7b-tetrahydro-cyclopropa[c]chromene-1-carboxylic acid was synthesized analogously to Example 1b from 6-acetyl-7-hydroxy-1,1a,2,7b-tetrahydro-cyclopropa[c]chromene-1-carboxylic acid ethyl ester (2 g, 8.1 mmol, a 40/60 mixture of cis and trans isomers), to give 300 mg (17%) of 6-acetyl-7-hydroxy-1,1a,2,7b-tetrahydro-cyclopropa[c]chromene-1-carboxylic acid (a 40/60 mixture of cis and trans isomers). The crude product was purified by column chromatography (silica gel, 1→5% MeOH in CH₂Cl₂)

¹H-NMR (CDCl₃): 7.55–7.45 (m, 1H), 6.45–6.30 (m, 1H), 4.65–4.00 (m, 2H), 3.05–1.95 (m, 6H).

4e) (±)-cis-1-(6-Acetyl-7-hydroxy-1,1a,2,7b-tetrahydro-cyclopropa[c]chromen-1-yl)-3-(5-cyano-pyridin-2-yl)-urea

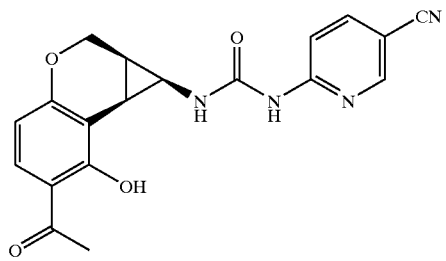

(±)-cis-1-(6-Acetyl-7-hydroxy-1,1a,2,7b-tetrahydro-cyclopropa[c]chromen-1-yl)-3-(5-cyano-pyridin-2-yl)-urea was synthesized analogously to Example 1c from 6-acetyl-7-hydroxy-1,1a,2,7b-tetrahydro-cyclopropa[c]chromene-1-carboxylic acid (300 mg, 1.21 mmol, a 40/60 mixture of cis and trans isomers). The crude product was purified by HPLC (C₁₈, 5→95% acetonitrile in H₂O), to give 7.7 mg (17%) of (±)-cis-1-(6-acetyl-7-hydroxy-1,1a,2,7b-tetrahydro-cyclopropa[c]chromen-1-yl)-3-(5-cyano-pyridin-2-yl)-urea and 9.0 mg (20%) of (±)-trans-1-(6-acetyl-7-hydroxy-1,1a,2,7b-tetrahydro-cyclopropa[c]chromen-1-yl)-3-(5-cyano-pyridin-2-yl)-urea as a byproduct.

¹H-NMR (CDCl₃+CD₃OD): 7.98 (d, 1H), 7.74 (dd, 1H), 7.60 (d, 1H), 7.01 (d, 1H), 6.40 (d, 1H), 4.43 (dd, 1H), 4.29 (dd, 1H), 3.57 (dd, 1H), 2.69 (m, 1H), 2.61 (s, 3H), 2.00–1.86 (m, 1H).

EXAMPLE 5

(±)-cis-1-(5-Cyanopyridin-2-yl)-3-(7-fluoro-4-propionyl-1,1a,2,7b-tetrahdro-cyclopropa[c]chromen-1-yl)-urea 5a) 1-(4-Fluoro-2-prop-2-ynyloxy-phenyl)-propan-1-one

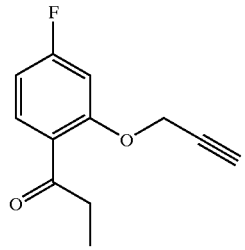

To a mixture of NaH (95%, 278 mg, 11 mmol) in DMF (20 mL) at 0° C., was added 1-(4-fluoro-2-hydroxy-phenyl)-propan-1-one (1.68 g, 10 mmol) in DMF (5 mL). After 15 min at 0° C., was 3-bromo-propyne (3.02 g, 20 mmol) added to the reaction mixture. After 1 h at 0° C., was the reaction mixture allowed to assume room temperature. The reaction mixture was extracted with $H_2O$ (100 mL). The $H_2O$ phase was washed with $Et_2O$ (3×100 mL) and the solvent of the combined organic phases was removed under reduced pressure. The crude product was purified by column chromatography (silica gel, $CH_2Cl_2$), to give 1.40 g (68%) of 1-(4-fluoro-2-prop-2-ynyloxy-phenyl)-propan-1-one.

$^1$H-NMR (CDCl$_3$): 7.64 (dd, 1H), 6.69 (dd, 1H), 6.60 (ddd, 1H), 4.68 (d, 2H), 2.85 (q, 2H), 2.58 (t, 1H), 1.03 (t, 3H).

5b) 1-(5-Fluoro-2H-chromen-8-yl)-propan-1-one

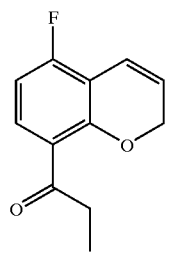

1-(5-Fluoro-2H-chromen-8-yl)-propan-1-one was synthesized analagously to Example 3b from 1-(4-fluoro-2-prop-2-ynyloxy-phenyl)-propan-1-one (1.34 g, 6.5 mmol), to give 619 mg (46%) of 1-(5-fluoro-2H-chromen-8-yl)-propan-1-one.

$^1$H-NMR (CDCl$_3$): 7.60 (dd, 1H), 6.67–6.58 (m, 2H), 5.86 (dt, 1H), 4.76 (dd, 2H), 2.93 (q, 2H), 1.23 (t, 3H).

5c) (±)-cis-7-Fluoro-4-propionyl-1,1a,2,7b-tetrahydro-cyclopropa[c]chromene-1-carboxylic acid ethyl ester

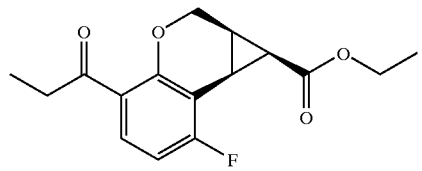

(±)-cis-7-Fluoro-4-propionyl-1,1a,2,7b-tetrahydro-cyclopropa[c]chromene-1-carboxylic acid ethyl ester was synthesized according to method 3c) from 1-(5-fluoro-2H-chromen-8-yl)-propan-1-one (619 mg, 3 mmol), to give 142 mg (16%) of (±)-cis-7-fluoro-4-propionyl-1,1a,2,7b-tetrahydro-cyclopropa[c]chromene-1-carboxylic acid ethyl ester and (±)-trans-7-fluoro-4-propionyl-1,1a,2,7b-tetrahydro-cyclopropa[c]chromene-1-carboxylic acid ethyl ester as a byproduct.

$^1$H-NMR (CDCl$_3$): 7.59 (dd, 1H), 6.65 (m, 1H), 4.50–4.46 (m, 2H), 3.95 (q, 2H); 2.89 (q, 2H), 2.57 (dd, 1H), 2.20 (dd, 1H), 1.13–1.03 (m, 1H), 1.12–1.01 (m, 6H).

5d) (±)-cis-7-Fluoro-4-propionyl-1,1a,2,7b-tetrahydro-cyclopropa[c]chromene-1-carboxylic acid.

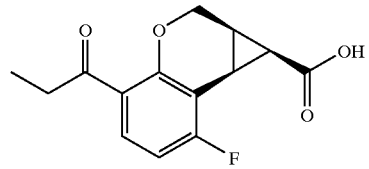

(±)-cis-7-Fluoro-4-propionyl-1,1a,2,7b-tetrahydro-cyclopropa[c]chromene-1-carboxylic acid was synthesized analogously to Example 1b from (±)-cis-7-fluoro-4-propionyl-1,1a,2,7b-tetrahydro-cyclopropa[c]chromene-1-carboxylic acid ethyl ester (140.3 mg, 0.48 mmol), to give 83 mg (65%) of (±)-cis-7-fluoro-4-propionyl-1,1a,2,7b-tetrahydro-cyclopropa[c]chromene-1-carboxylic acid as a white solid. The crude product was purified by column chromatography (silica gel, 1→5% MeOH in $CH_2Cl_2$).

$^1$H-NMR (DMSO-d$_6$): 12.15 (br s, 1H), 7.46 (dd, 1H), 6.78 (dd, 1H), 4.57 (dd, 1H), 4.43 (dd, 1H), 2.93–2.80 (m, 2H), 2.55 (dd, 1H), 2.24 (dd, 1H), 2.20–2.10 (m, 1H), 1.02 (t, 3H).

5e) (±)-cis-1-(5-Cyanopyridin-2-yl)-3-(7-fluoro-4-propionyl-1,1a,2,7b-tetrahydro-cyclopropa[c]chromen-1-yl)-urea

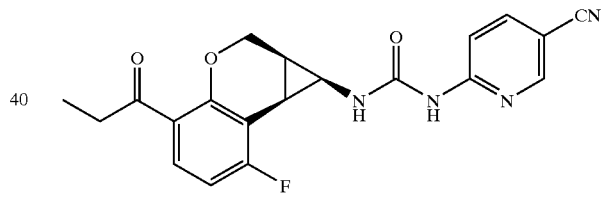

(±)-cis-1-(5-Cyanopyridin-2-yl)-3-(7-fluoro-4-propionyl-1,1a,2,7b-tetrahydro-cyclopropa[c]chromen-1-yl)-urea was synthesized analagously to Example 1c from (±)-cis-7-fluoro-4-propionyl-1,1a,2,7b-tetrahydro-cyclopropa[c]chromene-1-carboxylic acid (81.9 mg, 0.31 mmol). The crude product was purified by HPLC (C$_{18}$, 5→95% acetonitrile in H$_2$O), to give 12 mg (10%) of (±)-cis-1-(5-cyanopyridin-2-yl)-3-(7-fluoro-4-propionyl-1,1a,2,7b-tetrahydro-cyclopropa[c]chromen-1-yl)-urea.

$^1$H-NMR (DMSO-d$_6$): 9.81 (s, 1H), 8.33 (d, 1H), 8.04 (dd, 1H), 7.83 (br s, 1H), 7.49–7.40 (m, 2H), 6.89 (dd, 1H), 4.41 (dd, 1H), 4.34 (dd, 1H), 3.46–3.38 (m, 1H), 2.76 (q, 2H), 2.56–2.46 (m, 1H), 2.09–1.98 (m, 1H), 0.93 (t, 3H).

EXAMPLE 6

(±)cis-1-(5-Cyano-pyridin-2-yl)-3-(7-fluoro-4-methoxy-1,1a,2,7b-tetrahydro-cyclopropa[c]chromen-1-yl)-urea 6a) 6-Fluoro-2-hydroxy-3-methoxy-benzaldehyde 1M boron trichloride in dichloromethane (25 ml; 25 mmol) was added to a solution of 6-fluoro-2,3-dimethoxy-benzaldehyde [Cantrell, Amanda S.; Engelhardt, Per;

Hoegberg, Marita; Jaskunas, S. Richard; Johansson, Nils Gunnar; et al.; J.Med.Chem.; 39; 21; 1996; 4261–4274] (4.26 g; 23 mmol) in dichloromethane (30 ml) keeping the reaction temperature at −70 C. The reaction mixture stirred at room temperature overnight and hydrolyzed with water. The organic phase was separated, washed with water and evaporated in vacuo. The residue was chromatographed (silica gel, EA:Hex, 5:1) to give 3.72 g (94%) of 6-fluoro-2-hydroxy-3-methoxy-benzaldehyde as yellow crystals.

$^1$H-NMR (CDCl$_3$): 11.61 (s, 1H), 10.23 (s, 1H), 7.02 (dd, 1H), 6.55 (app. t, 1H), 3.87 (s, 3H).

6b) 5-Fluoro-8-methoxy-2H-chromene

6-Fluoro-2-hydroxy-3-methoxy-benzaldehyde (3.32 g, 19 mmol) was dissolved in acetonitrile (20 ml) and DBU (2.97 ml, 19 mmol) was added followed by vinyltriphenylphosphine bromide (7.2 g, 19 mmol). The reaction mixture was heated under reflux for 48 h, diluted with water and extracted with ether (3×50 ml). The organic phase was washed with water, 10% sodium hydroxide, water and brine and evaporated in vacuo. The residue was submitted to column chromatography (silica gel, EA:Hex, 1:20) yielding 1.2 g of 5-fluoro-8-methoxy-2H-chromene (34%).

$^1$H-NMR (CDCl$_3$): 6.65 (m, 2H), 6.54 (t, 1H), 5.83 (dt, 1H), 4.88 (dd, 2H), 3.83(s, 3H).

6c) (±)-cis-7-Fluoro-4-methoxy-1,1a,2,7b-tetrahydro-cyclopropa[c]chromene-1-carboxylic acid ethyl ester The title compound was synthesized analogously to example 3c from 5-fluoro-8-methoxy-2H-chromene.

$^1$H-NMR (CDCl$_3$): 6.7–6.5 (m, 2H), 4.48 (m, 2H), 3.99 (m, 2H), 3.80 (s, 3H), 2.57 (app.t, 1H), 2.20 (app.t, 1H), 2.05 (m, 1H), 1.08 (t, 3H).

6d) (±)-cis-7-Fluoro-4-methoxy-1,1a,2,7b-tetrahydro-cyclopropa[c]chromene-1-carboxylic acid The title compound was synthesized analogously to example 1b from (±)-cis-7-fluoro-4-methoxy-1,1a,2,7b-tetrahydro-cyclopropa[c]chromene-1-carboxylic acid ethyl ester.

$^1$H-NMR (CDCl$_3$): 6.7–6.5 (m, 2H), 4.48 (m, 2H), 3.80 (s, 3H), 2.61 (app. t, 1H), 2.17 (app. t, 1H), 2.06 (m, 1H).

6e) (±)-cis-1-(5-Cyano-pyridin-2-yl)-3-(7-fluoro-4-methoxy-1,1a,2,7b-tetrahydro-cyclopropa[c]chromen-1-yl)-urea.

The title compound was synthesized analogously to Example 1c from (±)-cis-7-fluoro-4-methoxy-1,1a,2,7b-tetrahydro-cyclopropa[c]chromene-1-carboxylic acid (62 mg, 0.17 mmol). Yield 38 mg (40%).

$^1$H-NMR (CDCl$_3$): 10.06 (br. s, 1H), 9.40 (br. d, 1H), 8.11 (d, 1H), 7.70 (dd, 1H), 6.91 (d, 1H), 6.68 (m, 2H), 4.48 (dd, 1H), 4.28 (dd, 1H), 3.90–3.72 (m, 4H), 2.64 (app. T, 1H), 1.96 (m, 1H).

EXAMPLE 7

(±)-cis-1-(5-Cyano-pyridin-2-yl)-3-(7-fluoro-4-chloro-1,1a,2,7b-tetrahydro-cyclopropa[c]chromen-1-yl)-urea 7a) 1-Chloro-4-fluoro-2-prop-2-ynyloxy-benzene The title compound was synthesized analogously to example 15a) from 2-chloro-5-fluorophenol (2.5 g). Yield 2.8 g (90%).

$^1$H-NMR (CDCl$_3$): 7.32 (dd, 1H), 6.85 (dd, 1H), 6.68 (m, 1H), 4.77 (d, 2H), 2.58 (t, 1H).

7b) 5-Fluoro-8-chloro-2H-chromene

The title compound was synthesized analogously to Example 15b) from 1-chloro-4-fluoro-2-prop-2-ynyloxy-benzene (2.8 g). Yield 0.97 g (35%).

$^1$H-NMR (CDCl$_3$): 7.09 (dd, 1H), 6.63 (dt, 1H), 6.56 (t, 1H), 5.84 (dt, 1H), 4.95 (dd, 2H).

7c) ±cis-7-Fluoro-4-chloro-1,1a,2,7b-tetrahydro-cyclopropa[c]chromene-1-carboxylic acid ethyl ester The title compound was synthesized analogously to Example 15c) from 5-Fluoro-8-chloro-2H-chromene.

$^1$H-NMR (CDCl$_3$): 7.14 (dd, 1H), 6.60 (t, 1H), 4.51 (m, 2H), 4.01 (m, 2H), 2.60(app. t, 1H), 2.23 (t, 1H), 2.09 (m, 1H), 1.08 (t, 3H).

7d) (±)-cis-7-Fluoro-4-chloro-1,1a,2,7b-tetrahydro-cyclopropa[c]chromene-1-carboxylic acid The title compound was synthesized analogously to example 15 d) from (±)-cis-7-fluoro-4-chloro-1,1a,2,7b-tetrahydro-cyclopropa[c]chromene-1-carboxylic acid ethyl ester 850 mg). Yield 43 mg (96%).

$^1$H-NMR (CDCl$_3$): 8.86 (br. s, 1H), 7.13 (dd, 1H), 6.59 (t, 1H), 4.50 (m, 2H), 2.63 (t, 1H), 2.23–2.05 (m, 2H).

7e) ±cis-1-(5-Cyano-pyridin-2-yl)-3-(7-fluoro-4-chloro-1,1a,2,7b-tetrahydro-cyclopropa[c]chromen-1-yl)-urea The title compound was synthesized analogously to example 1c from (±)-cis-7-fluoro-4-chloro-1,1a,2,7b-tetrahydro-cyclopropa[c]chromene-1-carboxylic acid (63 mg). Yield 52 mg (56%).

$^1$H-NMR (CDCl$_3$): 9.79 (br. s, 1H), 9.34 (br. s, 1H), 8.22 (d, 1H), 7.72 (dd, 1H), 7.17 (dd, 1H), 6.87 (d, 1H), 6.67 (t, 1H), 4.54(dd, 1H), 4.33 (dd, 1H), 3.84 (app. q, 1H), 2.68 (dd, 1H), 2.00 (m, 1H).

EXAMPLE 8

±cis-1-(5-Chloro-pyridin-2-yl)-3-(4-chloro-7-fluoro-1,1a2,7b-tetrahydro-cyclopropa[c]chromene-1-yl)-urea ±cis-1-(5-Chloro-pyridin-2-yl)-3-(4-chloro-7-fluoro-1,1a,2,7b-tetrahydro-cyclopropa[c]chromene-1-yl)-urea (15 mg, 24%) was prepared according to the procedure described in example 1c, from ±cis-(4-chloro-7-fluoro-1,1a,2,7b-tetrahydro-cyclopropa[c]chromene)-1-carboxylic acid (40 mg, 0.16 mmol) and 2-amino-5-chloropyridine (76 mg, 0.57 mmol).

$^1$H NMR (400 MHz, CDCl$_3$) δ ppm: 9.29 (brs, 1H), 9.26 (brs 1H), 7.84 (d, 1H), 7.47 (dd, 1H), 7.16 (dd, 1H), 6.76 (d, 1H), 6.67 (dd, 1H), 4.65 (dd, 1H), 4.34 (dd, 1H), 3.82 (dd, 1H), 2.62 (dd, 1H), 1.96 (m, 1H)

EXAMPLE 9

±cis-1-(5-Bromo-pyridin-2-yl)-3-(4-chloro-7-fluoro-1,1a,2,7b-tetrahydro-cyclopropa[c]chromene-1-yl)-urea ±cis-1-(5-Bromo-pyridin-2-yl)-3-(4-chloro-7-fluoro-1,1a,2,7b-tetrahydro-cyclopropa[c]chromene-1-yl)-urea (13 mg, 19%) was prepared according to the procedure described in example 1c, from ±cis-(4-chloro-7-fluoro-1,1a,2,7b-tetrahydro-cyclopropa[c]chromene)-1-carboxylic acid (40 mg, 0.16 mmol) and 2-amino-5-bromopyridine (99 mg, 0.57 mmol).

$^1$H NMR (400 MHz, CDCl$_3$) δ ppm: 9.27 (brs, 1H), 9.02 (brs, 1H), 7.95 (d, 1H), 7.60 (dd, 1H), 7.16 (dd, 1H), 6.70 (d, 1H), 6.67 (dd, 1H), 4.50 (dd, 1H), 4.35 (dd, 1H), 3.81 (dd, 1H), 2.63 (dd, 1H), 1.97 (m, 1H)

EXAMPLE 10

±cis-1-(5-Cyano-pyridin-2-yl)-3-(5-cyano-1,1a,2,7b-tetrahydro-cyclopropa[c]chromen-1-yl)-urea 10a) Trifluoro-methanesulfonic acid 4-formyl-3-hydroxy-phenyl ester A solution of triflic anhydride (1.77 ml, 10.5 mmol) in dichloromethane 10 ml) was added to a mixture of 2,4-dihydroxybenzaldehyde (1.38 g, 10 mmol) and pyridine (0.85 ml, 10.5 mmol) in dichloromethane (30 ml) at −70 C. Dry ice bath was removed and the reaction mixture was stirred for 2 h at room temperature. The reaction mixture was diluted with dichloromethane, washed with water, brine and evaporated in vacuo. The crude product was purified by column chromatography (silica gel, EA:Hex, 1:6) to give 1.55 g of trifluoro-methanesulfonic acid 4-formyl-3-hydroxy-phenyl ester (57%).

$^1$H-NMR (CDCl$_3$): 11.28 (s, 1H), 9.93 (s, 1H), 7.67 (d, 1H), 6.95 (m, 2H).

10b) Trifluoro-methanesulfonic acid 3-allyloxy-4-formyl-phenyl ester

Potassium carbonate (1.6 g, 11.5 mmol) and allyl bromide (1 ml, 11.5 mmol) were added to a solution of trifluoro-methanesulfonic acid 4-formyl-3-hydroxy-phenyl ester (1.55 g, 5.7 mmol) in acetone (50 ml). The reaction mixture was stirred at 55 C for 2 h, filtered and evaporated in vacuo. The residue was chromatographed (silica gel, EA:Hex, 1:20) to give 1.3 g (73%) of trifluoro-methanesulfonic acid 3-allyloxy-4-formyl-phenyl ester.

$^1$H-NMR (CDCl$_3$): 10.47 (s, 1H), 7.93 (d, 1H), 6.95 (d, 1H), 6.90 (s, 1H), 6.05 (m, 1H), 5.47 (d, 1H), 5.40 (d, 1H), 4.69 (d, 2H).

10c) Trifluoro-methanesulfonic acid 3-allyloxy-4-vinyl-phenyl ester

Methyltriphenylphosphonium bromide (1.95 g, 5.45 mmol) was added to a suspension of sodium hydride (60% in oil) (0.25 g, 6.3 mmol) in THF (35 ml) at 0 C and it was stirred for 30 min at room temperature. To the above solution was added solution of trifluoro-methanesulfonic acid 3-allyloxy-4-formyl-phenyl ester (1.3 g, 4.2 mmol) in THF (15 ml), and the reaction mixture was stirred for 2 h at room temperature. The reaction mixture was diluted with hexane and extracted with water. Organic phase was washed with brine and evaporated. Silica gel column chromatography (EA:Hex, 1:20) afforded trifluoro-methanesulfonic acid 3-allyloxy-4-vinyl-phenyl ester (0.68 g, 53%).

$^1$H-NMR (CDCl$_3$): 7.51 (d, 1H), 7.02 (dd, 1H), 6.85 (dd, 1H), 6.77 (d, 1H), 6.05 (m, 1H), 5.76 (dd, 1H), 5.43(m, 1H), 5.32 (m, 2H), 4.58 (dt, 2H).

10d) Trifluoro-methanesulfonic acid 2H-chromen-7-yl ester

To a solution of trifluoro-methanesulfonic acid 3-allyloxy-4-vinyl-phenyl ester (0.68 g, 2.2 mmol) in dichloromethane (5 ml) was added Ru-catalyst (Grubb's catalyst) (36 mg, 2 mol %), and the reaction mixture was stirred for 2 h at room temperature. After that period the reaction was complete (GC) and the reaction mixture was used in the next step without any work-up. Analytical sample was obtained after removal of the solvent by silica gel column chromatography (EA:Hex, 1:20).

$^1$H-NMR (CDCl$_3$): 6.97 (d, 1H), 6.76 (dd, 1H), 6.68 (d, 1H), 6.39 (dt, 1H), 5.81 (dt, 1H), 4.98(dd, 2H).

10e) ±cis-5-Trifluoromethanesulfonyloxy-1,1a,2,7b-tetrahydro-cyclopropa[c]chromene-1-carboxylic acid ethyl ester Rh(OAc)$_2$ (19 mg, 2 mol %) was added to the above solution (10d) and the solution of EDA (0.44 ml, 4.4 mmol) in 1 ml of dichloromethane was added with a syringe pump over 5 h at room temperature. When the reaction was complete (GC) dichloromethane was evaporated, the residue was dissolved in ethyl acetate and washed with saturated ammonium chloride solution and brine. Organic phase was evaporated and crude mixture of cis- and trans-isomers (1:1.3) was separated by column chromatography (silica gel, EA:Hex, 1:6) to give 0.4 g (50%) of ±cis-5-trifluoromethanesulfonyloxy-1,1a,2,7b-tetrahydro-cyclopropa[c]chromene-1-carboxylic acid ethyl ester.

$^1$H-NMR (CDCl$_3$): 7.29 (d, 1H), 6.82 (dd, 1H), 6.73 (d, 1H), 4.51 (dd, 1H), 4.29 (dd, 1H), 3.98 (m, 2H), 2.45 (t, 1H), 2.19 (t, 1H), 2.05 (m, 1H), 1.03 (t, 3H).

10f) ±cis-5-Cyano-1,1a,2,7b-tetrahydro-cyclopropa[c]chromene-1-carboxylic acid ethyl ester ±cis-5-Trifluoromethanesulfonyloxy-1,1a,2,7b-tetrahydro-cyclopropa[c]chromene-1-carboxylic acid ethyl ester (154 mg, 0.42 mmol), Pd(OAc)$_2$ (9 mg, 10 mol %) and PPh$_3$ (44 mg, 40 mol %) were mixed in DMF (4 ml) and gentle stream of nitrogen passed through reaction mixture for 10 min. Zn(CN)$_2$ (74 mg, 0.63 mmol) was added, vial was sealed and the reaction mixture was stirred at 120 C overnight. The reaction mixture was diluted with ethyl acetate and extracted with saturated ammonium chloride. Organic phase was evaporated and residue chromatographed (silica gel, EA:Hex 1:5) to give 53 mg (52%) of ±cis-5-cyano-1,1a,2,7b-tetrahydro-cyclopropa[c]chromene-1-carboxylic acid ethyl ester.

$^1$H-NMR (CDCl$_3$): 7.33 (d, 1H), 7.19 (dd, 1H), 7.05 (d, 1H), 4.50 (dd, 1H), 4.25 (dd, 1H), 3.99 (q, 2H), 2.46 (t, 1H), 2.25 (t, 1H), 2.11 (m, 1H), 1.06 (t, 3H).

10g) ±cis-5-Cyano-1,1a,2,7b-tetrahydro-cyclopropa[c]chromene-1-carboxylic acid

±cis-5-Cyano-1,1a,2,7b-tetrahydro-cyclopropa[c]chromene-1-carboxylic acid ethyl ester (53 mg, 0.22 mmol) and NaOH (35 mg, 0.88 mmol) were dissolved in mixture methanol water (1:1) (5 ml). Reaction mixture was stirred at 60 C for 30 min. Methanol was evaporated in vacuo and 20 ml of water was added. Resulting solution was extracted with ether. Water phase was concentrated, acidified with 1M HCl to pH~2 and extracted with ether. The organic phase was washed with brine and evaporated to give 42 mg (90%) of ±cis-5-cyano-1,1a,2,7b-tetrahydro-cyclopropa[c]chromene-1-carboxylic acid.

$^1$H-NMR (CDCl$_3$): 7.33 (d, 1H), 7.19 (dd, 1H), 7.06 (d, 1H), 4.51 (dd, 1H), 4.31 (dd, 1H), 2.53 (app. t, 1H), 2.27 (app. t, 1H), 2.16 (m, 1H).

10h) ±cis-1-(5-Cyano-pyridin-2-yl)-3-(5-cyano-1,1a,2,7b-tetrahydro-cyclopropa[c]chromen-1-yl)-urea ±cis-5-Cyano-1,1a,2,7b-tetrahydro-cyclopropa[c]chromene-1-carboxylic acid (42 mg, 0.19 mmol) and TEA (0.032 ml, 0.21 mmol) were dissolved in 3 ml of toluene. DPPA (0.046 ml, 0.21 mmol) and 2-amino-5-cyano-pirydine (25 mg, 0.21 mmol) were added. The reaction mixture was heated under reflux with stirring for 3 h. The resulting precipitate was filtered and washed with hot ethanol (3 ml) yielding 41 mg (63%) of ±cis-1-(5-cyano-pyridin-2-yl)-3-(5-cyano-1,1a,2,7b-tetrahydro-cyclopropa[c]chromen-1-yl)-urea.

$^1$H-NMR (DMSO-d$_6$): 9.86 (s, 1H), 8.48 (d, 1H), 8.07 (dd, 1H), 7.97 (br. s, 1H), 7.51 (d, 1H), 7.43 (d, 1H), 7.37 (d, 1H), 7.34 (dd, 1H), 4.39 (dd, 1H),4.19 (dd, 1H), 3.57 (app. q, 1H), 2.54 (app. t, 1H), 2.09 (m, 1H).

EXAMPLE 11

±cis-1-(5-Cyano-pyridin-2-yl)-3-(5-ethynyl-1,1a,2,7b-tetrahydro-cyclopropa[c]chromen-1-yl)-urea 11a) ±cis-5-Trimethylsilanylethynyl-1,1a,2,7b-tetrahydro-cyclopropa[c]chromene-1-carboxylic acid ethyl ester ±cis-5-Trifluoromethanesulfonyloxy-1,1a,2,7b-tetrahydro-cyclopropa[c]chromene-1-carboxylic acid ethyl ester (152 mg, 0.41 mmol), DPPP (38 mg, 20 mol %), Pd(dba)$_2$ (24 mg, 10 mol %), CuI (3 mg, 4 mol %) were mixed in 3 ml of triethylamine and gentle stream of nitrogen passed through reaction mixture for 10 min. Trimethylsilylacetylene (0.088 ml, 0.62 mmol) was added, vial was sealed and the reaction mixture was stirred at 120 C overnight. The reaction mixture was diluted with ethyl acetate, washed with water, brine and evaporated. The residue was purified by silica gel column chromatography (EA:Hex, 1:15) to give 0.1 g (77%) of ±cis-5-trimethylsilanylethynyl-1,1a,2,7b-tetrahydro-cyclopropa[c]chromene-1-carboxylic acid ethyl ester.

$^1$H-NMR (CDCl$_3$): 7.15 (d, 1H), 7.01 (dd, 1H), 6.88 (d, 1H), 4.47 (dd, 1H), 4.16 (dd, 1H), 3.96 (q, 2H), 2.38 (t, 1H), 2.13 (t, 1H), 2.01 (m, 1H), 1.04 (t, 3H), 0.22 (s, 9H).

11b) ±cis-5-Ethynyl-1,1a,2,7b-tetrahydro-cyclopropa[c]chromene-1-carboxylic acid ±cis-5-Trimethylsilanylethynyl-1,1a,2,7b-tetrahydro-cyclopropa[c]chromene-1-carboxylic acid ethyl ester (0.1 g, 0.32 mmol) and sodium hydroxide (0.076 g, 1.9 mmol) were dissolved in mixture of methanol:water (1:1) (5 ml). The reaction mixture was heated at 60 C for 5 h, then it was acidified with 1M HCl to pH~2 and extracted with ether. The organic phase was washed with brine and evaporated to give 66 mg (97%) of) ±cis-5-ethynyl-1,1a,2,7b-tetrahydro-cyclopropa[c]chromene-1-carboxylic acid.

$^1$H-NMR (CDCl$_3$): 7.17 (d, 1H), 7.03 (dd, 1H), 6.91 (d, 1H), 4.45 (dd, 1H), 4.23 (dd, 1H), 3.02 (s, 1H), 2.46 (t, 1H), 2.13 (t, 1H), 2.07 (m, 1H).

11c) ±cis-1-(5-Cyano-pyridin-2-yl)-3-(5-ethynyl-1,1a,2,7b-tetrahydro-cyclopropa[c]chromen-1-yl)-urea The title compound was synthesized analogously to example 10 h from ±cis-5-ethynyl-1,1a,2,7b-tetrahydro-cyclopropa[c]chromene-1-carboxylic acid (66 mg, 31 mmol). Yield 53 mg (52%).

$^1$H-NMR (DMSO-d$_6$): 9.88 (s, 1H), 8.41 (d, 1H), 8.06 (dd, 1H), 7.86 (br. s, 1H), 7.46 (d, 1H), 7.32 (d, 1H), 7.02 (dd, 1H), 6.93 (d, 1H), 4.31 (dd, 1H), 4.16 (dd, 1H), 4.12 (s, 1H), 3.47 (q, 1H), 2.43 (app. t, 1H), 2.00 (m, 1H).

EXAMPLE 12

±cis-1-(5-Acetyl-1,1a,2,7b-tetrahydro-cyclopropa[c]chromen-1-yl)-3-(5-cyano-pyridin-2-yl)-urea 12a) ±cis-5-Acetyl-1,1a,2,7b-tetrahydro-cyclopropa[c]chromene-1-carboxylic acid ethyl ester ±cis-5-Trifluoromethanesulfonyloxy-1,1a,2,7b-tetrahydro-cyclopropa[c]chromene-1-carboxylic acid ethyl ester (117 mg, 0.32 mmol), DPPP (7.3 mg, 50 mol %), Pd(OAc)$_2$ (2 mg, 25 mol %) and triethyl amine (0.09 ml, 0.64 mmol) were mixed in DMF (3 ml) and gentle stream of nitrogen passed through reaction mixture for 10 min. Butyl vinyl ether (0.21 ml, 1.6 mmol) was added, vial was sealed and the reaction mixture was stirred at 100 C for 2 h. 5% HCl (5 ml) was added and the reaction mixture was stirred at room temperature for 30 min. Resulting mixture was extracted with ethyl acetate. The organic phase was washed with saturated ammonium chloride and evaporated. The residue was purified by silica gel column chromatography (EA:Hex, 1:5) to give 76 mg (91%) of ±cis-5-acetyl-1,1a,2,7b-tetrahydro-cyclopropa[c]chromene-1-carboxylic acid ethyl ester.

$^1$H-NMR (CDCl$_3$):7.52 (dd, 1H), 7.36 (d, 1H), 7.34 (d, 1H), 4.51 (dd, 1H), 4.21 (dd, 1H), 3.98 (q, 2H), 2.53 (s, 3H), 2.47 (t, 1H), 2.23 (t, 1H), 2.08 (m, 1H), 1.05 (t, 3H).

12b) ±cis-5-Acetyl-1,1a,2,7b-tetrahydro-cyclopropa[c]chromene-1-carboxylic acid

The title compound was synthesized analogously to example 10 g from ±cis-5-acetyl-1,1a,2,7b-tetrahydro-cyclopropa[c]chromene-1-carboxylic acid ethyl ester (76 mg, 29 mmol). Yield 66 mg (97%).

$^1$H-NMR (CDCl$_3$): 7.52 (dd, 1H), 7.37 (d, 1H), 7.34 (d, 1H), 4.52 (dd, 1H), 4.26 (dd, 1H), 2.55 (s, 3H), 2.53 (t, 1H), 2.25 (t, 1H), 2.13 (m, 1H).

12c) ±cis-1-(5-Cyano-pyridin-2-yl)-3-(5-acetyl-1,1a,2,7b-tetrahydro-cyclopropa[c]chromen-1-yl)-urea The title compound was synthesized analogously to example 10 h from ±cis-5-acetyl-1,1a,2,7b-tetrahydro-cyclopropa[c]chromene-1-carboxylic acid (66 mg, 28 mmol). Yield 58 mg (59%).

$^1$H-NMR (DMSO-d$_6$): 9.87 (s, 1H), 8.42 (d, 1H), 8.05 (dd, 1H), 7.88 (br. s, 1H), 7.52 (dd, 1H), 7.49–7.44 (m, 2H), 7.37 (d, 1H), 4.39 (dd, 1H), 4.18 (dd, 1H), 3.55 (q, 1H), 2.55–2.50 (m, 4H, superimposed on residual DMSO-d$_6$ peak), 2.07 (m, 1H).

EXAMPLE 13

±cis-1-(5-Methoxy-1,1a,2,7b-tetrahydro-cyclopropa[c]chromen-1-yl)-3-(5-cyano-pyridin-2-yl)-urea The title compound was synthesized analogously to example 10 from 2-hydroxy-4-methoxybenzaldehyde.

$^1$H-NMR (CDCl$_3$): 8.44 (br. s, 1H), 8.06 (d, 1H), 7.70 (dd, 1H), 7.18 (d, 1H), 6.82 (br. d, 1H), 6.55 (dd, 1H), 6.36 (d, 1H), 4.32 (dd, 1H), 4.24 (dd, 1H), 3.76 (s, 3H), 3.58 (q, 1H), 2.36 (dd, 1H), 1.86 (m, 1H).

EXAMPLE 14

±cis-1-(5-Cyano-pyridin-2-yl)-3-(N-acetyl-1,1a,3,7b-tetrahydro-2-oxa-cyclopropa[a]quinoline-1-yl))-urea a) N-Acetyl-1,2-dihydroquinoline Quinoline (19.37 g, 150 mmol) was dissolved in anhydrous diethyl ether (500 ml) and cooled to 0° C. under inert atmosphere. DIBAL, 1.5 M in toluene (100 ml, 150 mmol) was added dropwise over 2 hrs and the reaction mixture was stirred at 0° C. for 30 min. Acetic anhydride (500 ml) was added dropwise over 30 min and the reaction mixture was stirred at 0° C. for 30 min. H$_2$O was added cautiously. The reaction mixture was extracted with diethyl ether and concentrated to give N-acetyl-1,2-dihydroquinoline (11.5 g, 44%).

b) ±cis-(N-acetyl-1,1a,2,7b-tetrahydro-cyclopropa[c]quinoline)-1-carboxylic acid ethyl ester ±cis-(N-acetyl-1,1a,2,7b-tetrahydro-cyclopropa[c]quinoline)-1-carboxylic acid ethyl ester was prepared according to the procedure described in example 1a, from N-acetyl-1,2-dihydroquinoline (10 g, 58 mmol) The product was purified by column chromatography on silica (EtOAc/hexane 5%→50%) to give ±cis-(N-acetyl-1,1a,2,7b-tetrahydro-cyclopropa[c]quinoline)-1-carboxylic acid ethyl ester (2.0 g, 13%).

c) ±cis-(N-Acetyl-1,1a,2,7b-tetrahydro-cyclopropa[c]quinoline)-1-carboxylic acid ±cis-(N-Acetyl-1,1a,2,7b-tetrahydro-cyclopropa[c]quinoline)-1-carboxylic acid (425 mg, 24%) was prepared according to the procedure described in example 1b, from ±cis-(N-acetyl-1,1a,2,7b-tetrahydro-cyclopropa[c]quinoline)-1-carboxylic acid ethyl ester (2.0 mg, 7.7 mmol).

d) ±cis-1-(5-Cyano-pyridin-2-yl)-3-(N-acetyl-1,1a,3,7b-tetrahydro-2-oxa-cyclopropa[a]quinoline-1-yl))-urea ±cis-1-(5-Cyano-pyridin-2-yl)-3-(N-acetyl-1,1a,3,7b-tetrahydro-2-oxa-cyclopropa[a]quinoline-1-yl))-urea (250 mg, 40%) was prepared according to the procedure described in example 1c, from ±cis-(N-acetyl-1,1a,2,7b-tetrahydro-cyclopropa[a]quinoline)-1-carboxylic acid (416 mg, 1.8 mmol).

$^1$H NMR (250 MHz, DMSO-d6) δ ppm: 9.51 (brs, 1H), 8.30 (d 1H), 8.01 (dd, 1H), 7.54 (dd, 1H), 7.44, (dd, 1H), 7.36 (d, 1H), 7.23–7.18 (m, 3H), 4.10 (d, 1H), 3.60 (dd, 1H), 3.12–3.05 (m, 1H), 2.37 (tr, 1H), 2.0–1.92 (m, 4H)

EXAMPLE 15

+/−-cis-1-(5-Cyanopyridin-2-yl)-3-(4,7-difluoro-1,1a,2,7b-tetrahydro-cyclopropa[c]chromen-1-yl)-urea

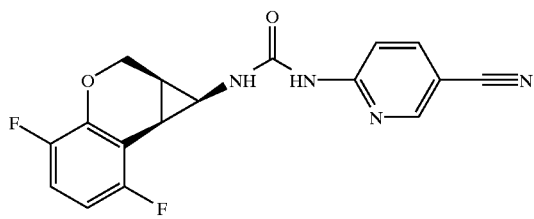

15a) 2,4-Difluoro-2-propynyloxybenzene

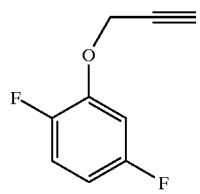

Commercially available 2,5-difluorophenol (20 g, 0.15 mol), K$_2$CO$_3$ (53 g, 0.38 mol) and commercially available 3-bromopropyne (45 g, 0.38 mol) were dissolved in acetone (300 ml), refluxed over night, cooled and filtrated. The solvent was removed and the crude product, dissolved in ether and washed with water and brine. The organic phase was evaporated and the crude product was re-dissolved in a small amount of ether and filtrated through a column of basic Al$_2$O$_3$. Evaporation and drying gave 20 g (80%) of 2,4-difluoro-2-prop-ynyloxy-benzene 15b) 5,8-Difluoro-2H-chromene

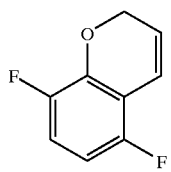

2,4-Difluoro-2-propynyloxybenzene (20 g, 0.12 mol) was dissolved in N,N,-diethyl aniline (100 ml) and heated under argon atmosphere at 225 deg. Celcius with an oil-bath for 6–8 h. Ether (150 ml) was added and the aniline was removed by extraction using 2 M HCl$_{(aq)}$. Purification by chromatography (silica gel, n-hexane) gave 5,8-difluoro-2H-chromene 5.8 g (29%)

15c) +/−cis-4,7-Difluoro-1,1a,2,7b-tetrahydro-cyclopropa[c]chromene-1-carboxylic acid ethyl ester

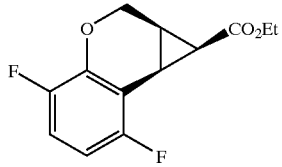

5,8-Difluoro-2H-chromene (5 g, 0.03 mol), (Rh(II)Ac$_2$)$_2$ (0.39 g, 0.00089 mol) was dissolved in 1,2-dichloroethane (60 ml) or ethanol-free chloroform. Ethyl diazoacetate (9.4 ml, 0089 mol) in the same solvent was added dropwise over a period of approximately 5 h under N$_2$ atmosphere. The solvent was then removed under vacuum and the mixture was taken upp in ethyl acetate, washed with NaHCO$_3$(aq), water and brine and the solvent removed. The product (33% cis, 66% trans) was purified by hromatography (0→10% ethyl acetate in n-hexane) to give 2.2 g of the title compound (30%).

15d) cis-4,7-Difluoro-1,1a,2,7b-tetrahydro-cyclopropa[c]chromene-1-carboxylic acid

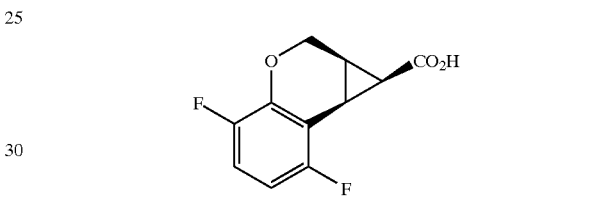

Cis-4,7-Difluoro-1,1a,2,7b-tetrahydro-cyclopropa[c]chromene-1-carboxylic acid ethyl ester (2 g, 0.008 mol) was heated in 1M LiOH in methanol-water (25%) at 80 deg. for 2 h. The volume was reduced to half and acidified. Extraction with ether followed by chromatography (silica gel, ether) gave pure title compound (35%)

e) (/−)cis-1-(5-Cyano-pyridin-2-yl)-3-(4,7-difluoro-1,1a,2,7b-tetrahydro-cyclopropa[c]chromen-1-yl)-urea

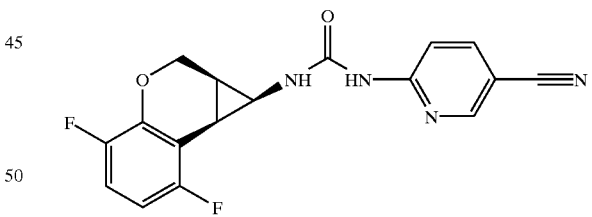

(+/−)-cis-1-(5-Cyano-pyridin-2-yl)-3-(4,7-difluoro-1,1a,2,7b-tetrahydro-cyclopropa[c]chromen-1-yl)-urea was prepared analogously to Example 1c but using cis-4,7-difluoro-1,1a,2,7b-tetrahydro-cyclopropa[c]chromene-1-carboxylic acid (0.2 g, 0.00088 mol) to give 0.130 g (42%) of pure title compound. The crude product was purified by extraction between 0.01 M HCl (aq) and ethyl acetate and chromatography (silica gel, 0→1% MeOH in Ether). The solvent was evaporated and the solid washed with a cold solution of 50% aceton in n-hexane.

$^1$H-NMR (CDCl$_3$—MeOD): 8.16 (d, 1H), 7.72 (dd, 1H), 6.97–6.86 (m, 2H), 6.69–6.61 (m, 1H), 4.47 (dd, 1H), 4.31 (dd, 1H), 3.75 (m, 1H), 2.65 (t, 1H), 2.05–1.96 (m, 1H).

EXAMPLE 16

(+/−)-cis-1-(5-Cyano-3-methyl-pyridin-2-yl)-3-(4,7-difluoro-1,1a,2,7b-tetrahydro-cyclopropa[c]chromen-1-yl)-urea

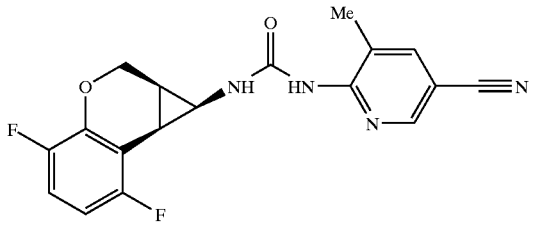

(+/−)-cis-1-(5-Cyano-3-methyl-pyridin-2-yl)-3-(4,7-difluoro-1,1a,2,7b-tetrahydro-cyclopropa[c]chromen-1-yl)-urea was prepared analogously to Example 1c but using cis-4,7-Difluoro-1,1a,2,7b-tetrahydro-cyclopropa[c]chromene-1-carboxylic acid (168 mg, 0.74 mmol) and 6-amino-5-methyl-nicotinonitrile (109 mg, 0.82 mmol) to give (+/−)-cis-1-(5-cyano-3-methyl-pyridin-2-yl)-3-(4,7-difluoro-1,1a,2,7b-tetrahydro-cyclopropa[c]chromen-1-yl)-urea 52 mg of(20%). The crude product was purified by extraction between 0.01 M HCl (aq) and ethyl acetate and chromatography (silica gel, 0→25% MeOH in Ether). The solvent was evaporated and the solid washed with 25% aceton in n-hexane.

$^1$H NMR (CDCl3-MeOD): 8.02 (d, 1H), 7.61 (dd, 1H), 6.97–6.87 (m, 1H, 6.70–6.62 (m, 1H), 4.48 (dd, 1H), 4.30 (dd, 1H), 3.78 (t, 1H), 3.37 (s, 3H), 2.66 (t, 1H), 2.03 (m, 1H).

EXAMPLE 17

+/−-cis-1-(5-Chloro-pyridin-2-yl)-3-(4,7-difluoro-1,1a,2,7b-tetrahydro-cyclopropa[c]chromen-1-yl)-urea

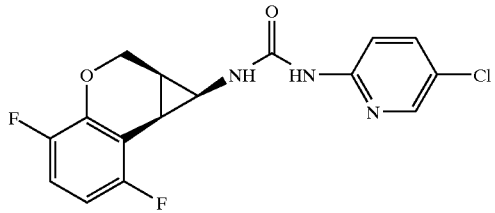

+/−-cis-1-(5-Chloro-pyridin-2-yl)-3-(4,7-difluoro-1,1a,2,7b-tetrahydro-cyclopropa[c]chromen-1-yl)-urea was prepared analogously to Example 1c but using cis-4,7-difluoro-1,1a,2,7b-tetrahydro-cyclopropa[c]chromene-1-carboxylic acid (90 mg, 0.4 mmol) and 6-amino-5-chloropyridine (51 mg, 0.44 mmol) to give +/−-cis-1-(5-chloro-pyridin-2-yl)-3-(4,7-difluoro-1,1a,2,7b-tetrahydro-cyclopropa[c]chromen-1-yl)-urea (50 mg, 35%). The crude product was purified by extraction between 0.01 M HCl (aq) and ethyl acetate-ether (1:1) and chromatography (silica gel, ether).

$^1$H NMR (CDCl$_3$): 9.2 (broad s, NH), 8.6 (broad s, NH), 7.81 (dd, 1H), 7.48 (dd, 1H), 6.89 (m, 1H), 6.75 (d, 1H), 6.69 (m, 1H), 4.45 (dd, 1H), 4.33 (dd, 1H), 3.75 (m, 1H), 2.61 (m, 1H), 1.97 (m, 1H).

EXAMPLE 18

(+/−)-cis-1-(4,7-Difluoro-1,1a,2,7b-tetrahydro-cyclopropa[c]chromen-1-yl)-3-(5-ethynyl-pyridin-2-yl)-urea

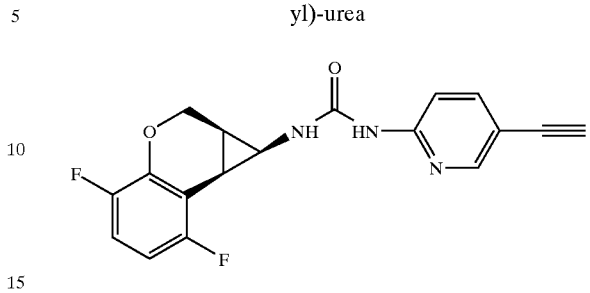

+/−cis-1-(4,7-Difluoro-1,1a,2,7b-tetrahydro-cyclopropa[c]chromen-1-yl)-3-(5-ethynyl-pyridin-2-yl)-urea was prepared analogously to Example 1c but using cis-4,7-difluoro-1,1a,2,7b-tetrahydro-cyclopropa[c]chromene-1-carboxylic acid (100 mg, 0.4 0.44 mmol) and 5-trimethylsilanylethynyl-pyridine-2-ylamine (93 mg, 0.49 mmol) to give (25 mg, 17%). The crude product was purified by extraction between 0.01 M HCl (aq) and ethyl acetat-ether (1:1) and chromatography (silica gel, ether). The mixture obtained (containing the title compound together with silylated compound) was stirred with Bu$_4$N$^+$F$^-$ in 25% water in THF for 30 min and the chromatography was repeated to obtain pure +/−cis-1-(4,7-Difluoro-1,1a,2,7b-tetrahydro-cyclopropa[c]chromen-1-yl)-3-(5-ethynyl-pyridin-2-yl)-urea.

$^1$H NMR (CDCl$_3$): 9.2(broad s, NH), 7.95 (d, 1H), 7.59 (dd, 1H), 7.48 (broad s, 1H), 6.89 (td, 1H), 6.64 (td, 1H), 6.57 (d, 1H), 4.46 (dd, 1H), 4.33 (dd, 1H), 3.78 (q, 1H), 3.11 (s, 1H), 2.62 (t, 1H), 1.99–1.97 (m, 1H)

EXAMPLE 19

(+/−)-cis-1-(5-Bromo-pyridin-2-yl)-3-(4,7-difluoro-1,1a,2,7b-tetrahydro-cyclopropa[c]chromen-1-yl)-urea

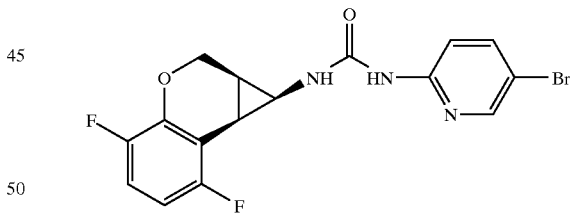

+/−-cis-1-(5-Bromo-pyridin-2-yl)-3-(4,7-difluoro-1,1a,2,7b-tetrahydro-cyclopropa[c]chromen-1-yl)-urea was prepared analogously to Example 1c but using cis-4,7-difluoro-1,1a,2,7b-tetrahydro-cyclopropa[c]chromene-1-carboxylic acid (50 mg, 0.22 mmol) and 6-amino-5-bromopyridine (42 mg, 0.24 mmol) to give +/−-cis-1-(5-bromo-pyridin-2-yl)-3-(4,7-difluoro-1,1a,2,7b-tetrahydro-cyclopropa[c]chromen-1-yl)-urea (50 mg, 35%). The crude product was purified by extraction between 0.01 M HCl (aq) and ethyl acetate and chromatography (silica gel, ether).

$^1$H NMR (CDCl$_3$): 9.2 (broad s, NH), 7.88 (d, 1H), 7.75 (broad s, 1H), 7.60 (dd, 1H), 6.89 (m, 1H), 6.63 (td, 1H ), 6.59 (d, 1H), 4.45 (dd, 1H), 4.33 (dd, 1H), 3.78 (q, 1H), 2.62 (t, 1H), 1.98 (m, 1H).

EXAMPLE 20

+/−cis-1-(4,7-Difluoro-1,1a,2,7b-tetrahydro-cyclopropa[c]chromen-1-yl)-3-(5-phenoxy-pyridin-2-yl)-urea

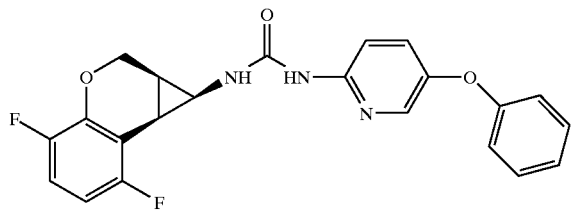

(+/−)-cis-1-(4,7-Difluoro-1,1a,2,7b-tetrahydro-cyclopropa[c]chromen-1-yl)-3-(5-phenoxy-pyridin-2-yl)-urea was prepared analogously to Example 1c) but using cis-4,7-difluoro-1,1a,2,7b-tetrahydro-cyclopropa[c]chromene-1-carboxylic acid (60 mg, 0.26 mmol) and 6-amino-5-phenoxypyridine (56 mg, 0.29 mmol) to give 32 mg (30%) of the title compound. The crude product was purified by extraction between 0.01 M HCl (aq) and ethyl acetate and chromatography (silica gel, 20% ether in n-hexane)

$^1$H NMR (CDCl$_3$): 7.60 (d, 1H), 7.45 (broad s, 1H), 7.37–7.34 (m, 2H), 7.27–7.24 (m, 2H), 7.14–7.11 (m, 1H), 6.94–9.92 (m, 2H), 6.79–7.74 (m, 1H), 6.63 (d, 1H), 6.59–6.55 (m, 1H), 4.43 (dd, 1H), 4.36 (dd, 1H), 3.75 (q, 1H), 2.59 (t, 1H), 1.98–1.94 (m, 1H).

EXAMPLE 21

(+/−)-cis-1-(5-Cyano-pyridin-2-yl)-3-(4,7-difluoro-1,1a,2,7b-tetrahydro-cyclproa[c]chromen-1-yl)-thiourea

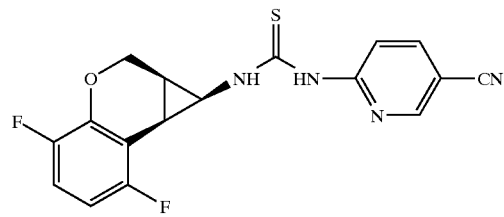

cis4,7-Difluoro-1,1a,2,7b-tetrahydro-cyclopropa[c]chromene-1-carboxylic acid (113 mg, 0.5 mmol), DPPA (118.6 μl, 0.55 mmol) and TEA (70.7 μl, 0.55 mmol) was refluxed in toluene (2 ml) for 1 h. Dioxane (3 ml) and HCl$_{(aq)}$ (1.5 ml, 6M) was then added and the reaction mixture was left for 1 h. at 50° C. Ether and water was then added and the layers separated. The water phase was washed with ether and then made alkaline with ammonia$_{(aq)}$. Extraction with dichloromethane and drying gave the intermdiate 4,7-difluoro-1,1a,2,7b-tetrahydrocyclopropa[c]chromen-1ylamine, which was directly treated with 6-isothiocyanato-nicotinonitril (34 mg, 0.55 mmol) in acetonitrile (4 ml) at RT over-night. The precipitated crystals were filtrated off and washed with cold acetonitrile to give 30 mg (17%) of pure (+/−)-cis-1-(5-Cyano-pyridin-2-yl)-3-(4,7-difluoro-1,1a,2,7b-tetrahydro-cyclopropa[c]chromen-1-yl)-thiourea LC-MS: m/z 358.9

EXAMPLE 22

1-(6-Chloro-5-cyano-pyridin-2-yl)-3-(5,7-difluoro-1,1a,2,7b-tetrahydro-cyclopropa[c]chromen-1-yl)urea

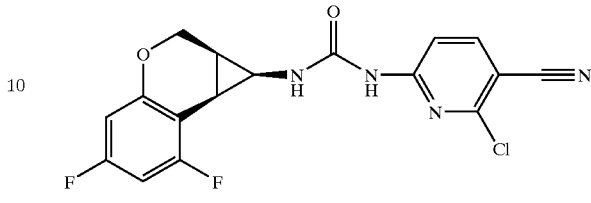

1-(6-Chloro-5-cyano-pyridin-2-yl)-3-(5,7-difluoro-1,1a,2,7b-tetrahydro-cyclopropa[c]chromen-1-yl)urea was prepared analogously to Example 1c) but using cis-5,7-difluoro-1,1a,2,7b-tetrahydro-cyclopropa[c]chromene-1-carboxylic acid (280 mg, 1.21 mmol) and 6-amino-2-chloro-3-cyanopyridine (203 mg, 1.33 mmol) to give the title compound in small amount. The crude product was purified by extraction between 0.01 M HCl (aq) and ether and chromatography (silica gel, ether) and washed with acetone-ether.

$^1$H NMR(DMSO-d$_6$): 10 (br s, NH), 8.20 (d, 1H), 7.70 (d, 1H), 6.9 (br s, NH), 6.8 (m, 1H), 6.6 (m, 1H), 4.4 (dd, 1H), 4.2 (dd, 1H), 3.2 (m, 1H), 2.4 (t, 1H), 1.9 (m, 1H).

EXAMPLE 23

1-(5-cyano-pyridin-2-yl)-3-(5,7-difluoro-1,1a,2,7b-tetrahydro-cyclopropa[c]chromen-1-yl)urea

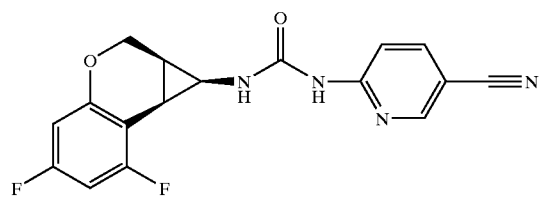

1-(5-cyano-pyridin-2-yl)-3-(5,7-difluoro-1,1a,2,7b-tetrahydro-cyclopropa[c]chromen-1-yl)urea was prepared analogously to Example 1c) but using cis-5,7-difluoro-1,1a,2,7b-tetrahydro-cyclopropa[c]chromene-1-carboxylic acid (390 mg, 1.72 mmol) and 2-amino-5-cyanopyridine (226 mg, 1.89 mmol). The crude product was purified by extraction between 0.01 M HCl (aq), recrystallization, several washings with aceton and acetonitrile and chromatography (silica gel, 1% EtOAc in ether) to give 28 mg of the title compound.

$^1$H NMR (CDCl3–MeOD): 8.16 (t, 1H), 7.78 (dd, 1H), 7.09 (d, 1H), 6.56–6.34 (m, 2H), 4.34 (m, 2H), 3.54 (t, 1H), 2.57 (dd, 1H), 2.00–1.90 (m, 1H).

EXAMPLE 24 cis-1-(4-Bromo-7-fluoro-1,1a,2,7b-tetrahydro-cyclopropa[c]chromen-1-yl)-3-(5-cyano-pyridin-2-yl)-urea

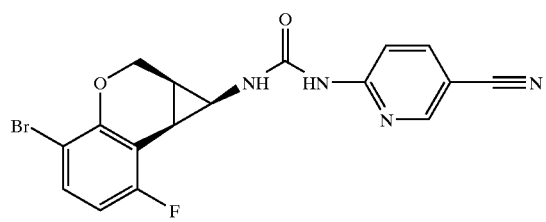

cis-1-(4-Bromo-7-fluoro-1,1a,2,7b-tetrahydro-cyclopropa[c]chromen-1-yl)-3-(5-cyano-pyridin-2-yl)-urea was prepared analogously to Example 1c but using cis-4-bromo-7fluoro-1,1a,2,7b-tetrahydro-cyclopropa[c]chromene-1-carboxylic acid (178 mg, 0.62 mmol) and 2-amino-5-cyanopyridine (0.81 mg, 0.68 mmol) The crude product was chromatographed (silica, ether) and washed with acetone to give 40 mg (16%) of cis-1-(4-Bromo-7-fluoro-1,1a,2,7b-tetrahydro-cyclopropa[c]chromen-1-yl)-3-(5-cyano-pyridin-2-yl)-urea.

$^1$H NMR (CDCl$_3$): 9.85 (s, 1H), 9.3 (s, 1H), 7.75 (dd, 1H), 7.33 (dd, 1H), 6.95 (d, 1H), 6.65 (t, 1H), 4.05 (dd, 1H), 4.32 (dd, 1H), 3.35 (t, H), 2.65 (t, 1H), 2.05–1.95 (m, 1H).

EXAMPLE 25 cis-1-(4-Bromo-7-fluoro-1,1a,2,7b-tetrahydro-cyclopropa[c]chromen-1-yl)-3-(6-chloro-5-cyano-pyridin-2-yl)-urea

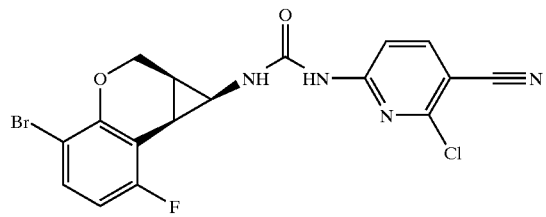

cis-1-(4-Bromo-7-fluoro-1,1a,2,7b-tetrahydro-cyclopropa[c]chromen-1-yl)-3-(6-chloro-5-cyano-pyridin-2-yl)-urea was prepared analogously to Example 1c but using cis-4-bromo-7fluoro-1,1a,2,7b-tetrahydro-cyclopropa[c]chromene-1-carboxylic acid (178 mg, 0.62 mmol) and 2-amino-6-chloro-5-cyanopyridine (105 mg, 0.68 mmol). The crude product was chromatographed (silica, 0→1% MeOH in ether) and washed with acetone-hexane to give 40 mg (13%) of cis-1-(4-bromo-7-fluoro-1,1a,2,7b-tetrahydro-cyclopropa[c]chromen-1-yl)-3-(6-chloro-5-cyano-pyridin-2-yl)-urea.

$^1$H NMR (CDCl$_3$): 9.90 (s, 1H), 8.30 (s, 1H), 7.75 (d, 1H), 7.25 (d, 1H), 6.60 (t, 1H), 4,5 (dd, 1H), 4.35 (dd, 1H), 3.5 (m, 1H), 2.65 (m, 1H), 2.1–1.95 (m, 1H).

EXAMPLE 26 cis-1-(4-Bromo-6-fluoro-1,1a,2,7b-tetrahydro-cyclopropa[c]chromen-1-yl)-3-(5-cyano-pyridin-2-yl)-urea

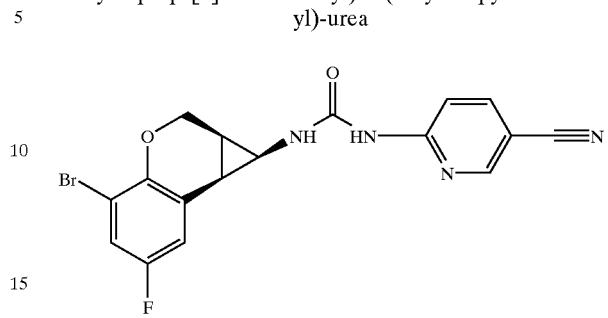

cis-1-(4-Bromo-6-fluoro-1,1a,2,7b-tetrahydro-cyclopropa[c]chromen-1-yl)-3-(5-cyano-pyridin-2-yl)-urea urea was prepared analogously to Example 1c but using cis4-bromo-6-fluoro-1,1a,2,7b-tetrahydro-cyclopropa[c]chromene-1-carboxylic acid (177 mg, 0.62 mmol) and 2-amino-5-cyanopyridine (81 mg, 0.68 mmol). The crude product was extracted between ether and 0.02 M HCl$_{(aq)}$, chromatographed (silica, 0→1% MeOH in ether) and washed with acetone-hexane to give 42 mg (17%) of cis-1-(4-Bromo-6-fluoro-1,1a,2,7b-tetrahydro-cyclopropa[c]chromen-1-yl)-3-(5-cyano-pyridin-2-yl)-urea.

$^1$H NMR (CDCl3–MeOD): 8.37 (m, 1H), 7.75 (dd, 1H), 7.14 (dd, 1H), 7.05 (dd, 1H), 6.93 (d, 1H), 4.56 (dd, 1H), 4.21 (dd, 1H), 3.77 (t, 1H), 2.42 (dd, 1H), 2.00 (m, 1H).

EXAMPLE 27 cis-1-(4-Bromo-6-fluoro-1,1a,2,7b-tetrahydro-cyclopropa[c]chromen-1-yl)-3-(6-cloro-5-cyano-pyridin-2-yl)-urea

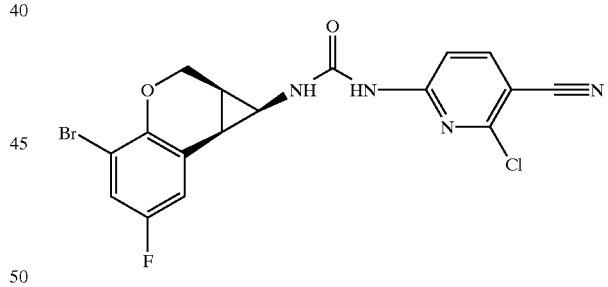

cis-1-(4-Bromo-6-fluoro-1,1a,2,7b-tetrahydro-cyclopropa[c]chromen-1-yl)-3-(6-chloro-5-cyano-pyridin-2-yl)-urea was prepared analogously to Example 1c) but using cis-4-bromo-6-fluoro-1,1a,2,7b-tetrahydro-cyclopropa[c]chromene-1-carboxylic acid (177 mg, 0.62 mmol) and 2-amino-6-chloro-5-cyanopyridine (105 mg, 0.68 mmol). The crude product was extracted between ether and 0.01 M HCl$_{(aq)}$, chromatographed (silica, 0→1% MeOH in ether) and washed with acetone-hexane to give 46 mg (17%) of cis-1-(4-bromo-6-fluoro-1,1a,2,7b-tetrahydro-cyclopropa[c]chromen-1-yl)-3-(6-cloro-5-cyano-pyridin-2-yl)-urea.

$^1$H NMR (CDCl3): 9.41 (s1H,), 8.28 (dd, 1H), 7.04 (dd, 1H), 4.54 (dd, 1H), 4.25 (dd, 1H), 3.50 (m, 1H), 2.41 (dd, 1H), 2.06–1.98 (m, 1H).

EXAMPLE 28

Cis-1-(5-cyanopyridin-2-yl)-3-(6-fluoro-1,1a,2,7b-tetrahydro-cyclopropa[c]chromen-1-yl)urea

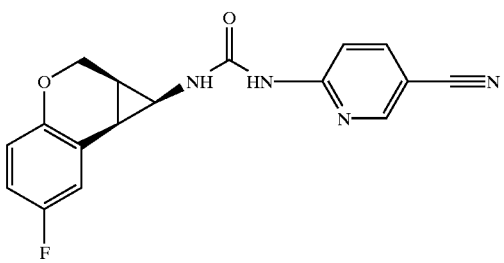

cis-1-(5-Cyano-pyridin-2-yl)-3-(6-fluoro-1,1a,2,7b-tetrahydro-cyclopropa[c]chromen-1-yl)urea was prepared analogously to Example 1c) but using cis-6-fluoro-1,1a,2,7b-tetrahydro-cyclopropa[c]chromene-1-carboxylic acid (168 mg, 0.8 mmol) and 2-amino-5-cyanopyridine (105 mg, 0.88 mmol). The crude product was extracted between ether and 0.01 M HCl$_{(aq)}$ chromatographed (silica, 0→1% MeOH in ether) and washed with aceton-hexane to give only 10 mg (4%) of cis-1-(5-cyano-pyridin-2-yl)-3-(6-fluoro-1,1a,2,7b-tetrahydro-cyclopropa[c]chromen-1-yl)urea.

$^1$H NMR (CDCl3–MeOD): 8.16 (d, 1H), 7.73 (dd, 1H), 7.05 (dd, 1H), 6.96 (d, 1H), 6.84 (td, 1H), 6.76 (dd, 1H), 4.39 (dd, 1H), 4.17 (dd, 1H), 3.67 (t, 1H), 2.39 (dd, 1H), 1.96–1.92 (m, 1H).

EXAMPLE 29

Intermediates 29a) 6-Fluorochroman-4-ol

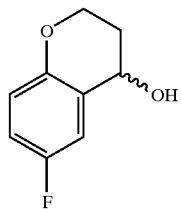

6-Fluorochroman-4-one (10 g, 61 mmol) was dissolved in ethanol (100 ml). NaBH$_4$ (excess) was added and cooled on icebath. The mixture was then left in room temperature for 2 h, folowed by reflux for 4 h. Purification by chromatography (silica gel, ether-hexane, 1:5) gave 8. g (80%) pure 6-fluoro-chroman-4-ol.

29b) 6-Fluoro-2H-chromene

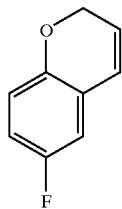

6-Fluorochroman-4-ol (8 g, 48 mmol) and toluene-4-sulphonic acidn (1 g) were dissolved in toluene and refluxed over-night with subsequent water removal. The mixture was then cooled and washed with NaHCO$_3$ (aq) and purified by chromatography (silica gel, n-hexane) to give 4.2 g (52%) of pure 6-fluoro-2H-chromene.

29c) +/–cis-6-Fluoro-1,1a,2,7b-tetrahydro-cyclopropa[c]chromene-1-carboxylic acid ethyl ester

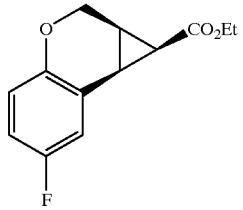

This Compound was prepared analogously to cis4,7-Difluoro-1,1a,2,7b-tetrahydro-cyclopropa[c]chromene-1-carboxylic acid ethyl ester but using 6-fluoro-2H-chromene to give 1.9 (29%) of the title compound.

29d) Cis-6-Fluoro-1,1a,2,7b-tetrahydro-cyclopropa[c]chromene-1-carboxylic acid

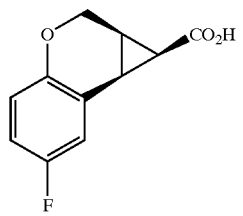

This compound was prepared analogously to cis-4,7-difluoro-1,1a,2,7b-tetrahydro-cyclopropa[c]chromene-1-carboxylic acid but using cis-6-fluoro-1,1a,2,7b-tetrahydro-cyclopropa[c]chromene-1-carboxylic acid ethyl ester (1.9 g, 8 mmol) to give 350 mg (21%) of pure cis-6-fluoro-1,1a,2,7b-tetrahydro-cyclopropa[c]chromene-1-carboxylic acid 29e) 1-Bromo-4-fluoro-2-prop-2-ynyloxy-benzene

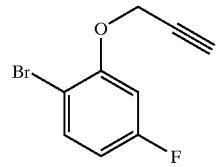

This compound was prepared analogously to 2,4-difluoro-2-prop-ynyloxy-benzene but using 2-bromo-5-fluorphenol (15 g, 78 mmol) to give 1-bromo-4-fluoro-2-prop-2-ynyloxy-benzene 15.6 g (87%)

29f) 2-Bromo-4-fluoro-1-prop-2-ynyloxy-benzene

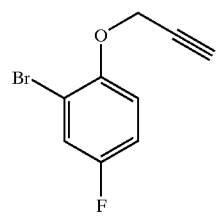

This compound was prepared analogously to 2,4-difluoro-2-prop-ynyloxy-benzene but using 2-bromo-4-fluoro-phenol (15 g, 78 mmol) to give 2-bromo-4-fluoro-1-prop-2-ynyloxy-benzene 15. g (84%).

29g) 1,3-difluoro-5-prop-2-ynyloxy-benzene

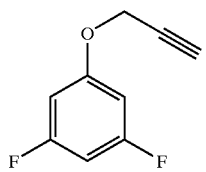

This compound was prepared analogously to 2,4-difluoro-2-propynyloxybenzene but using 3,5-difluoro-phenol (14 g, 107 mmol) to give 1,3-difluoro-5-prop-2-ynyloxy-benzene 12 g (67%).

9h) 8-Bromo-6-fluoro-2H-chromene

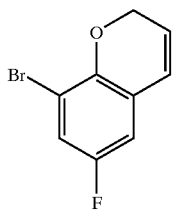

This compound was prepared analogously to 5,8-difluoro-2H-chromene but using (15 g, 65 mmol) of 2-bromo-4-fluoro-1-prop-2-ynyloxybenzene to give the title compound (7 g, 46%)

29i) 8-Bromo-5-fluoro-2H-chromene

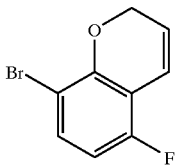

This compound was prepared analogously to 5,8-difluoro-2H-chromene but using (15 g, 65 mmol) of 1-bromo-4-fluoro-2-prop-2-ynyloxybenzene to give the title compound (3.7 g, 25

29j) 5,7-Difluoro-2H-chromene

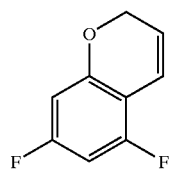

This compound was prepared analogously to 5,8-difluoro-2H-chromene but using (18 g, 107 mmol) of 1,3-difluoro-5-prop-2-ynyloxybenzene and PEG-200 as solvent to give the title compound (4 g, 23%).

29k) +/−cis-4-Bromo-6-fluoro-1,1a,2,7b-tetrahydro-cyclopropa[c]chromene-1-carboxylic acid ethyl ester

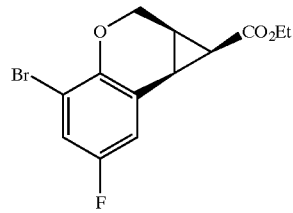

This compound was prepared analogously to +/−cis-4,7-difluoro-1,1a,2,7b-tetrahydro-cyclopropa[c]chromene-1-carboxylic acid ethyl ester but using 5 g (22 mmol) of 8-bromo 6-fluoro-2H-chromene to give 1.9 g (30%) of cis-6-fluoro-1,1a,2,7b-tetrahydro-cyclopropa[c]chromene-1-carboxylic acid ethyl ester.

29l) +/−cis-4-Bromo-7-fluoro-1,1a,2,7b-tetrahydro-cyclopropa[c]chromene-1-carboxylic acid ethyl ester

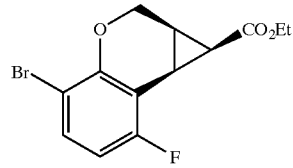

This compound was prepared analogously to +/−cis-4,7-difluoro-1,1a,2,7b-tetrahydro-cyclopropa[c]chromene-1-carboxylic acid ethyl ester but using 3.5 g (15.3 mmol) of 8-bromo-5-fluoro-2H-chromene to give 1.6 g (33%) of +/−cis-4-bromo-7-fluoro-1,1a,2,7b-tetrahydro-cyclopropa[c]chromene-1-carboxylic acid ethyl ester.

29m) +/−cis-5,7-Difluoro-1,1a,2,7b-tetrahydro-cyclopropa[c]chromene-1-carboxylic acid ethyl ester

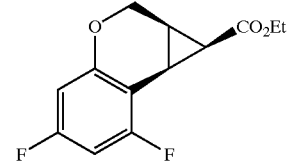

This compound was prepared analogously to +/−cis-4,7-difluoro-1,1a,2,7b-tetrahydro-cyclopropa[c]chromene-1-carboxylic acid ethyl ester but using 2 g (12 mmol) of 5,7-difluoro-2H-chromene to give 0.9 g (29%) of +/−cis-5,7-difluoro-1,1a,2,7b-tetrahydro-cyclopropa[c]chromene-1-carboxylic acid ethyl ester.

EXAMPLE 30

Optical Isomers of cis-1-(5-Cyano-pyridin-2-yl)-3-(4,7-difluoro-1,1a,2,7b-tetrahydro-cyclopropa[c]chromen-1-yl)-urea Racemic (+/−)-cis-1-(5-cyano-pyridin-2-yl)-3-(4,7-difluoro-1,1a,2,7b-tetrahydro-cyclopropa[c]chromen-1-yl)-urea (see Example 15) was separated into optically active compounds by using a chiral AGP 150×10 mm, 5 µm; Crom Tech LTD Colomn. The flow rate was set to 4 ml/min. The mobile phase was 89 vol % 10 mM HOAc/NH$_4$OAc in acetonitrile. Two elution peaks are seen. The isomer eluting second, typically exhibiting negative rotation is particularly active.

Without in any way wishing to be bound by this observation, it is believed that the more slowly eluting isomer bears the absolute configuration depicted below, which has been established by reference to x-ray crystallographic coordinates of the unsubstituted analogue of Example 1 liganded within reverse transcriptase enzyme. The configuration depicted below is clearly seen in the solved structure, whereas the other enantiomer is not present.

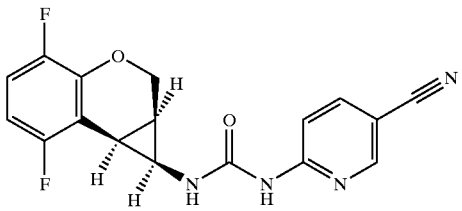

EXAMPLE 31

(−) cis-1-(5-Chloro-pyridin-2-yl)-3-(4,7-difluoro-1,1a,2,7b-tetrahydro-cyclopropa[c]chromen-1-yl)-urea Racemic (+/−)-cis-1-(5-chloropyridin-2-yl)-3-(4,7-difluoro-1,1a,2,7b-tetrahydro-cyclopropa[c]chromen-1-yl)-urea (see Example 17) was separated into optically active compounds by using a chiral AGP 150×10 mm, 5 μm; Crom Tech LTD Colomn. The flow rate was set to 4 ml/min. The mobile phase was 89 vol % 10 mM HOAc/NH$_4$OAc in acetonitrile. Two elution peaks at 27.7 min and 33.2 min are seen. The title isomer eluting at 33.2 min, typically exhibiting negative rotation, is particularly active.

EXAMPLE 32

(−)cis-1-(5-Cyano-pyridin-2-yl)-3-(7-fluoro-4-chloro-1,1a,2,7b-tetrahydro-cyclopropa[c]chromen-1-yl)-urea a) Resolution of the Racemic cis-7-fluoro-4-chloro-1,1a,2,7b-tetrahydro-cyclopropa[c]chromene-1-carboxylic acid 0.32 g (1.32 mmol) of racemic cis-7-fluoro-4-chloro-1,1a,2,7b-tetrahydro-cyclopropa[c]chromene-1-carboxylic acid was dissolved in hot acetonitrile (50 ml) and (1R,2R)-2-benzyloxycyclopentylamine (0.25 g, 1.32 mmol) was added. The resulting solution was left for crystallization. After few hours the mother liquor was decanted and crystals were washed with acetonitrile. The second crystallization from acetonitrile gave 92 mg of pure diastereomeric salt. The salt was treated with 1M HCl and resulting mixture was extracted with ethyl acetate. The organic phase was washed with water, brine and evaporated to give 0.05 g of enantiomeric cis-7-fluoro-4-chloro-1,1a,2,7b-tetrahydro-cyclopropa[c]chromene-1-carboxylic acid.

b) (−)cis-1-(5-Cyano-pyridin-2-yl)-3-(7-fluoro-4-chloro-1,1a,2,7b-tetrahydro-cyclopropa[c]chromen-1-yl)-urea The title compound was synthesized analogously to Example 1c) from enantiomeric cis-7-fluoro-4-chloro-1,1a,2,7b-tetrahydro-cyclopropa[c]chromene-1-carboxylic acid (50 mg). Yield 60.2 mg (84%). [α]$_D$=−0.388 (c=0.5, CHCl$_3$).

EXAMPLE 33

+/−cis-N-(5-cyano-2-pyridinyl)-N'-(4,7-dichloro-1,1a,2,7b-tetrahydrocyclopropa[c]chromen-1-yl)urea a) 1,4-dichloro-2-(2-propynyloxy)benzene

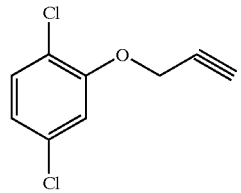

2,5-Dichlorophenol (8 g, 49 mmol) was mixed with potassium carbonate (13.6 g, 98 mmol) and 80% solution of propargyl bromide in toluene (11 ml, 98 mmol) in acetone (100 ml) and stirred overnight at room temperature. The precipitate was removed by filtration and washed with acetone. The acetone solution obtained was concentrated by rotary evaporation and kept under vacuum for 5 h. The product was obtained as yellow oil with quantitative yield. It was used for further transformations without additional purification.

b) 5,8-dichloro-2H-chromene

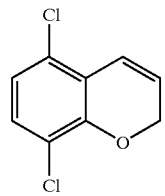

1,4-Dichloro-2-(2-propynyloxy)benzene was degassed and heated at stirring under argon for 4 h at 22420 C. The reaction mixture was then distilled in Kugelrohr apparatus (150–175° C./4.1×10$^{-2}$ mbar) to give 3.58 g of desired product as white solid. Yield 36% from starting dichlorophenol.

c) +/−cis-ethyl 4,7-dichloro-1,1a,2,7b-tetrahydrocyclopropa[c]chromene-1-carboxylate

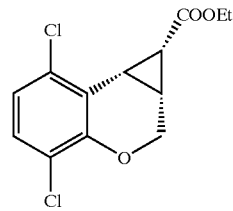

5,8-Dichloro-2H-chromene (3.15 g, 16 mmol), (Rh(II) Ac$_2$)$_2$ (30 mg, 0.1 mol %) was dissolved in degassed dry methylene chloride (3 ml). Ethyl diazoacetate (3 ml, 2 eq.) in the same solvent was added by a syringe at the flow rate 0.4 ml/h over a period of approximately 5 h under N$_2$ atmosphere. The reaction mixture was then washed with NH$_4$Cl (aq), water and brine and the solvent removed. The product (45% cis, 55% trans) was purified by chromatography on silica (200 g, ethyl acetate/n-hexane 1:15) to give 0.9 g of the pure cis product (racemate). Yield 20%. M$^+$=287.

¹H-NMR (CDCl₃): 7.15 (d, 1H, J=8.5 Hz), 6.91 (d, 1H, J=8.8 Hz), 4.59 (dd, 1H, J₁=12.02, J₂=7.03), 4.48 (dd, 1H, J₁=12.02, J₂=4.10), 4.07–3.94 (m, 3H), 2.62 (t, 1H, J=8.8 Hz), 2.27 (t, 1H, J=8.36 Hz), 2.20–2.12 (m, 1H), 1.1 (t, 3H).

d) +/–cis-4,7-dichloro-1,1a,2,7b-tetrahydrocyclopropa[c]chromene-1-carboxylic acid

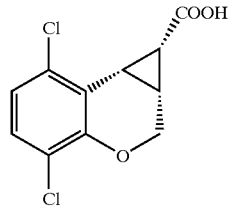

+/–cis-Ethyl 4,7-dichloro-1,1a,2,7b-tetrahydrocyclopropa[c]chromene-1-carboxylate was mixed with methanol (3 ml) and water solution of NaOH (1.5 eq., 3 ml) and heated at stirring for 1.5 h at 60° C. The extraction of basic reaction mixture into hexane showed that no starting material present. The reaction mixture was acidified with excess of 3M HCl solution (pH=1). The precipitate formed was collected by suction and washed with water. White solid obtained was dried under high vacuum (yield 80%).

e) +/–cis-N-(5-cyano-2-pyridinyl)-N'-(4,7-dichloro-1,1a,2,7b-tetrahydrocyclopropa[c]chromen-1-yl)urea

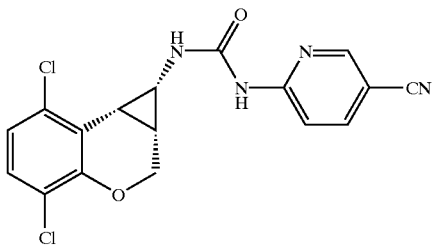

+/–cis-4,7-dichloro-1,1a,2,7b-tetrahydrocyclopropa[c]chromene-1-carboxylic acid (100 mg, 0.39 mmol) was mixed with toluene (3 ml), triethylamine (1.1 eq), 5-cyano-2-aminopyridine (1.1 eq), DPPA (1.1 eq) and bubbled with argon for about 5 min. The reaction mixture was then heated at stirring at 115° C. for 3 h under argon. The reaction mixture was concentrated by rotary evaporation and mixed with small amount of dry ethanol. The precipitate formed was collected by suction and washed with ethanol (2×2 ml) Desired product (+/–cis isomer) was obtained as beige-white powder (65 mg, yield 45%).

¹H-NMR (DMSO-d₆): 9.83 (s, 1H), 8.34 (d, 1H), 8.03 (dd, 1H), 7.75 (br s, 1H), 7.44 (d, 1H), 7.30 (d, 1H), 7.10 (d, 1H), 4.43 (dd, 1H), 4.18 (dd, 1H), 3.55–3.45 (m, ~1H overlapped with H₂O signal), 2.54 (dd, 1H), 2.10–2.02 (m, 1H).

EXAMPLE 34

+/–cis-N-(5-chloro-2-pyridinyl)-N'-(4,7-dichloro-1,1a,2,7b-tetrahydrocyclopropa[c]chromen-1-yl)urea

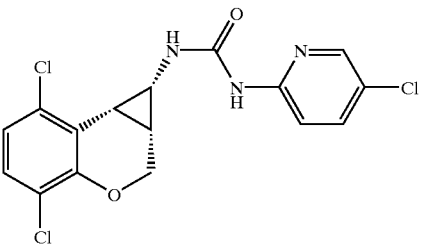

+/–cis-N-(5-chloro-2-pyridinyl)-N'-(4,7-dichloro-1,1a,2,7b-tetrahydrocyclopropa[c]chromen-1-yl)urea was synthesized analogously to Example 33 from +/–cis-4,7-dichloro-1,1a,2,7b-tetrahydrocyclopropa[c]chromene-1-carboxylic acid (100 mg, 0.39 mmol) and 2-amino-5-chloropyridine (1.1 eq) to give 66 mg of product as white powder. Yield 44%.

¹H-NMR (DMSO-d₆): 9.47 (s, 1H), 7.98 (d, 1H), 7.86 (br s, ~1H), 7.83 (dd, 1H), 7.30 (d, 1H), 7.23 (d, 1H), 7.10 (d, 1H), 4.44 (dd, 1H), 4.18 (dd, 1H) 3.55–3.48 (m, 1H), 2.54 (dd, 1H), 2.10–2.02 (m, 1H).

EXAMPLE 35

+/–cis-N-(5-bromo-2-pyridinyl)-N'-(4,7-dichloro-1,1a,2,7b tetrahydrocyclopropa[c]chromen-1-yl)urea

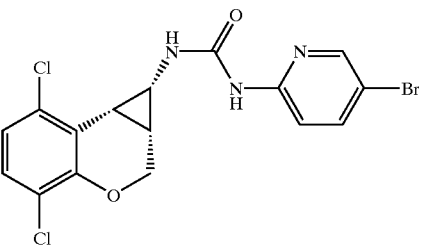

+/–cis-N-(5-bromo-2-pyridinyl)-N'-(4,7-dichloro-1,1a,2,7b-tetrahydrocyclopropa [c]chromen-1-yl)urea was synthesized analogously to Example 33 from +/–cis-4,7-dichloro-1,1a,2,7b-tetrahydrocyclopropa[c]chromene-1-carboxylic acid (100 mg, 0.39 mmol) and 2-amino-5-bromopyridine (1.1 eq) to give 35 mg of product as grey powder. Yield 21%.

¹H-NMR (DMSO-d₆): 9.47 (s, 1H), 7.97 (d, 1H), 7.86 (br s, ~1H), 7.83 (dd, 1H), 7.30 (d, 1H), 7.23 (d, 1H), 7.10 (d, 1H), 4.43 (dd, 1H), 4.18 (dd, 1H), 3.55–3.48 (m, 1H), 2.54 (dd, ~1H overlapped with DMSO signal), 2.08–2.01 (m, 1H).

EXAMPLE 36

+/−cis-N-(5-phenoxy-2-pyridinyl)-N'-(4,7-dichloro-1,1a,2,7b-tetrahydrocyclopropa[c]chromen-1-yl)urea

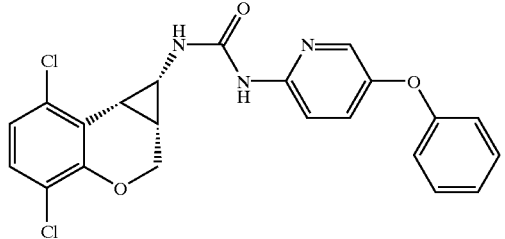

+/−cis-N-(5-phenoxy-2-pyridinyl)-N'-(4,7-dichloro-1,1a, 2,7b-tetrahydrocyclopropa[c]chromen-1-yl)urea was synthesized analogously to Example 33 from +/−cis-4,7-dichloro-1,1a,2,7b-tetrahydrocyclopropa[c]chromene-1-carboxylic acid (58 mg, 0.22 mmol) and 2-amino-5-phenoxypyridine (1.1 eq) to give 49 mg of product as slightly brownish powder. Yield 49%.

$^1$H-NMR (CDCl$_3$): 9.30 (br s, 1H), 8.26 (s, 1H), 7.53 (d, 1H), 7.35 (m, 2H), 7.25 (dd, 1H), 7.16–7.10 (dd, ~1H overlapped with CHCl$_3$ signal), 7.05 (d, 1H), 6.97–6.90 (m, 3H), 6.72 (d, 1H), 4.46 (dd, 1H), 4.30 (dd, 1H), 2.73 (m, 1H), 2.63 (dd, 1H), 2.05–1.95 (m, 1H).

EXAMPLE 37

+/−cis-N-(7-chloro-4-fluoro-1,1a,2,7b-tetrahydrocyclopropa[c]chromen-1-yl)-N'-(5-cyano-2-pyridinyl)urea a) 5-chloro-2-fluorophenol

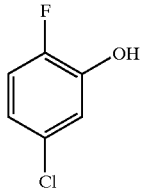

5-Chloro-2-fluoroaniline (10 g, 68 mmol) was dissolved in 6M sulfuric acid and cooled in ice/brine bath to −5° C. The solution of NaNO$_2$ (5.2 g, 76 mmol) in minimum amount of water was added dropwise to the stirred suspension at the temperature not higher then −2° C. After the addition clear yellow solution formed was allowed to stir for additional 30 min at cooling. CuSO$_4$ was dissolved water (80 ml) and mixed with sulfuric acid (32 ml). The diazonium salt solution was added dropwise to the preheated (160° C.) cuprous sulfate solution and the product was removed from the reaction flask by steam distillation. The reaction took about 2 h to be complete. The water/phnol solution was extracted into ether, washed with brine and dried over Na$_2$SO$_4$. Concentration gave 4 g of crude phenol (40%).

b) 4-chloro-1-fluoro-2-(2-propynyloxy)benzene

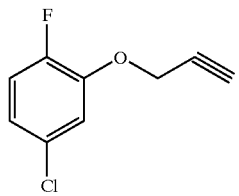

4-Chloro-1-fluoro-2-(2-propynyloxy)benzene was synthesized analogously to Example 33a from (4 g, 27 mmol) 4-chloro-1-fluorophenol to give 4.6 g of product (purified by column chromatography on silica, ethyl acetate/n-hexane 1:15) as yellow oil. Yield 90%.

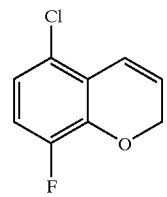

c) 5-chloro-8-fluoro-2H-chromene

5-Chloro-8-fluoro-2H-chromene was synthesized analogously to Example 33b) from 4-chloro-1-fluoro-2-(2-propynyloxy)benzene (4.6 g, 25 mmol) to give 1 g of product (purified by column chromatography on alumina, ethyl acetate/n-hexane 1:15) as colourless oil. Yield 22%.

d) ethyl +/−cis-7-chloro-4-fluoro-1,1a,2,7b-tetrahydrocyclopropa[c]chromene-1-carboxylate

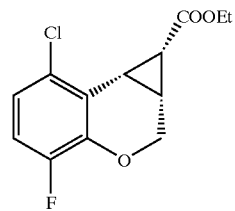

Ethyl +/−cis-7-chloro-4-fluoro-1,1a,2,7b-tetrahydrocyclopropa[c]chromene-1-carboxylate was synthesized analogously to Example 33c from 5-chloro-8-fluoro-2H-chromene (1 g, 5.4 mmol) to give 360 mg of +/−cis product (purified by column chromatography on silica, ethyl acetate/n-hexane 1:20) as white solid. Yield 25%.

e) +/−cis-7-chloro-4-fluoro-1,1a,2,7b-tetrahydrocyclopropa[c]chromene-1-carboxylic acid

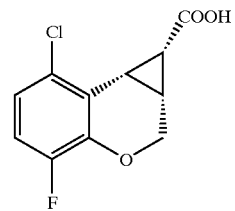

+/−cis-7-Chloro-4-fluoro-1,1a,2,7b-tetrahydrocyclopropa[c]chromene-1-carboxylic acid was synthesized analogously to Example 33d from ethyl +/−cis-7-chloro-4-fluoro-1,1a,2,7b-tetrahydrocyclopropa[c]chromene-1-carboxylate (360 mg, 1.3 mmol) to give 259 mg of +/−cis acid (80%).

f) +/-cis-N-(7-chloro-4-fluoro-1,1a,2,7b-tetrahydrocyclopropa[c]chromen-1-yl)-N'-(5-cyano-2-pyridinyl)urea

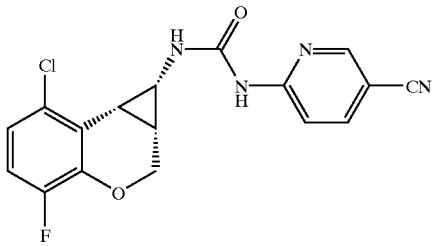

+/-cis-N-(7-chloro-4-fluoro-1,1a,2,7b-tetrahydrocyclopropa[c]chromen-1-yl)-N'-(5-cyano-2-pyridinyl)urea was synthesized analogously to Example 33e from +/-cis-7-chloro-4-fluoro-1,1a,2,7b-tetrahydrocyclopropa[c]chromene-1-carboxylic acid (60 mg, 0.25 mmol) and 2-amino-5-chloropyridine (1.1 eq) to give 59 mg of product as white powder. Yield 66%.

$^1$H-NMR (DMSO-d$_6$): 9.47 (br s, 1H), 7.89 (d, 1H), 7.80 (br s, 1H), 7.74 (dd, 1H), 7.32 (d, 1H), 7.16–7.05 (m, 2H), 4.39 (dd, 1H), 4.16 (dd, 1H), 3.55–3.48 (m, 1H), 2.51 (dd, ~1H overlapped with DMSO signal), 2.08–2.01 (m, 1H).

EXAMPLE 38

+/-cis-N-(7-chloro-4-fluoro-1,1a,2,7b-tetrahydrocyclopropa[c]chromen-1-yl)-N'-(5-chloro-2-pyridinyl)urea

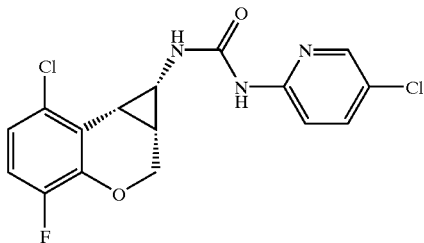

+/-cis-N-(7-chloro-4-fluoro-1,1a,2,7b-tetrahydrocyclopropa[c]chromen-1-yl)-N'-(5-chloro-2-pyridinyl)urea was synthesized analogously to Example 5 from +/-cis-7-chloro-4-fluoro-1,1a,2,7b-tetrahydrocyclopropa[c]chromene-1-carboxylic acid (60 mg, 0.25 mmol) and 2-amino-5-chloropyridine (1.1 eq) to give 59 mg of product as white powder. Yield 65%.

$^1$H-NMR (DMSO-d$_6$): 9.47 (br s, 1H), 7.89 (d, 1H), 7.80 (br s, 1H), 7.74 (dd, 1H), 7.32 (d, 1H), 7.16–7.04 (m, 2H), 4.39 (dd, 1H), 4.16 (dd, 1H), 3.55–3.48 (m, 1H), 2.51 (dd, 1H overlapped with DMSO signal), 2.06–2.01 (m, 1H).

EXAMPLE 39

+/–cis-N-(5-bromo-2-pyridinyl)-N'-(7-chloro-4-fluoro-1,1a,2,7b-tetrahydrocyclopropa[c]chromen-1-yl)urea

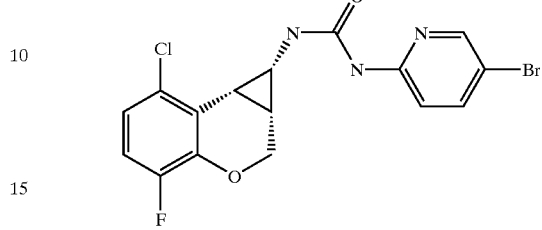

+/–cis-N-(5-bromo-2-pyridinyl)-N'-(7-chloro-4-fluoro-1,1a,2,7b-tetrahydrocyclopropa[c]chromen-1-yl)urea was synthesized analogously to Example 32e from +/-cis-7-chloro-4-fluoro-1,1a,2,7b-tetrahydrocyclopropa[c]chromene-1-carboxylic acid (60 mg, 0.25 mmol) and 2-amino-5-bromopyridine (1.1 eq) to give 56 mg of product as white powder. Yield 55%.

$^1$H-NMR (DMSO-d$_6$): 9.46 (br s, 1H), 7.96 (d, 1H), 7.83 (dd, 1H), 7.81 (br s, 1H), 7.27 (d, 1H), 7.16–7.04 (m, 2H), 4.38 (dd, 1H), 4.17 (dd, 1H), 3.55–3.48 (m, 1H), 2.51 (dd, ~1H oyerlapped with DMSO signal), 2.07–2.00 (m, 1H).

EXAMPLE 40

+/–cis-N-(7-chloro-4-fluoro-1,1a,2,7b-tetrahydrocyclopropa[c]chromen-1-yl)-N'-(5-phenoxy-2-pyridinyl)urea

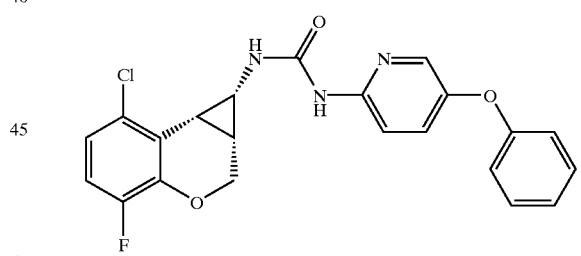

+/-cis-N-(7-Chloro-4-fluoro-1,1a,2,7b-tetrahydrocyclopropa[c]chromen-1-yl)-N'-(5-phenoxy-2-pyridinyl)urea was synthesized analogously to Example 32e from +/-cis-7-chloro-4-fluoro-1,1a,2,7b-tetrahydrocyclopropa[c]chromene-1-carboxylic acid (60 mg, 0.25 mmol) and 2-amino-5-phenoxypyridine (1.1 eq) to give 76 mg of product as slightly brownish powder. Yield 73%.

$^1$H-NMR (CDCl$_3$): 9.33 (br s, 1H), 7.93 (s, 1H), 7.51 (d, 1H), 7.38–7.32 (m, 2H), 7.25 (dd, ~1H overlapped with CHCl$_3$ signal), 7.16–7.10 (m, 1H), 6.96–6.88 (m, 3H), 6.79 (dd, 1H), 6.68 (d, 1H), 4.45 (dd, 1H), 4.25 (dd, 1H), 3.75–3.70 (m, 1H), 2.61 (dd, 1H), 2.05–1.95 (m, 1H).

EXAMPLE 41

N-[(1S,1aR,7bR) or (1R,1aS,7bS)-1.1a,2,7b-tetrahydrocyclopropa[c]-[1]benzothiopyran-1-yl]-N'-(5-cyano-2-pyridinyl)urea a) 3,4-dihydro-2H-1-benzothiopyran-4-ol

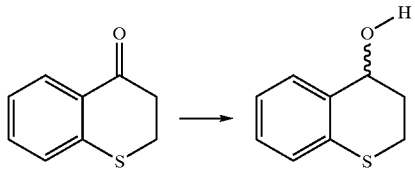

A solution of thiochroman-4-one (9 g) in ether (27 ml) was added slowly to a mixture of lithium aluminium hydride (0.53 g) in ether (54 ml). After the end of the addition, the mixture was refluxed for 2 hours. The reaction mixture was cooled and ice was added, followed by water and by a solution of 20% $H_2SO_4$. The water phase was washed twice with ether. The ether phase was washed twice with NaOH 2N, and once with water, dried over $MgSO_4$ and evaporated. The clear oil (8.9 g) crystallised after few hours. Rdt=97% b) 2H-1-benzothiopyran and 4H-1-benzothiopyran

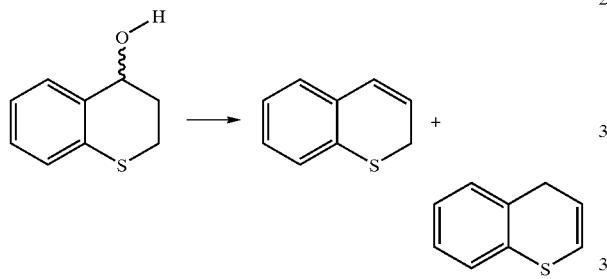

4-Thiochromanol (8.9 g) and potassium acid sulfate (0.89 g) were placed in a flask and evacuated to 1 mm. The flask was put in a bath heated at 90° C. until the alcohol melted. The magnetic stirrer was started and the bath slowly brought to 120° C. Dehydration was rapid and a mixture of the product and water distilled and was collected in a ice-cooled receiver. The product was taken up in ether and dried. The crude product (7 g, Rdt=88%) wasn't purified. The NMR showed the presence of 10% of the 4H-1-benzothiopyran.

c) Ethyl ester 1,1a,2,7b-tetrahydro-cyclopropa[c][1]benzothiopyran-1-carboxylic acid, (1S,1aR,7bR) or (1R,1aS,7bS)

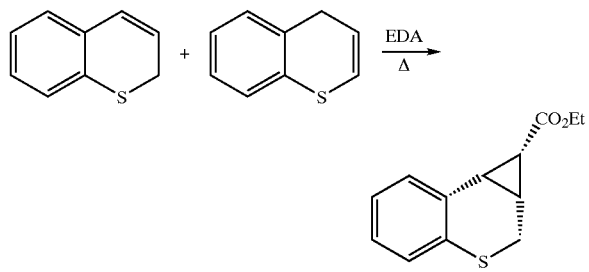

Ethyl diazoacetate was added slowly to 500 mg of thiochromene at 140 C. The reaction was followed by Gas chromatography and stopped when all starting material was consumed (about 7 hours). The residue was purified by flash chromatography (5% ether in hexane). The cis isomer (46,5 mg, Rdt=6%) was identified by NMR spectroscopy.

d) 1,1a,2,7b,tetrahydro-cyclopropa[c][1]benzothiopyran-1-carboxylic acid, (1S,1aR,7bR) or (1R,1aS,7bS)

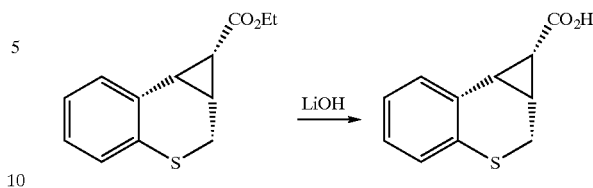

A mixture of the cis isomer (46,5 mg), LiOH (4 eq., 19 mg) in 5 ml of methanol/25% $H_2O$ was refluxed for 1 hour. After evaporation of the solvent under vacuum, the residue was dissolved in water and washed with ether. The water phase was acidified with concentrated HCl, and extracted twice with dichloromethane. After drying, the organic phase was evaporated and gave the desired acid (30 mg). Rdt= 73%.

e) N-[(1S,1aR,7bR) or (1R,1aS,7bS)-1.1a,2,7b-tetrahydrocyclopropa[c][1]benzothiopyran-1-yl]-N'-(5-cyano-2-pyridinyl)urea

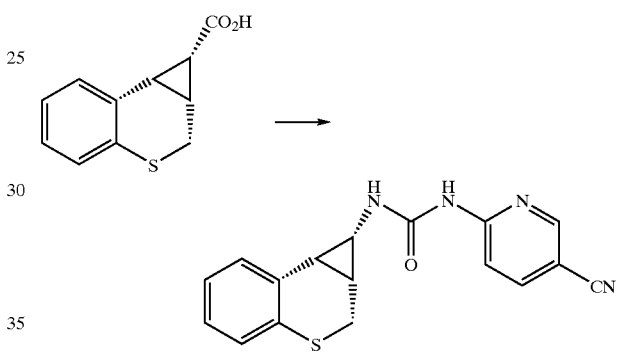

The cis acid (30 mg) was refluxed for 4 hours in toluene (2 ml) in presence of $Et_3N$ (0.02 ml), diphenyl phosphonic azide (0.03 ml) and 2-amino 6-cyanopyridine (19.5 mg). After cooling, the toluene phase was washed with water, followed by a solution of HCl (0.01 M). The organic phase was dried and evaporated. The residue was purified by flash chromatography (EtOAc 2/Hexane 1) and gave 10 mg of the desired compound. Rdt=22%.

$^1$H (DMSO-$d_6$): 1.96 (1H, m); 2.30 (1H, t, 8.6); 2.71 (1H, ddt, 13.65, 6.24); 3.24 (2H, m); 7.19 (3H, m); 7.37 (1H, dd, 7.4, 1.56); 7.42 (1H, dd, 9.0, 3.1); 7.60 (1H, NH); 8.02 (1H, dd, 9.0, 2.3); 8.15 (1H, s); 9.89 (1H, NH) Mass: 322 ($M^+$.), 321 (M–H)

EXAMPLE 42

(1S,1aR,7bS)-4,7-difluoro-1,1a,2,7b-tetrahydrocyclopropa[c]chromene-1-carboxylic acid a) (2Z)-3-(3,6-difluoro-2-methoxyphenyl)-2-propen-1-ol

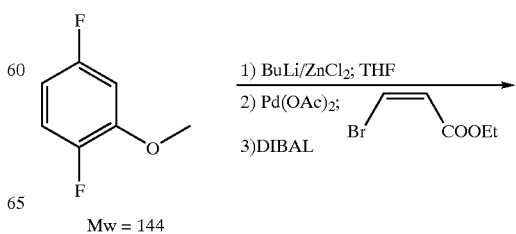

Mw = 144

-continued

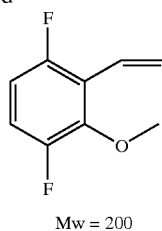

Mw = 200

A solution of BuLi (2.5M) in hexane (9.6 ml; 0.024 mol) was added to a stirred solution of 2,5-difluoroanisol (2.88 g, 0.02 mol) in dry THF (30 ml) at −70 C, followed after 2 h by solution of zinc chloride (3.6 g; 0.026 mol) in dry THF (50 ml). The reaction temperature was allowed to raise to room temperature and then stirring was maintained at room temperature for 30 min. Pd(OAc)$_2$ (8 mg; 0.2 mol %) was added, followed by ethyl cis-3-bromoacrylate (3.58 g; 0.02 mol). The reaction mixture was placed in preheated oil bath and heated under reflux for 1 h. The resulting reaction mixture was chilled to −78 C and 60 ml (0.06 mol) of DIBAL (1M solution in hexanes) was added dropwise. The stirring was continued at −78 C for 2 h and 1 h at room temperature. The reaction was quenched with water and all solids were dissolved by addition of HCl. The organic phase was diluted with ether, separated, washed with 5N HCl, brine and evaporated in vacuo. The residue was Kugelrohr distilled (1.5×10$^{-2}$ mbar, 150 C) to give 3.7 g (92%) of crude (2Z)-3-(3,6-difluoro-2-methoxyphenyl)-2-propen-1-ol, which contains ~6% of other regioisomers. The crude product was used in the next step without further purification.

$^1$H-NMR (CDCl$_3$): 7.00 (m, 1H); 6.77 (m, 1H); 6.31 (app. d, 1H); 6.12 (app. dt, 1H); 4.08 (br. t, 2H); 3.89 (d, 3H); 1.80 (br. t, 1H).

b) (2Z)-3-(3,6-difluoro-2-methoxyphenyl)prop-2enyl diazoacetate

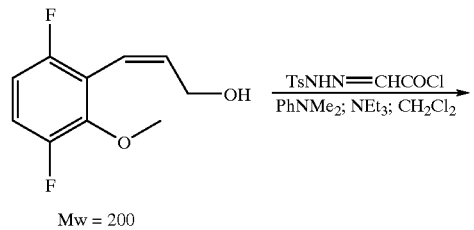

Mw = 200

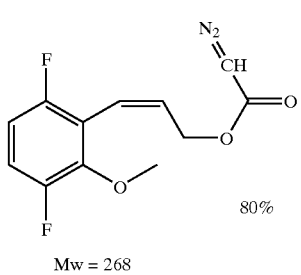

Mw = 268

The p-toluenesulfonylhydrozone of glyoxylic acid chloride (5.16 g; 0.02 mol) was added to a solution of (2Z)-3-(3,6-difluoro-2-methoxyphenyl)-2-propen-1-ol (3.6 g; 0.018 mol) in dry CH$_2$Cl$_2$ (50 ml) at −5 C, and N,N-dimethylaniline (2.5 ml; 0.02 mol) was added slowly. After stirring for 30 min at −5 C, Et$_3$N (12 ml; 0.09 mol) was added slowly. The resulting mixture was stirred for 15 min at −5 C and then for 30 min at room temperature, whereupon water (~50 ml) was added. The organic phase was separated washed with water, brine and concentrated in vacuo. Flash chromatography (silica, EA:Hex; 1:15) gave 3.86 g (80%) of product as a yellow solid.

$^1$H-NMR (CDCl$_3$): 7.00 (m, 1H); 6.76 (m, 1H); 6.41 (app. d, J=12.2 Hz; 1H); 6.00 (app. dt, J=12.2; 6.10 Hz; 1H); 4.71 (br. s, 1H); 4.67 (dt, 2H); 3.89 (d, 3H).

c) (1S,5R,6S)-6-(3,6-difluoro-2-methoxyphenyl)-3-oxabicyclo[3.1.0]hexan-2-one

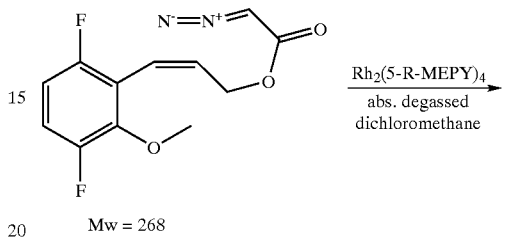

Mw = 268

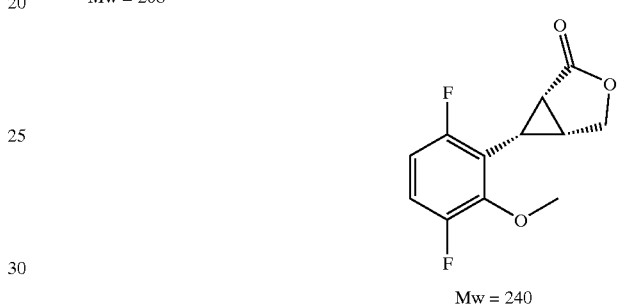

Mw = 240

(2Z)-3-(3,6-difluoro-2-methoxyphenyl)prop-2enyl diazoacetate (3.45 g, 0.013 mol) was dissolved in 100 ml of dried degassed dichloromethane and added dropwise to the solution of chiral Doyle catalyst (Aldrich, also available from Johnsson Matthey, 10 mg, 0.1 mol %) in 50 ml of dichloromethane under argon at ambient temperature over a period of ~6 h. The initial blue color had turned to olive by the end of the addition. The reaction mixture was concentrated in vacuo and the crude product was purified by flash chromatography (silica, EA:Hex, 1:5→1:1) to give 2.72 g (88%) of (1S,5R,6S)-6-(3,6-difluoro-2-methoxyphenyl)-3-oxabicyclo[3.1.0]hexan-2-one as colorless solid. Enantiomeric purity could be checked on this stage using Chiracel OD column, 10% IPA in hexane −94% ee.

$^1$H-NMR (CDCl$_3$): 7.00 (m, 1H); 6.72 (m, 1H); 4.33 (dd, 1H); 4.10 (d, 1H); 4.02 (d, 3H); 2.66 (m, 2H); 2.37 (t, 1H).

d) (1S,1aR,7bS)-1-(bromomethyl)-4,7-difluoro-1a,7b-dihydrocyclopropa[c]chromene-2(1H)-one.

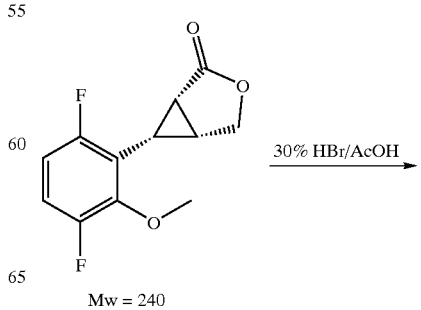

Mw = 240

-continued

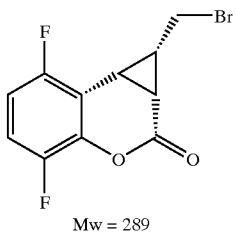

Mw = 289

(1S,5R,6S)-6-(3,6-difluoro-2-methoxyphenyl)-3-oxabicyclo[3.1.0]hexan-2-one (130 mg, 0.55 mmol) was mixed with 1.2 ml of 30% HBr/AcOH (6 mmol) and heated in a sealed vessel at stirring for about 4 h at 90° C. The reaction mixture was then cooled down, mixed with water and extracted into diethyl ether (3×20 ml). Ether extract was washed with sat. sodium bicarbonate solution and brine. Dried over magnesium sulfate. Concentration gave 160 mg of white solid material. 98% yield.

$^1$H-NMR (CDCl$_3$): 7.08 (m, 1H); 6.88 (m, 1H); 3.44 (dd, 1H); 3.06 (t, 1H); 2.96 (dd, 1H); 2.64 (dd, 1H); 2.46 (m, 1H).

e) (1S,1aR,7bS)-4,7-difluoro-1,1a,2,7b-tetrahydrocyclopropa[c]chromene-1-carboxylic acid

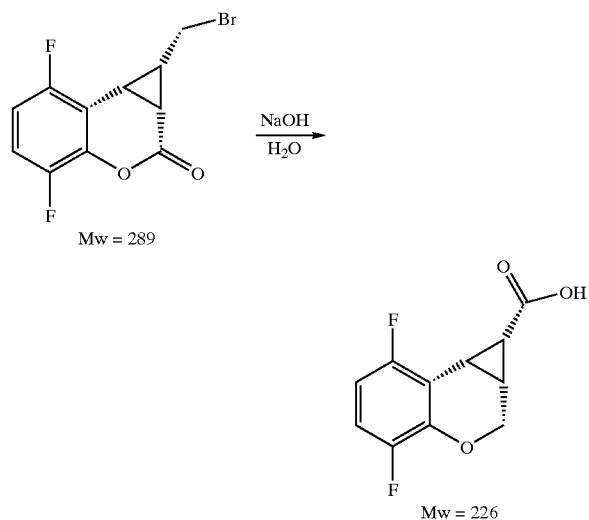

Mw = 289

Mw = 226

(1S,1aR,7bS)-1-(bromomethyl)-4,7-difluoro-1a,7b-dihydrocyclopropa[c]chromen-2(1H)-one (360 mg, 1.2 mmol) was mixed with the solution of NaOH (0.1 g, 2.5 mmol) in 5 ml of water and heated at stirring for 1 h at 90° C. After completion the reaction mixture was cooled down and extracted into diethyl ether (2×20 ml). Water phase was acidified with conc. HCl. The precipitate formed was collected by filtration to give 180 mg of pure product. Mother liquor was extracted into ether and washed with brine, dried over magnesium sulfate. Concentration gave additional 70 mg of product (containing up to 15% of impurities). Overall yield about 92%.

$^1$H-NMR (CDCl$_3$): 6.86 (m, 1H); 6.54 (m, 1H); 4.48 (m, 2H); 2.62 (t, 1H); 2.20 (t, 1H); 2.11(m, 1H).

EXAMPLE 43

(+/−) cis N-[1a,6b-dihydro-1H-benzo[b]cyclopropa[d]thien-1-yl]-N'-(5-cyano-2-pyridinyl)-urea

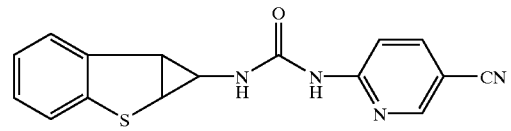

a) cis ethyl ester 1a,6b-dihydro-1H-benzo[b]cyclopropa[d]thiophene-1-carboxylic acid, (1S,1aS,6bR) or (1R,1aR,6bS)

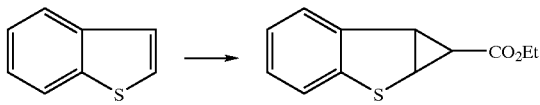

Ethyl diazoacetate is added slowly to 10 g of thiophene at 140° C. The reaction was checked by gas chromatography and stopped after 7 hours. The residue is purified by flash chromatography (5% ether in hexane). The cis isomer (917 mg, Rdt=6%) was identified by NMR spectroscopy.

Reference: Badger G. M. et al, *J. Chem. Soc.,* 1958, 1179–1184.

Badger G. M. et al, *J. Chem. Soc.,* 1958, 4777–4779.

b) cis 1a,6b-dihydro-1H-benzo[b]cyclopropa[d]thiophene-1-carboxylic acid, (1S,1aS,6bR) or (1R,1aR,6bS)

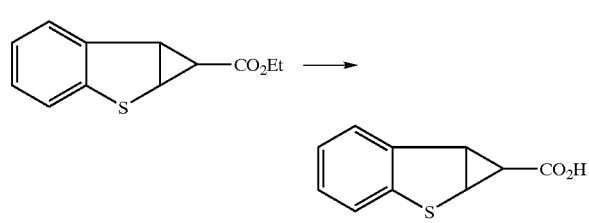

A mixture of the cis isomer (443 mg), LiOH (193 mg) in 15 ml of methanol/25% H$_2$O is refluxed for 1 hour. After evaporation of the solvent under vacuum, the residue is dissolved in water and washed with ether. The water phase is acidified with concentrated HCl, and extracted twice with dichloromethane. After drying, the organic phase is evaporated and gave the desired acid (313.6 mg). Rdt=81%.

c) (+/−) cis N-[1a,6b-dihydro-1H-benzo[b]cyclopropa[d]thien-1-yl]-N'-(5cyano-2-pyridinyl)-urea

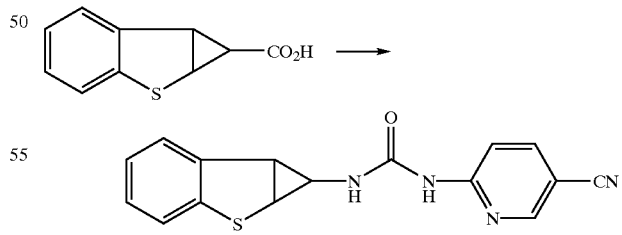

The cis acid (313 mg) was refluxed for 4 hours in toluene (20 ml) in presence of Et$_3$N (0.25 ml), diphenyl phosphoryl azide (0.3 ml) and 2-amino 6-cyanopyridine (220 mg). After cooling, the toluene phase was washed with water, followed by a solution of HCl (0.01 M). The organic phase was dried and evaporated. The residue was purified by flash chromatography (EtOAc 2/Hexane 1) and gave 10 mg of the desired compound. Rdt=2%.

¹H (DMSO-d₆): 3.32 (1H, m); 3.39 (1H, td, 8.05, 7.69); 3.52 (1H, dd, 7.69, 6.22); 7.08 (1H, td, 7.32, 1.1); 7.15 (1H, td, 7.32, 1.1); 7.22 (1H, dd, 8.4, 0.8); 7.39 (2H, m); 7.50 (1H, NH); 8.00 (1H, dd, 8.79, 2.2); 8.23 (1H, d, 2.2); 9.76 (1H, NH)

¹³C (DMSO-d₆): 25.6 (CH), 29.5 (CH), 33.7 (CH), 101.5 (C), 112.1 (CH), 118.0 (C), 122.1 (CH), 124.9 (CH), 127.3 (CH), 128.0 (CH), 136.3 (C), 141.7 (CH), 143.7 (C), 151.6 (CH), 155.1 (C), 156.1 (C) Mass: 310 (M+2), 309 (M+H)

EXAMPLE 44

(−)-cis-1-(5-Chloro-pyridin-2-yl)-3-(4,7-difluoro-1,1a,2,7b-tetrahydrocyclopropa[c]chromen-1-yl)-urea

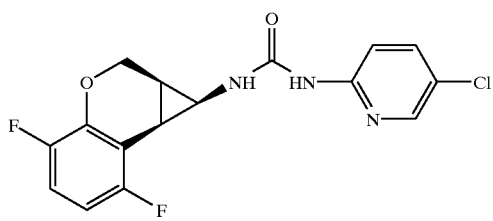

This compound was prepared analogously to Example 1c but using chiral (+)-cis-4,7-difluoro-1,1a,2,7b-tetrahydrocyclopropa[c]chromen-1-carboxylic acid (see Example 42e) (1.3 g, 5.75 mmol). The silica gel purified product was recrystallized from acetonitrile to give 0.95 g (47%) of the title product. Absolute stereochemical configuration assigned as for Example 30.

¹H-NMR (CDCl₃): 9.25 (broad s, 1H), 8.67 (s, 1H), 7.79 (d, 1H), 7.48 (dd, 1H), 6.92–6.86 (m, 1H), 6.71 (d, 1H), 6.65–6.60 (m, 1H), 4.45 (dd, 1H), 4.34 (dd, 1H), 3.80 (q, 1H), 2.61 (t, 1H), 2.00–1.98 (m, 1H).

EXAMPLE 45

(−)-cis-1-(5-Cyano-pyridin-2-yl)-3-(4,7-difluoro-1,1a,2,7b-tetrahydro-cyclopropa[c]chromen-1-yl)-urea

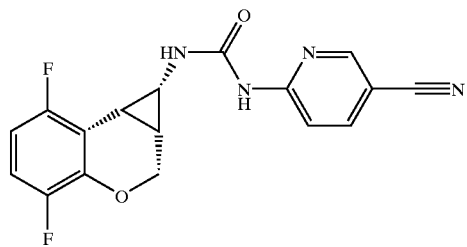

(+)-cis-4,7-Difluoro-1,1a,2,7b-tetrahydro-cyclopropa[c]chromene-1-carboxylic acid (see example 42e) (1,18 g, 5.2 mmol), diphenylphosphorylazide [1340 µL, 6.3 mmol (d=1.277)], triethylamine (870 µL, 6.3 mmol) and 2-amino-5-cyanopyridine (740 mg, 6.3 mmol) were dissolved in toluene (15 mL) and refluxed for 4 h. The solvent was then removed in vacuo and the crude product was dissolved in ether and washed (3×100 mL 0.01 M HCl) and purified by chromatography (silica gel, 0→1% MeOH in ether) to give pure (−)-cis-1-(5-cyano-pyridin-2-yl)-3-(4,7-difluoro-1,1a,2,7b -tetrahydro-cyclopropa[c]chromen-1-yl)-urea (1.1 g, 64%). ee 92% as determined by HPLC on a Chiral AGP column, eluent 11% acetonitrile in sodium phosphate buffer, flow 0.9 mL/min. Absolute stereochemical configuration assigned as for Example 30.

¹H-NMR (CDCl₃): 9 (s, NH), 8.42 (s, NH), 8.16 (d, 1H), 7.72 (dd, 1H), 6.97–6.76 (m, 2H), 6.69–6.61 (m, 1H), 4.47 (dd, 1H), 4.31 (dd, 1H), 3.75 (m, 1H), 2.65 (t, 1H), 2.05–1.96 (m, 1H).

EXAMPLE 46

(−)-cis-1-(5-cyano-pyridin-2-yl)-3-(4,7-difluoro-1,1a,2,7b-tetrahydro-cyclopropa[c]chromen-1-yl)-thiourea

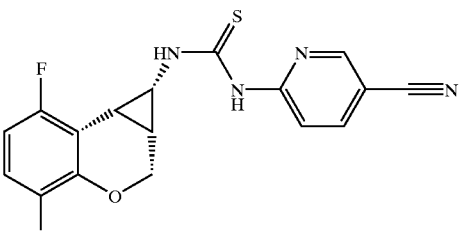

(±)-cis-4,7-Difluoro-1,1a,2,7b-tetrahydro-cyclopropa[c]chromene-1-carboxylic acid (2.2 g, 9.7 mmol), DPPA [2380 µl, 10.7 mmol 97%(d=1.277)] and TEA (1510 µl, 11.7 mmol) was refluxed in toluene (20 ml) for 2 h. Dioxane (26 mL) and HCl(aq) (26 mL, 6M) was then added and the reaction mixture was left for 1–2 h. At 50° C. Water (50 mL) was added and the water phase was washed with Ether (2×25 mL) and then made alkaline with ammonia(aq). Extraction with dichloromethane and drying gave the intermediate 4,7-difluoro-1,1a,2,7b-tetrahydrocyclopropa[c]chromen-1ylamine (1.37 g, 71%), which was directly treated with 6-isothiocyanato-nicotinonitrile (1.25 g, 7.7 mmol) in acetonitrile (2 mL) at RT over the weekend. The precipitated crystals were filtrated off and the solvent removed in vacuo and chromatographed (silica, 20% ether in pentane). The product obtained was combined with the crystals and the crude product (900 mg) was re-crystallised (ethanol-acetone) to give pure (−)-cis-1-(5-cyano-pyridin-2-yl)-3-(4,7-difluoro-1,1a,2,7b-tetrahydro-cyclopropa[c]-chromen-1-yl)-thiourea (590 mg 18%). Absolute stereochemical configuration assigned as for Example 30.

¹H-NMR (CDCl₃–MeOD): 8.1 (d, 1H), 7.77 (dd, 1H), 6.99–6.91 (m, 1H), 6.74 (dd, 1H) 6.73–6.66 (m, 1H), 4.48 (dd, 1H), 4.33 (dd, 1H), 4.20(dd, 1H), 2.78(t, 1H), 2.16–2.1 (m, 1H).

EXAMPLE 47

(±)-cis-1-(5-bromopyridin-2-yl)-3-(7-fluoro-4-propionyl-1,1a,2,7b-tetrahydro-cyclopropa[c]chromen-1-yl)-urea

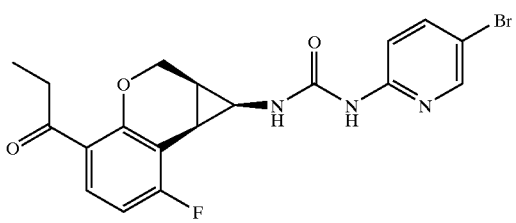

a) 1-(4-Fluoro-2-prop-2-ynyloxy-phenyl)-propan-1-one

To a mixture of NaH (95%, 278 mg, 11 mmol) in DMF (20 mL) at 0° C., was added 1-(4-fluoro-2-hydroxy-phenyl)-propan-1-one (1.68 g, 10 mmol) in DMF (5 mL). After 15 min at 0° C., was 3-bromo-propyne (3.02 g, 20 mmol) added to the reaction mixture. After 1 h at 0° C., was the reaction mixture allowed to assume room temperature. The reaction mixture was extracted with H₂O (100 mL). The H₂O phase was washed with Et₂O (3×100 mL) and the solvent of the combined organic phases was removed under reduced pressure. The crude product was purified by column chromatography (silica gel, CH₂Cl₂), to give 1.40 g (68%) of 1-(4-fluoro-2-prop-2-ynyloxy-phenyl)-propan-1-one.

¹H-NMR (CDCl₃): 7.64 (dd, 1H), 6.69 (dd, 1H), 6.60 (ddd, 1H), 4.68 (d, 2H), 2.85 (q, 2H), 2.58 (t, 1H), 1.03 (t, 3H).

b) 1-(5-Fluoro-2H-chromen-8-yl)-propan-1-one 1-(5-Fluoro-2H-chromen-8-yl)-propan-1-one was synthesized analagously to Example 3b from 1-(4-fluoro-2-prop-2-ynyloxy-phenyl)-propan-1-one (1.34 g, 6.5 mmol), to give 619 mg (46%) of 1-(5-fluoro-2H-chromen-8-yl)-propan-1-one.

¹H-NMR (CDCl₃): 7.60 (dd, 1H), 6.67–6.58 (m, 2H), 5.86 (dt, 1H), 4.76 (dd, 2H), 2.93 (q, 2H), 1.23 (t, 3H).

c) (±)-cis-7-Fluoro-4-propionyl-1,1a,2,7b-tetrahydro-cyclopropa[c]chromene-1-carboxylic acid ethyl ester (±)-cis-7-Fluoro-4-propionyl-1,1a,2,7b-tetrahydro-cyclopropa[c]chromene-1-carboxylic acid ethyl ester was synthesized according to method 3c) from 1-(5-fluoro-2H-chromen-8-yl)-propan-1-one (619 mg, 3 mmol), to give 142 mg (16%) of (±)-cis-7-fluoro-4-propionyl-1,1a,2,7b-tetrahydro-cyclopropa[c]chromene-1-carboxylic acid ethyl ester and (±)-trans-7-fluoro-4-propionyl-1,1a,2,7b-tetrahydro-cyclopropa[c]chromene-1-carboxylic acid ethyl ester as a byproduct.

¹H-NMR (CDCl₃): 7.59 (dd, 1H), 6.65 (m, 1H), 4.50–4.46 (m, 2H), 3.95 (q, 2H); 2.89 (q, 2H), 2.57 (dd, 1H), 2.20 (dd, 1H), 1.13–1.03 (m, 1H), 1.12–1.01 (m, 6H).

d) (±)-cis-7-Fluoro-4-propionyl-1,1a,2,7b-tetrahydro-cyclopropa[c]chromene-1-carboxylic acid (±)-cis-7-Fluoro-4-propionyl-1,1a,2,7b-tetrahydro-cyclopropa[c]chromene-1-carboxylic acid was synthesized analogously to Example 1b from (±)-cis-7-fluoro-4-propionyl-1,1a,2,7b-tetrahydro-cyclopropa[c]chromene-1-carboxylic acid ethyl ester (140.3 mg, 0.48 mmol), to give 83 mg (65%) of (±)-cis-7-fluoro-4-propionyl-1,1a,2,7b-tetrahydro-cyclopropa[c]chromene-1-carboxylic acid as a white solid. The crude product was purified by column chromatography (silica gel, 1→5% MeOH in CH₂Cl₂).

¹H-NMR (DMSO-d₆): 12.15 (br s, 1H), 7.46 (dd, 1H), 6.78 (dd, 1H), 4.57 (dd, 1H), 4.43 (dd, 1H), 2.93–2.80 (m, 2H), 2.55 (dd, 1H), 2.24 (dd, 1H), 2.20–2.10 (m, 1H), 1.02 (t, 3H).

e) (±)-cis-1-(5-bromopyridin-2-yl)-3-(7-fluoro-4-propionyl-1,1a,2,7b-tetrahydro-cyclopropa[c]chromen-1-yl)-urea The title compound is synthesized analogously to example 1c) by reacting 1 equivalent of (±)-cis-7-fluoro-4-propionyl-1,1a,2,7b-tetrahydro-cyclopropa[c]chromene-1-carboxylic acid and 1 eq of triethylamine in toluene with 1 eq of diphenylphosphinyl azide for 30 minutes at room temperature. The reaction mixture is heated to 120° C. and an approximately equimolar solution of 2-amino-5-bromopyridine is added. After 3 hours the solution is allowed to assume room temperature and the title compound extracted as shown above.

EXAMPLE 48

(1S,5R,6S)-6-(3,6-difluoro-2-methoxyphenyl)-2-methoxy-3-oxabicyclo[3.1.0]hexane

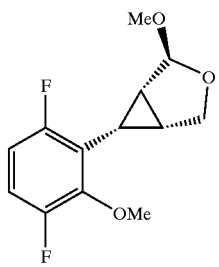

a) Iodo-3-oxabicyclo[3.1.0]hexan-2-one

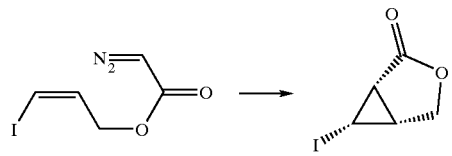

The title compound is synthesised in the depicted stereochemistry as described in Doyle J Amer Chem Soc 117 (21) 5763–5775 (1993)

b) Iodo-2-methoxy-3-oxabicyclo[3,1,0]hexane

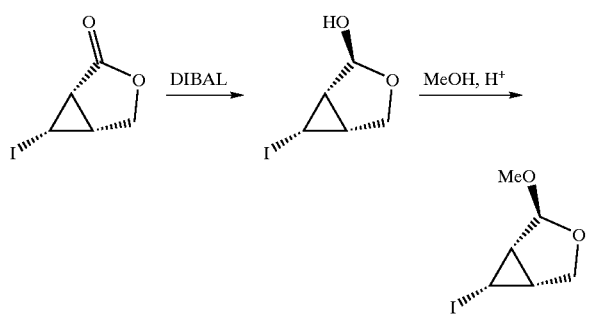

The title compound is synthesised in the depicted stereochemistry as described in Martin et al Tett Lett 39 1521–1524 (1998).

c) (1S,5R,6S)-6-(3,6-difluoro-2-methoxyphenyl)-2-methoxy-3-oxabicyclo[3.1.0]hexane

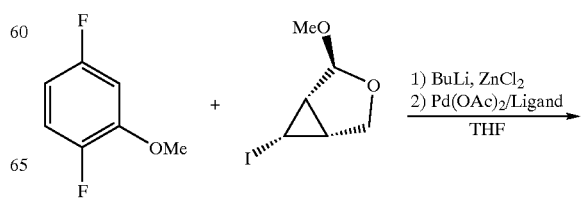

-continued

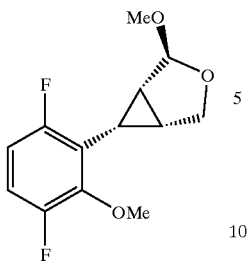

2,4-diflouroanisol (90 mg, 0.62 mmol) was dissolved in anhydrous, degassed, THF (7 ml) and cooled to −78° C. under $N_2$. nBuLi, 2,5 M in hexane, (0.30 ml, 0.77 mmol) was added and the reaction mixture was stirred at −78° C. for 2 hrs. $ZnCl_2$ (150 mg, 1.1 mmol), as a solution in anhydrous THF (7 ml), was added and the reaction mixture was allowed to warm to ambient temperature for 2 hrs. Iodo-2-methoxy-3-oxabicyclohexane (150 mg, 0.63 mmol), Pd (OAc)$_2$ (1.5 mg, 6.2 μmol), and ligand Tris(2,4-di-tert-butylphenyl)phosphite (40 mg, 62 μmol) were mixed in anhydrous THF (7 ml) and added to the reaction mixture. The reaction mixture was heated at reflux for 3 days and quenched with $H_2O$. Diethyl ether was added and the layers were separated, the organic layer was washed with $H_2O$ and aq. sat. NaCl, dried over $MgSO_4$, filtered and concentrated to give the title compound, otherwise denoted 2,4-di-fluoro-5-(cyclopropylacetal)anisol. Column chromatography on silica (EtOAc/Hexane 1:3) gave (4) 50 mg, 31%.

$^1$H NMR (CDCl$_3$) δ (ppm): 6.88–6.94 (m, 1H, ArH), 6.68–6.73 (m, 1H, ArH), 4.82 (s, 1H, CHOCH$_3$), 3.97–3.98 (m,1H, CHOCH) 3.94 (s, 3H, OCH$_3$), 3.79–3.81 (m, 1H, CHOCH) 3.30 (s, 3H, OCH$_3$), 2.13–2.19 (m, 2H, 2×CH-cyclopropyl), 1.89 (tr, J=7.81 Hz, 1H, CH cyclopropyl).

EXAMPLE 49 cis4,7-Difluoro-1,1a,2,7b-tetrahydro-cyclopropa[c]chromene-1-carboxylic acid

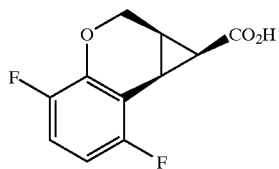

BBr$_3$ 1M solution in CH$_2$Cl$_2$ (5.8 ml; 5.8 mmol 2.1 eq) was added to starting lactone, (1S,5R,6S)-6-(3,6-difluoro-2-methoxyphenyl)-3-oxabicyclo[3.1.0]hexan-2-one from example 42c) (0.66 g; 2.75 mmol) at 0° C. The reaction mixture was stirred at 0° C. for 1 h. Acetonitrile (5.8 ml) was added and stirring was continued for 3 h at 0° C. The reaction mixture was quenched by addition of water and the organic phase was separated. Water phase was extracted with CH$_2$Cl$_2$ and combined organic phases were evaporated. NaOH (0.33 g; 8.25 mmol; 3 eq) in water (~5 ml) was added to the resulted residue and stirred at 80° C. for 45 min. The reaction mixture was extracted with ether to remove none acidic impurities. The residual ether in water phase was evaporated in vacuo and conc. HCl was added to pH of ~3. After ~1 h the solid was filtered off yielding 0.497 g (80%) of crude final acid as brownish solid. The crude acid was dissolved in 6 ml of EtOH/H$_2$O (40/60 v/v) and treated with activated carbon. The hot solution was filtered and left for crystallization. Yield 0.4 g (64%).

EXAMPLE 50

N-[(1S,1aR,7bR)-4,7-difluoro-1,1a,2,7b-tetrahydrocyclopropa[c]chromen-1-yl]-N'-(5-fluoro-2-pyridinyl)urea

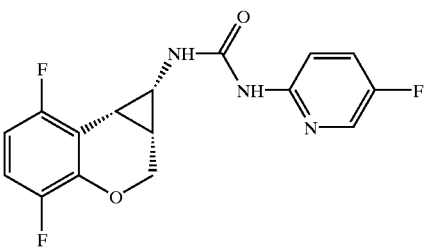

(1S,1aR,7bS)-4,7-difluoro-1,1a,2,7b-tetrahydrocyclopropa[c]chromene-1-carboxylic acid (50 mg, 0.22 mmol, ee ~90%) was mixed with toluene (1 ml), triethylamine (0.034 ml, 1.1 eq), 2-amino-5-fluoropyridine (28 mg, 1.1 eq), DPPA (0.054 ml, 1.1 eq). The reaction mixture was then heated at stirring at 110° C. for 3 h. The reaction mixture was concentrated by rotary evaporation and purified by column chromatography on silica (50 g, ethylacetate/hexane 1:1) to give 30 mg of the product as white solid.

$^1$H-NMR (DMSO-d$_6$): 9.34 (br s, ~1H), 7.85 (br d, 2H), 7.6 (d t, 1H), 7.33 (dd, 1H), 7.06 (m, 1H), 6.77 (dt, 1H), 4.29 (m, 2H), 3.48 (m, 1H), 2.48 (m, 1H/overlapped with DMSO signal), 2.00 (m, 1H). LC-MS: M$^+$ 336

EXAMPLE 51

N-[(1S,1aR,7bR)-4,7-difluoro-1,1a,2,7b-tetrahydrocyclopropa[c]chromen-1-yl]-N'-(5-iodo-2-pyridinyl)urea

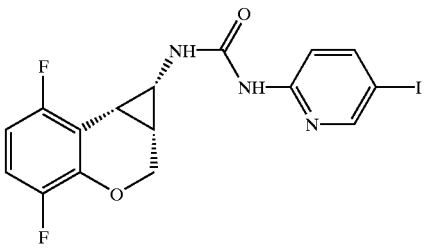

(1S,1aR,7bS)-4,7-difluoro-1,1a,2,7b-tetrahydrocyclopropa[c]chromene-1carboxylic acid (50 mg, 0.22 mmol, ee ~90%) was mixed with toluene (1 ml), triethylamine (0.034 ml, 1.1 eq), 2-amino-5-iodopyridine (54 mg, 1.1 eq), DPPA (0.054 ml, 1.1 eq). The reaction mixture was then heated at stirring at 110° C. for 3 h. The reaction mixture was concentrated by rotary evaporation and purified by column chromatography on silica (50 g, ethylacetate/hexane 1:1) to give 35 mg of the product as white solid.

$^1$H-NMR (DMSO-d$_6$): 9.4 (br s, ~1H), 8.07 (d, 1H), 8.02 (br s, 1H), 7.91 (dd, 1H), 7.11 (d, 1H), 7.06 (m, 1H), 6.77 (dt, 1H), 4.29 (br d, 2H), 3.5 (m, 1H), 2.46 (m, 1H/overlapped with DMSO signal), 2.00 (m, 1H). LC-MS: M$^+$ 444.

EXAMPLE 52

N-[(1S,1aR,7bR)-4,7-difluoro-1,1a,2,7b-tetrahydrocyclopropa[c]chromen-1-yl]-N'-(3-isoxazolyl)urea

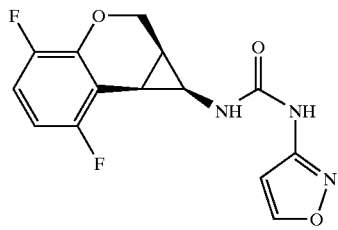

(1S,1aR,7bS)-4,7-difluoro-1,1a,2,7b-tetrahydrocyclopropa[c]chromene-1-carboxylic acid (50 mg, 0.22 mmol, ee ~90%) was mixed with toluene (1 ml), triethylamine (0.034 ml, 1.1 eq), 3-aminoisoxazole (0.018 ml, 1.1 eq), DPPA (0.054 ml, 1.1 eq). The reaction mixture was then heated at stirring at 110° C. for 3 h. The reaction mixture was concentrated by rotary evaporation and purified by column chromatography on silica (50 g, ethylacetate/hexane 1:1) to give 10 mg of the product as white solid.

$^1$H-NMR (DMSO-d$_6$): 9.45 (br s, ~1H), 8.6 (d, 1H), 7.06 (m, 1H), 6.75 (dt, 1H), 6.63 (d, 1H), 6.33 (br s, ~1H), 4.29 (m, 2H), 3.37 (overlapped with water signal), 2.43 (m, 1H), 1.98 (m, 1H). LC-MS: M$^+$ 308.

EXAMPLE 53

N-[(1S,1aR,7bR)-4,7-difluoro-1,1a,2,7b-tetrahydrocyclopropa[c]chromen-1-yl]-N'-[4-(4-chlorophenyl)-1,3-thiazol-2-yl]urea

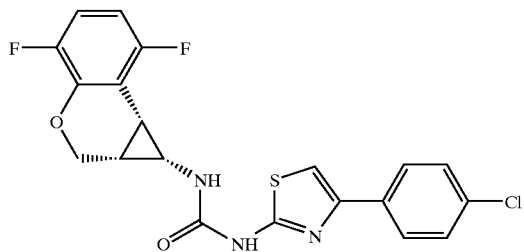

(1S,1aR,7bS)-4,7-difluoro-1,1a,2,7b-tetrahydrocyclopropa[c]chromene-1-carboxylic acid (50 mg, 0.22 mmol, ee ~90%) was mixed with toluene (1 ml), triethylamine (0.034 ml, 1.1 eq), 2-amino-4-(4-chlorophenyl)-1,3-thiazole (52 mg, 1.1 eq), DPPA (0.054 ml, 1.1 eq). The reaction mixture was then heated at stirring at 110° C. for 3 h. The reaction mixture was concentrated by rotary evaporation and the product was crystallized from ethanol and collected by filtration to give 50 mg of the product as white solid.

$^1$H-NMR (CDCl$_3$): 10.32 (br s, ~1H), 7.68 (d, 2H), 7.37 (s, 1H), 7.32 (d, 2H), 6.96 (s, 1H), 6.87 (m, 1H), 6.62 (dt, 1H), 4.44 (dd, 1H), 4.33 (dd, 1H), 3.53 (m, 1H), 2.56 (m, ~1H), 1.96 (m, 1H). LC-MS: M$^+$ 434.

EXAMPLE 54

N-[(1S,1aR,7bR)-4,7-difluoro-1,1a,2,7b-tetrahydrocyclopropa[c]chromen-1-yl]-N'-(6-fluoro-1,3-benzothiazol-2-yl)urea

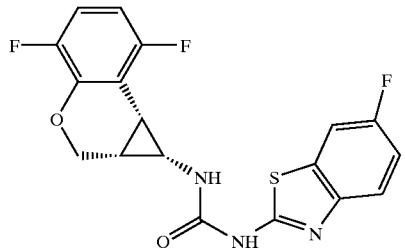

(1S,1aR,7bS)-4,7-difluoro-1,1a,2,7b-tetrahydrocyclopropa[c]chromene-1-carboxylic acid (50 mg, 0.22 mmol, ee ~90%) was mixed with toluene (1 ml), triethylamine (0.034 ml, 1.1 eq), 2-amino-6-fluoro-1,3-benzothiazole (41 mg, 1.1 eq), DPPA (0.054 ml, 1.1 eq). The reaction mixture was then heated at stirring at 110° C. for 3 h. The reaction mixture was concentrated by rotary evaporation and the product was crystallized from ethanol and collected by filtration to give 20 mg of the product as white solid.

$^1$H-NMR (CDCl$_3$): 10.58 (br s, ~1H), 7.78 (br d, 1H), 7.52 (dd, 1H), 7.45 (dd, 1H), 7.05 (dt, 1H), 6.94 (m, 1H), 6.65 (dt, 1H), 4.44 (dd, 1H), 4.33 (dd, 1H), 3.53 (m, 1H), 2.58 (m, ~1H), 2.03 (m, 1H). LC-MS: M$^+$ 434.

EXAMPLE 55

N-[(1S,1aR,7bR)-4,7-difluoro-1,1a,2,7b-tetrahydrocyclopropa[c]chromen-1-yl]-N'-(4-pyrimidinyl)urea

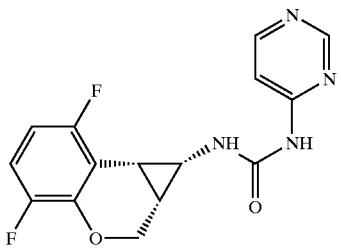

(1S,1aR,7bS)-4,7-difluoro-1,1a,2,7b-tetrahydrocyclopropa[c]chromene-1-carboxylic acid (50 mg, 0.22 mmol, ee ~90%) was mixed with toluene (1 ml), triethylamine (0.034 ml, 1.1 eq), 4-aminopyrimidine (25 mg, 1.1 eq), DPPA (0.054 ml, 1.1 eq). The reaction mixture was then heated with stirring at 110° C. for 3 h. The reaction mixture was concentrated by rotary evaporation and the product was crystallized from ethanol and collected by filtration to give 20 mg of the product as white solid.

$^1$H-NMR (DMSO-d$_6$): 9.71 (br s, 1H), 8.4 (br s, 1H), 8.39 (d, 1H), 7.86 (br s, 1H), 7.31 (d, 1H), 7.08 (m, 1H), 6.77 (dt, 1H), 4.31 (m, 2H), 3.48 (m, 1H), 2.48 (m, ~1H, overlapped with DMSO signal), 2.02 (m, 1H).

EXAMPLE 56

N-[(1S,1aR,7bR)-4,7-difluoro-1,1a,2,7b-tetrahydrocyclopropa[c]chromen-1-yl]-N'-(2-pyrazinyl)urea

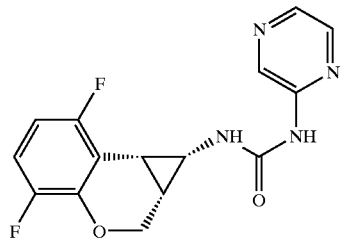

(1S,1aR,7bS)-4,7-difluoro-1,1a,2,7b-tetrahydrocyclopropa[c]chromene-1-carboxylic acid (50 mg, 0.22 mmol, ee ~90%) was mixed with toluene (1 ml), triethylamine (0.034 ml, 1.1 eq), 4-aminopyrazine (25 mg, 1.1 eq), DPPA (0.054 ml, 1.1 eq). The reaction mixture was then heated with stirring at 110° C. for 3 h. The reaction mixture was concentrated by rotary evaporation and the product was crystallized from ethanol and collected by filtration to give 5 mg of the product as white solid.

$^1$H-NMR (DMSO-d$_6$): 9.57 (br s, 1H), 8.67 (br s, 1H), 8.10 (d, 1H), 7.95 (br s, 1H), 7.64 (br s, 1H), 7.05 (m, 1H), 6.77 (dt, 1H), 4.31 (m, 2H), 3.49 (m, 1H), 2.48 (m, ~1H, overlapped with DMSO signal), 2.02 (m, 1H).

EXAMPLE 57

N-[(1S,1aR,7bR)-4,7-difluoro-1,1a,2,7b-tetrahydrocyclopropa[c]chromen-1-yl]-N'-(5-cyclopropyl-1H-pyrazol-3-yl)urea

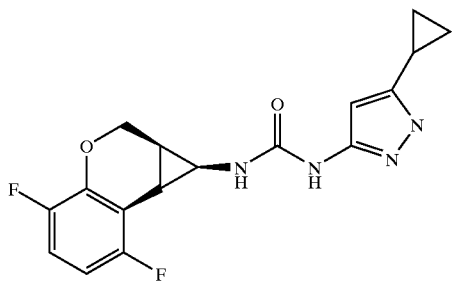

(1S,1aR,7bS)-4,7-difluoro-1,1a,2,7b-tetrahydrocyclopropa[c]chromene-1-carboxylic acid (50 mg, 0.22 mmol, ee ~90%) was mixed with toluene (1 ml), triethylamine (0.034 ml, 1.1 eq), 3-amino-5-cyclopropyl-1H-pyrazole (30 mg, 1.1 eq), DPPA (0.054 ml, 1.1 eq). The reaction mixture was then heated at stirring at 110° C. for 3 h. The reaction mixture was concentrated by rotary evaporation and two compounds were separated by column chromatography on silica (50 g, ethylacetate/hexane 1:3) to give 3 mg of the title product. The structure assignment was proved by $^{13}$C, gHMBC, gHMQC and NOESY NMR experiments.

$^1$H-NMR (CDCl$_3$): 7.05 (br d, ~1H), 6.88 (m, 1H), 6.64 (dt, 1H), 5.24 (d, 1H), 4.49 (dd, 1H), 4.33 (dd, 1H), 3.63 (m, 1H), 2.61 (m, ~2H), 1.99 (m, 1H), 0.99 (m, 2H), 0.58 (m, 2H).

Biological Results

Extensive guidance on the assay of test compounds at the enzyme level and in cell culture, including the isolation and/or selection of mutant HIV strains and mutant RT are found in DAIDS Virology Manual for HIV Laboratories complied by Division of AIDS, NIAID USA 1997. Resistance studies, including rational for various drug escape mutants is described in the HIV Resistance Collaborative Group Data Analysis Plan for Resistance Studies, revised 31, Aug. 1999.

Compounds of the invention are assayed for HIV activity, for example using multiple determinations with XTT in MT-4 cells (Weislow et al, J Nat Cancer Inst 1989, vol 81 no 8, 577 et seq), preferably including determinations in the presence of 40–50% human serum to indicate the contribution of protein binding. In short the XTT assay uses human T cell line MT4 cells grown in RPMI 1640 medium supplemented with 10% fetal calf serum (or 40–50% human serum as appropriate), penicillin and streptomycin seeded into 96 well microplates (2·10$^4$ cells/well) infected with 10–20 TCID$_{50}$ per well of HIV-1$_{IIIB}$ (wild type) or mutant virus, such as those bearing RT Ile 100, Cys 181 or Asn 103 mutations. Serially diluted test compounds are added to respective wells and the culture incubated at 37° C. in a CO$_2$ enriched atmosphere and the viability of cells is determined at day five or six with XTT vital dye. Results are typically presented as ED$_{50}$ μM.

Compounds of the invention were assayed in the above XTT assay using wild type HIV-1$_{IIIB}$ as shown in Table I:

TABLE 1

| Example | ED$_{50}$ (nM) |
|---|---|
| Example 7 | 7 |
| Example 16 | 6 |
| Example 18 | 6 |
| Example 19 | 10 |
| Example 20 | 7 |
| Example 23 | 7 |
| Example 24 | 20 |
| Example 30 | 3 |
| Example 31 | 2.5 |
| Example 33 | 9 |
| Example 43 | 2 |

Compounds are preferably potent against wild type virus and mutant HIV virus, especially virus comprising drug escape mutations. Drug escape mutations are those which arise in patients due to the selective pressure of a prior art antiviral and which confer enhanced resistance to that antiviral. The above cited Data Analysis Plan outlines relevant drug escape mutants for each of the antiviral classes currently on the market. Drug escape clones are readily isolated from HIV patients who are failing on a particular antiviral therapy. Alternatively the preparation of RT mutations on a known genetic background is shown in WO97/27319, WO99/61658 and WO00/73511 which also show the use of such mutants in sensitivity profiling.

K103 N is a particularly relevant drug escape mutant in the context of NNRTI therapy and compounds of the invention preferably have a low ED$_{50}$ against this mutant, especially in assays mimicking the presence of human serum. Compounds of the invention, such as those exemplified above show sub micromolar activities in such assays.

What is claimed is:

1. A compound of formula III:

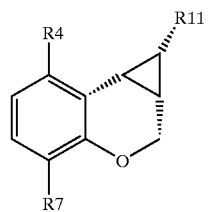

where $R_4$ and $R_7$ are independently halo and $R_{11}$ is —COOH, a lower alkyl ester thereof.

2. A compound according to claim 1, wherein $R_4$ and $R_7$ are fluoro.

3. A compound according to claim 1, wherein $R_4$ is fluoro.

4. A compound according to claim 1, wherein $R_7$ is fluoro.

5. A compound of the formula

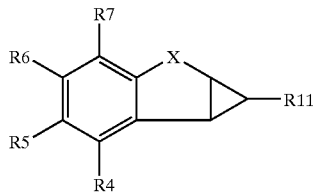

where X is —$(CH_2)_n$—D—$(CH_2)_m$—
D is —O—;
n is 0 or 1; m is 0;
$R_4$ and $R_7$ are independently selected from the group consisting of $C_1$–$C_6$ alkyl, $C_2$–$C_6$ alkenyl, $C_2$–$C_6$ alkynyl, halo$C_1$–$C_6$ alkyl, $C_1$–$C_6$ alkanoyl, halo$C_1$–$C_6$ alkanoyl, $C_1$–$C_6$ alkoxy, halo$C_1$–$C_6$ alkoxy, $C_1$–$C_6$ alkyloxy-$C_1$–$C_6$ alkyl, halo$C_1$–$C_6$ alkyloxy-$C_1$–$C_6$ alkyl, hydroxy-$C_1$–$C_6$ alkyl, amino-$C_1$–$C_6$ alkyl, carboxy-$C_1$–$C_6$ alkyl, cyano-$C_1$–$C_6$ alkyl, amino, carboxy, carbomoyl, cyano, halo and hydroxy;
$R_5$ and $R_6$ are independently selected from the group consisting of hydrogen, $C_1$–$C_6$ alkyl, $C_2$–$C_6$ alkenyl, $C_2$–$C_6$ alkynyl, halo$C_1$–$C_6$ alkyl, $C_1$–$C_6$ alkanoyl, halo$C_1$–$C_6$ alkanoyl, $C_1$–$C_6$ alkoxy, halo$C_1$–$C_6$ alkoxy, $C_1$–$C_6$ alkyloxy-$C_1$–$C_6$ alkyl, halo$C_1$–$C_6$ alkyloxy-$C_1$–$C_6$ alkyl, hydroxy-$C_1$–$C_6$ alkyl, amino-$C_1$–$C_6$ alkyl, carboxy-$C_1$–$C_6$ alkyl, cyano-$C_1$–$C_6$ alkyl, amino, carboxy, carbamoyl, cyano, halo and hydroxy;

$R_{11}$ is —$C(O)OR_{12}$; $R_{12}$ is H; and wherein the compound is at least 75% enantiomerically pure with respect to the conformation around the cyclopropyl group, as depicted in the partial structure:

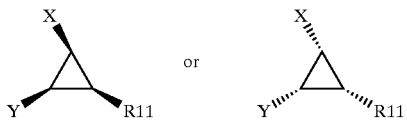

where X and $R_{11}$ are as defined and Y is the bridge to the (substituted) phenyl depicted in formula II.

6. A compound according to claim 5, wherein $R_4$ is halo or hydroxy.

7. A compound according to claim 6, wherein $R_4$ is fluoro.

8. A compound according to claim 5, wherein $R_5$ is hydrogen, halo, $C_1$–$C_3$alkylcarbonyl, $C_1$–$C_3$alkyloxy.

9. A compound according to claim 8, wherein $R_5$ is hydrogen.

10. A compound according to claim 5, wherein $R_6$ is hydrogen, halo, $C_1$–$C_3$alkyloxy, $C_1$–$C_3$alkylcarbonyl, cyano or ethynyl.

11. A compound according to claim 10, wherein $R_6$ is methoxy or fluoro.

12. A compound according to claim 10, wherein $R_6$ is hydrogen.

13. A compound according to claim 5, wherein $R_7$ is halo, $C_1$–$C_3$alkyloxy, $C_1$–$C_3$alkylcarbonyl.

14. A compound according to claim 13, wherein $R_7$ is fluoro.

* * * * *